United States Patent
Itoh et al.

(10) Patent No.: US 9,057,683 B2
(45) Date of Patent: Jun. 16, 2015

(54) IMAGE PICKUP UNIT AND VEHICLE IN WHICH IMAGE PICKUP UNIT IS MOUNTED

(71) Applicants: Izumi Itoh, Tokyo (JP); Hideaki Hirai, Kanagawa (JP)

(72) Inventors: Izumi Itoh, Tokyo (JP); Hideaki Hirai, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/349,370

(22) PCT Filed: Oct. 25, 2012

(86) PCT No.: PCT/JP2012/078266
§ 371 (c)(1),
(2) Date: Apr. 3, 2014

(87) PCT Pub. No.: WO2013/065765
PCT Pub. Date: May 10, 2013

(65) Prior Publication Data
US 2014/0303853 A1    Oct. 9, 2014

(30) Foreign Application Priority Data

Nov. 2, 2011 (JP) ................................ 2011-240848
Sep. 4, 2012 (JP) ................................ 2012-194246

(51) Int. Cl.
| | |
|---|---|
| G01N 21/00 | (2006.01) |
| G01N 21/17 | (2006.01) |
| B60R 11/04 | (2006.01) |
| B60S 1/08 | (2006.01) |
| G01W 1/14 | (2006.01) |
| H04N 5/72 | (2006.01) |

(Continued)

(52) U.S. Cl.
CPC ............... G01N 21/17 (2013.01); B60R 11/04 (2013.01); B60R 2011/0026 (2013.01); B60S 1/0844 (2013.01); G01N 21/55 (2013.01); G01W 1/14 (2013.01); H04N 5/72 (2013.01)

(58) Field of Classification Search
None
See application file for complete search history.

(56) References Cited

U.S. PATENT DOCUMENTS

| | | | | |
|---|---|---|---|---|
| 4,701,613 | A | * 10/1987 | Watanabe et al. ............. | 340/602 |
| 5,059,877 | A | * 10/1991 | Teder ............................. | 318/444 |
| 5,572,315 | A | * 11/1996 | Krell ............................. | 356/136 |

(Continued)

FOREIGN PATENT DOCUMENTS

| | | |
|---|---|---|
| JP | 60-216245 | 10/1985 |
| JP | 06-028716 U | 4/1994 |

(Continued)

OTHER PUBLICATIONS

International Search Report Issued on Feb. 5, 20130 PCT/JP2012/078266 filed on Oct. 25, 2012.

*Primary Examiner* — Jonathan M Dager
(74) *Attorney, Agent, or Firm* — IPUSA, PLLC

(57) ABSTRACT

An image pickup lens has a focal length far from a position of a transparent member. An image pickup device is put on the side of the transparent member the same as that of a light source and takes reflected light including regular reflection from an interface between an adhered object on the other surface of the transparent member and air. Assuming an incident angle of the emitted light on the transparent member when the light reflected in regular reflection by the other surface of the transparent member is incident on the image pickup lens being θs, an incident angle of a typical light beam of the emitted light falls within θs–30 deg through θs and an incident angle of a main element of the emitted light is less than θs.

11 Claims, 42 Drawing Sheets

(51) Int. Cl.
  *B60R 11/00* (2006.01)
  *G01N 21/55* (2014.01)

(56) References Cited

U.S. PATENT DOCUMENTS

| | | | | |
|---|---|---|---|---|
| 5,661,303 | A * | 8/1997 | Teder | 250/341.8 |
| 5,991,049 | A * | 11/1999 | Tanaka et al. | 356/445 |
| 5,998,782 | A * | 12/1999 | Koyama et al. | 250/227.25 |
| 6,064,059 | A * | 5/2000 | Pientka et al. | 250/227.24 |
| 6,207,967 | B1 * | 3/2001 | Hochstein | 250/574 |
| 6,232,603 | B1 * | 5/2001 | Nelson | 250/339.11 |
| 6,262,407 | B1 * | 7/2001 | Teder | 250/205 |
| 6,285,037 | B1 * | 9/2001 | Koyama et al. | 250/574 |
| 6,307,198 | B1 * | 10/2001 | Asakura et al. | 250/227.25 |
| 6,320,176 | B1 * | 11/2001 | Schofield et al. | 250/208.1 |
| 6,507,015 | B1 | 1/2003 | Maeno et al. | |
| 6,627,910 | B2 * | 9/2003 | Ishino et al. | 250/573 |
| 6,855,947 | B2 * | 2/2005 | Graves et al. | 250/573 |
| 7,236,249 | B1 | 6/2007 | Michenfelder et al. | 356/445 |
| 7,253,898 | B2 * | 8/2007 | Saikalis et al. | 356/338 |
| 7,310,190 | B2 * | 12/2007 | Fox | 359/666 |
| 7,612,356 | B2 * | 11/2009 | Utida et al. | 250/573 |
| 8,861,780 | B2 * | 10/2014 | Heenan et al. | 382/100 |
| 8,914,197 | B2 * | 12/2014 | Chen et al. | 701/49 |
| 2003/0156291 | A1 * | 8/2003 | Tsunetomo et al. | 356/445 |
| 2004/0075828 | A1 * | 4/2004 | Sautter et al. | 356/239.8 |
| 2005/0035926 | A1 * | 2/2005 | Takenaga et al. | 345/8 |
| 2006/0043322 | A1 * | 3/2006 | Ishikawa | 250/573 |
| 2006/0215164 | A1 * | 9/2006 | Takata et al. | 356/445 |
| 2007/0235638 | A1 * | 10/2007 | Backes et al. | 250/227.24 |
| 2009/0032689 | A1 * | 2/2009 | Backes | 250/227.24 |
| 2009/0261237 | A1 * | 10/2009 | Backes | 250/227.11 |
| 2010/0208060 | A1 * | 8/2010 | Kobayashi et al. | 348/135 |
| 2013/0027557 | A1 * | 1/2013 | Hirai et al. | 348/148 |
| 2014/0029008 | A1 * | 1/2014 | Hirai et al. | 356/445 |
| 2014/0184800 | A1 * | 7/2014 | Hirai et al. | 348/148 |
| 2014/0321709 | A1 * | 10/2014 | Kasahara et al. | 382/103 |

FOREIGN PATENT DOCUMENTS

| | | |
|---|---|---|
| JP | 2000-193586 | 7/2000 |
| JP | 3536738 | 6/2004 |
| JP | 2005-225250 | 8/2005 |
| JP | 4326999 | 9/2009 |
| JP | 2010-204059 | 9/2010 |
| JP | 2010-210374 | 9/2010 |
| JP | 2010-210607 | 9/2010 |
| WO | 01/86259 A1 | 11/2001 |
| WO | 2005/075248 A1 | 8/2005 |

* cited by examiner

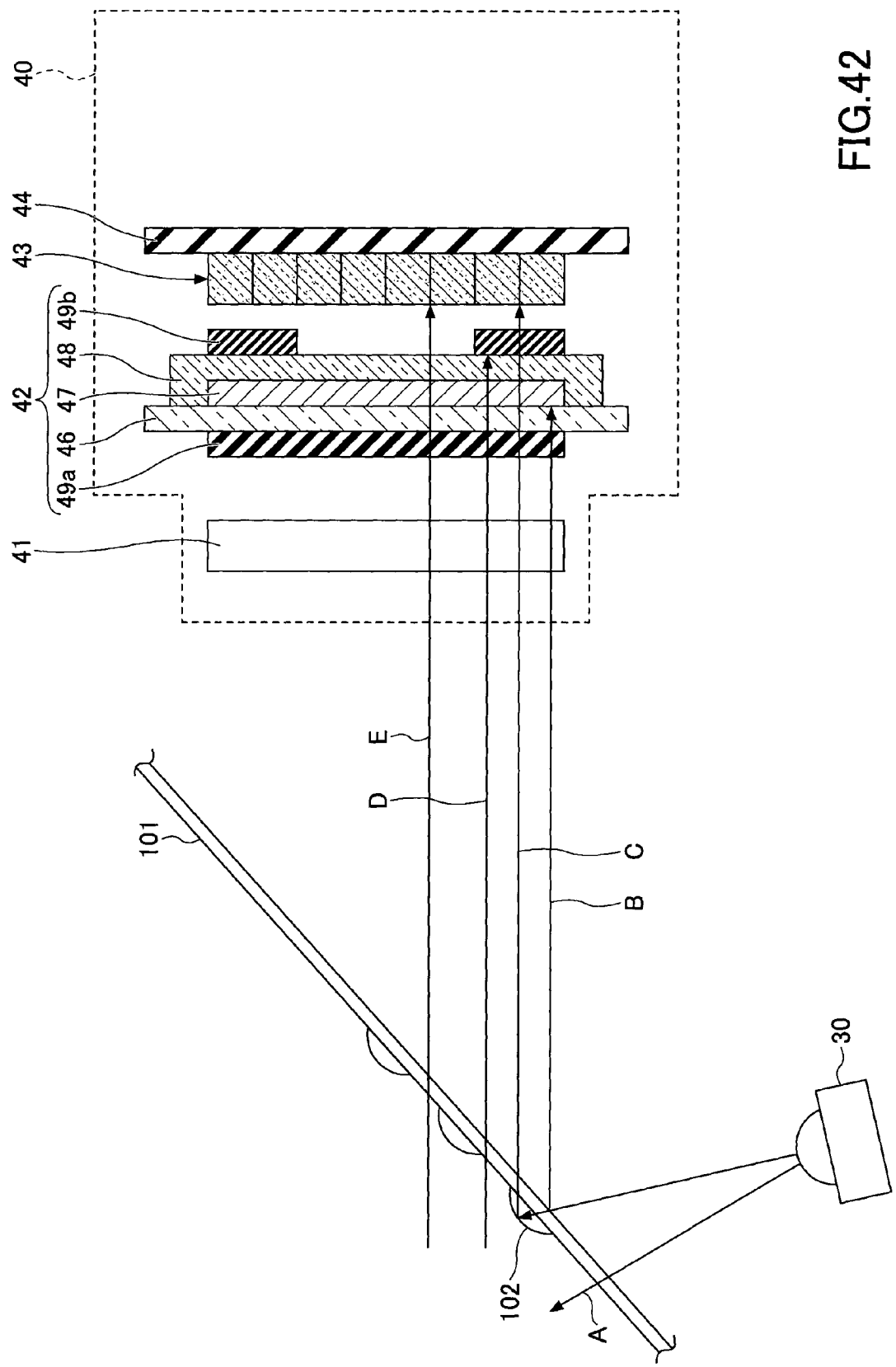

IMAGE PICKUP UNIT AND VEHICLE IN WHICH IMAGE PICKUP UNIT IS MOUNTED

TECHNICAL FIELD

The present invention is related to an image pickup unit that takes an image and a vehicle in which the image pickup unit is mounted.

BACKGROUND ART

In the related art, an image processing apparatus is known which is mounted in a vehicle such as an automobile, detects a raindrop and monitors surroundings of the vehicle. In such an image processing apparatus, an image pickup unit that takes an image is mounted.

For example, there is an image processing apparatus that includes a lens that can have a first focal length for a short distance for taking an image of a raindrop that has adhered to a vehicle and a second focal length for a long distance for taking an image of surroundings of the vehicle; a camera part that switches between the first focal length and the second focal length; a raindrop detection part that detects whether there is a raindrop based on an image taken by the camera part with the first focal length; and a monitoring part that monitors surroundings of the vehicle based on an image taken by the camera part with the second focal length. In this image processing apparatus, the camera part corresponds to an image pickup unit (for example, see Japanese Laid-Open Patent Application No. 2005-225250 (Patent Reference No. 1)).

However, the image pickup unit (camera part) of the Patent Reference No. 1 uses the bifocal lens, focuses the lens on a raindrop when detecting the raindrop that has adhered to the windshield surface and focuses the lens on surroundings of the vehicle when detecting the vehicle surrounding information. Thus, when a raindrop is detected while the lens is focused on a windshield surface, it may be difficult to extract an area of the raindrop because the contrast between the raindrop and the background may be included in an image of the raindrop and also a position of a bright spot may be moved according to a position of a light source.

That is, according to the image pickup unit (camera part) of the Patent Reference No. 1, it may be difficult to take an image of a raindrop that has adhered to a windshield surface and vehicle surrounding information that is far from the position of the windshield in the respective suitable conditions.

SUMMARY OF INVENTION

An image pickup unit includes a light source that emits light toward a transparent member from a side of one surface of the transparent member; an image pickup lens having a focal length that is set far from a position of the transparent member; an image sensor that includes plural pixels arranged two-dimensionally; and an image pickup device that is put on the side of the transparent member the same as that of the light source. The image pickup device takes an image of reflected light that includes regular reflection of the emitted light reflected by an interface between an adhered object that adheres to the other surface of the transparent member and air by the image sensor. The light source is set in a position such that in a case where an incident angle of the emitted light on the transparent member when the light reflected in a regular reflection manner by the other surface of the transparent member is incident on the image pickup lens is θs, an incident angle of a typical light beam of the emitted light on the transparent member falls within a range θs−30 deg through θs and an incident angle of a main element of the emitted light on the transparent member is less than θs.

Other objects, features and advantages of the present invention will become more apparent from the following detailed description when read in conjunction with the accompanying drawings.

BRIEF DESCRIPTION OF DRAWINGS

FIG. 30 illustrates transmittance characteristics of a spectral filter layer 49a;

FIG. 42 illustrates light beams concerning raindrop detection and vehicle detection;

DESCRIPTION OF EMBODIMENTS

Figure 1:
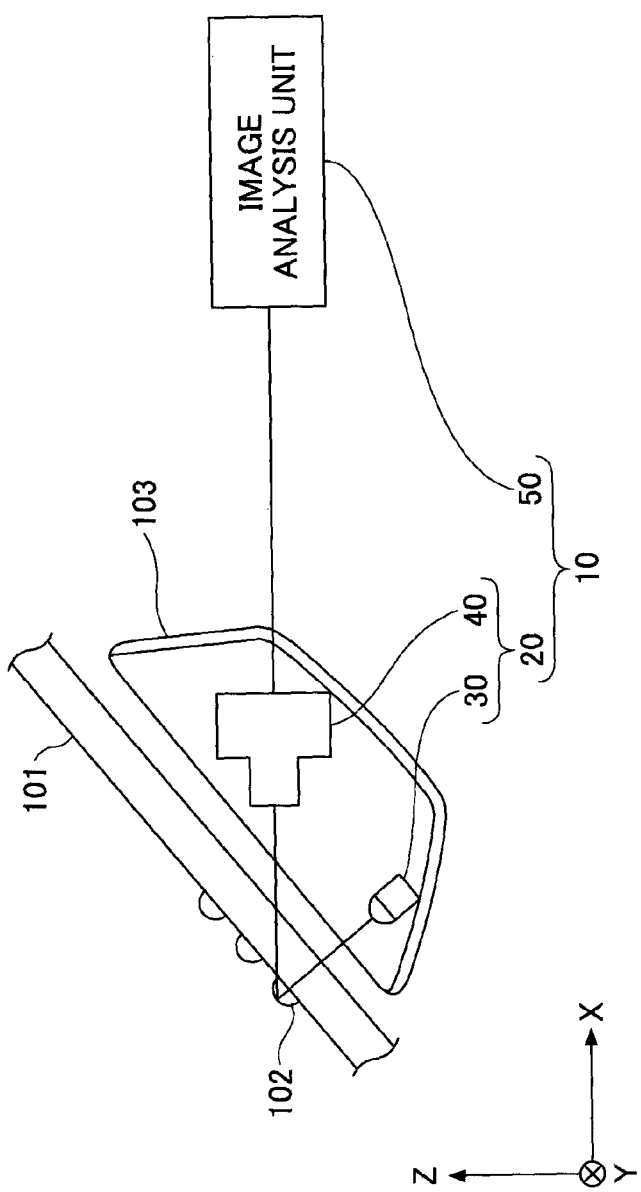
FIG. 1 shows a schematic diagram illustrating a general configuration of an image processing apparatus 10 according to a first embodiment.

Below, the embodiment and the variants thereof will be described using figures. In each figure, the same reference numerals will be given to the same elements, and duplicate descriptions may be omitted.

It is noted that in the embodiment and the variants thereof described below, examples will be described in which an image processing apparatus is mounted which uses an image pickup unit in a vehicle such as an automobile and takes an image of an adhered object such as a raindrop that has adhered to a windshield of the vehicle or vehicle surrounding information such as a headlight of another vehicle.

First Embodiment

Figure 2:
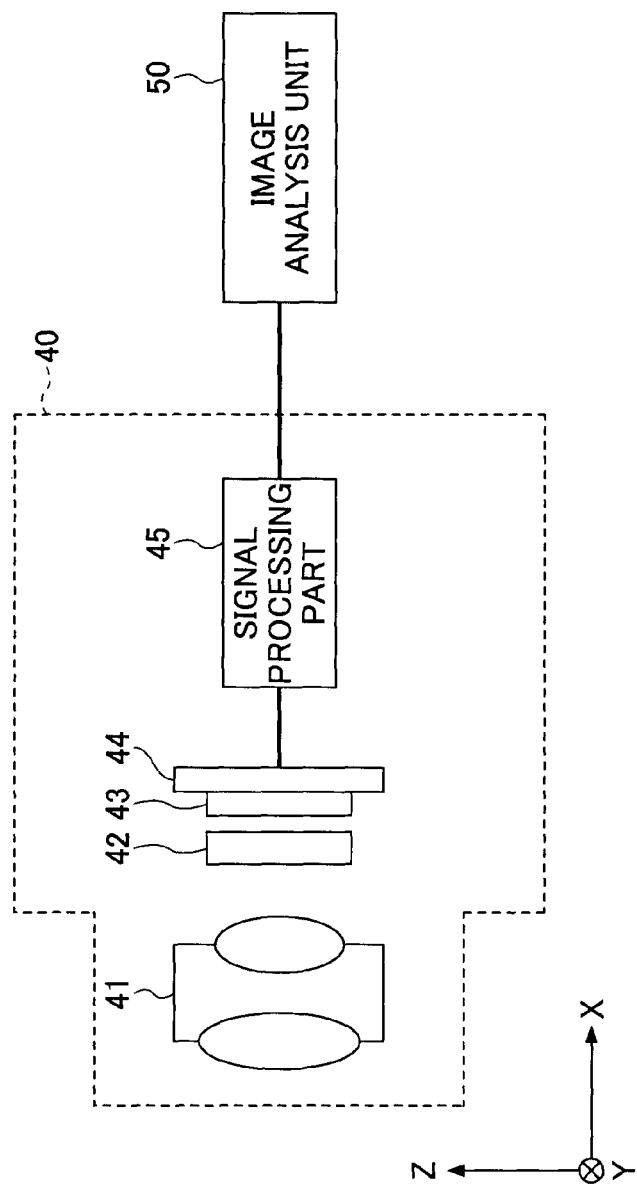
FIG. 2 shows a schematic diagram illustrating a part of FIG. 1 in a magnifying manner.

FIG. 1 is a schematic diagram illustrating a general configuration of an image processing apparatus 10 according to a first embodiment. FIG. 2 is a schematic diagram illustrating a part of FIG. 1 in a magnifying manner. As shown in FIGS. 1 and 2, the image processing apparatus 10 includes an image pickup unit 20 and an image analysis unit 50. It is noted that the reference numeral 101 denotes a windshield of a vehicle and the reference numeral 102 denotes a raindrop that has adhered to the outer wall surface the windshield 101. It is noted that the windshield 101 is a typical example of a transparent member. The raindrop 102 is a typical example of an adhered object.

The image pickup unit 20 is installed, for example, near the windshield 101 of the vehicle (for example, around the rear-view mirror (not shown)). It is also possible to install the image pickup unit 20 near the windshield 101, for example, in a state of being covered by a transparent cover 103 that is transparent at least on the side of the windshield 101.

Further, it is also possible to cause the cover 103 that has an opening on the side of the windshield 101 to fit onto the windshield 101, and put (place) the image pickup unit 20 so as to be covered by the windshield 101 and the cover 103. In this case, it is possible to prevent the part of the windshield 101 covered by the cover 103 from being fogged although in a state of the inner wall surface of the windshield 101 being fogged. As a result, it is possible to prevent the image analysis unit 50 from carrying out an erroneous analysis due to the windshield 101 being fogged, and it is possible to appropriately carry out various sorts of control operations based on the analysis results of the image analysis unit 50.

However, in a case where it is to be detected that the windshield 101 has been fogged and air-conditioning equipment of the occupant vehicle is controlled, an air flow path may be provided in the cover 103 such that the part of the windshield 101 which faces the image pickup unit 20 will have the same condition as the other part.

The image pickup unit 20 includes a light source 30 and an image pickup device 40. The light source 30 is provided for detecting an adhered object that has adhered to the windshield 101, and has a function of emitting light toward the windshield 101 from the side (the inner wall surface) of one surface of the windshield 101. The light source 30 is provided at a position such that it is possible to emit light at least to an adhered object detection image area (raindrop detection image area) defined for detecting an adhered object that has adhered to the windshield 101.

For example, in a case where the adhered object detection image area is a lower end part of the windshield 101, the light source 30 is provided at a position such as to be able to emit light at least to the lower end part of the windshield 101. In a case where the adhered object detection image area is an upper end part and a lower end part of the windshield 101, the light source 30 is provided at a position such as to be able to emit light at least to the upper end part and lower end part of the windshield 101. In a case where the adhered object detection image area is the entire surface of the windshield 101, the light source 30 is provided at a position such as to be able to emit light at least to the entire surface of the windshield 101. It is also possible to provide plural of the light sources 30 in order to positively emit light to the adhered object detection image area.

As the light source 30, for example, a light emitting diode (LED), a semiconductor laser (LD) or the like may be used. As the oscillation wavelength, for example, visible light, infrared light or the like may be used.

However, it is necessary to prevent the light of the light source 30 from dazzling the driver of an oncoming vehicle, a pedestrian or the like. Thus, it is preferable to select a range of wavelength (for example, wavelengths of the infrared light area greater than or equal to 800 nm and less than or equal to 1000 nm) which is longer than the visible light and detectable by the light receiving sensitivity of an image sensor 43 described later. Hereinafter, description will be made for an example of the light source 30 that emits light having wavelengths of the infrared light area.

It is noted that emitted light of the light source 30 may be preferably approximately parallel light. It is possible to generate parallel light by providing a collimator lens or the like immediately subsequent to the light source 30. Thus, the light source 30 may include an element(s) such as a lens and/or the like for adjusting a mode or a form of the emitted light.

The image pickup device 40 is provided on the same side as that of the light source 30 with respect to the windshield 101, and has a function of taking an image of reflected light of light emitted to a raindrop 102 by the light source 30 or incident light from the outside of the occupant vehicle. According to the first embodiment, the image pickup device 40 is put in such a manner that the optical axis of an image pickup lens 41 extends along a horizontal direction (X-direction). However, it is not necessary to limit thereto. The light source 30 is put in a position such that reflected light of light emitted to a raindrop 102 from the light source 30 will be incident on the image pickup device 40.

The image pickup device 40 includes the image pickup lens 41, an optical filter 42, the image sensor 43, a sensor substrate 44 and a signal processing part 45. The image pickup lens 42 includes, for example, plural lenses, and has a focal point that is set far from the position of the windshield 101. The focal position of the image pickup lens 41 may be set, for example, to infinity or between infinity and the windshield 101.

The optical filter 42 is put subsequent to the image pickup lens 41, and has a function of limiting a band of wavelengths of light incident on the image sensor 43. The image sensor 43 includes plural pixels that are arranged two-dimensionally for receiving light that has passed through the optical filter 42, and has a function of carrying out photoelectric conversion on incident light for each pixel. The image sensor 43 is mounted on the sensor substrate 44. It is noted that in FIG. 6 and so forth described later, the respective pixels of the image sensor 43 are shown in a simplifying manner. However, actually, the image sensor 43 includes the pixels arranged two-dimensionally and the number of pixels is on the order of hundreds of thousands.

As the image sensor 43, for example, a charge coupled device (CCD), a complementary metal oxide semiconductor (CMOS) or the like may be used. Microlenses or the like may be provided corresponding to the respective pixels on the incident side of the image sensor 43, and thus, the light condensing efficiency for the image sensor 43 may be improved.

The signal processing part 45 has a function of converting an analog electric signal (incident amounts of light of the respective pixels of the image sensor 43) which is output from the sensor substrate 44 after undergoing the photoelectric conversion by the image sensor 43 into a digital electric signal which is referred to as pickup image data. Thus, the signal processing part 45 generates the pickup image data. The signal processing part 45 is electrically connected to the image analysis unit 50.

Light emitted by the light source 30 to a raindrop 102 that has adhered to the outer wall surface of the windshield 101 is reflected by the interface between the raindrop 102 and the air, and is incident on the image sensor 43 via the image pickup lens 41 and the optical filter 42. The light that is thus incident on the image sensor 43 is then converted by the image sensor 43 into an electric signal that corresponds to the light intensity.

When the electric signal (analog signal) is thus input from the image sensor 43 via the sensor substrate 44, the signal processing part 45 outputs based on the input electric signal the digital signal (pickup image data) that indicates brightness of each pixel of the image sensor 43 together with image horizontal and vertical synchronization signals to the subsequent image analysis unit 50.

The image analysis unit 50 has a function of controlling the image pickup device 40 and a function of analyzing the pickup image data transmitted from the image pickup device 40. Specifically, the image analysis unit 50 has a function of calculating optimum exposure amounts of the respective image pickup areas of the image sensor 43 from the pickup image data transmitted from the image pickup device 40, and setting the optimum exposure amounts (adjusting the exposure periods of time to the optimum ones) for the respective image pickup areas of the image sensor 43.

Further, the image analysis unit 50 has a function of detecting from the pickup image data transmitted from the image pickup device 40 an adhered object that has adhered to the windshield 101 such as a raindrop 102, a foreign object or the like and detecting a detection target existing in the image pickup area such as a white line on the road (carriageway marking) or the like.

Further, the image analysis unit 50 has a function of calculating, from the pickup image data transmitted from the image pickup device 40, the position, direction, distance and/ or the like of another vehicle that exists in front of the occupant vehicle. Further, the image analysis unit 50 has a function of detecting from the pickup image data transmitted from the image pickup device 40 a vehicle that moves ahead of the occupant vehicle in the same direction as that of the occupant vehicle by identifying a taillight of the other vehicle and/or detecting from the pickup image data transmitted from the image pickup device 40 an oncoming vehicle that moves in the direction opposite to that of the occupant vehicle by identifying a headlight of the other vehicle.

[Detailed Description of Image Processing Apparatus]

The image processing apparatus 10 will now be described in more detail. First, detection of an adhered object which is one function of the image analysis unit 50 will be described in detail using a case where the adhered object is a raindrop 102 as an example.

[Focus of Image Pickup Lens 41]

In a case where no raindrop 102 has adhered to the outer wall surface of the windshield 101, light emitted from the light source 30 is reflected by the interface between the outer wall surface of the windshield 101 and the open air, and the reflected light is incident on the image pickup device 40. On the other hand, in a case where, as shown in FIG. 1, a raindrop 102 has adhered to the outer wall surface of the windshield 101, the refractive index difference between the outer wall surface of the windshield 101 and the raindrop 102 is smaller than the refractive index difference between the outer wall surface of the windshield 101 and the open air.

Thus, the light emitted from the light source 30 is transmitted by the interface between the outer wall surface of the windshield 101 and the raindrop 102 and is incident on the raindrop 102. The light thus incident on the raindrop 102 is reflected by the interface between the raindrop 102 and the open air and the reflected light is incident on the image pickup device 40. Based on such a difference caused by whether the raindrop 102 exists, the image analysis unit 50 can detect from the pickup image data transmitted from the image pickup device 40 whether such a raindrop 102 that has adhered to the windshield 101 exists.

According to the first embodiment, the focal position of the image pickup lens 41 is set to infinity or between infinity and the windshield 101. Thus, the image analysis part 50 can obtain appropriate information from the pickup image data of the image pickup device 40 not only in a case of detecting the raindrop 102 that has adhered to the outer wall surface of the windshield 101 but also in a case of detecting a vehicle that moves ahead of the occupant vehicle or an oncoming vehicle or detecting a white line.

For example, in a case of detecting a raindrop 102 that has adhered to the outer wall surface of the windshield 101, the shape of the image of the raindrop 102 on the pickup image data is in many cases a circular shape. Thus, the image analysis unit 50 carries out a shape recognition process of determining that a given candidate image for a raindrop 102 is actually an image of a raindrop 102 by determining whether the candidate image for a raindrop 102 has a circular shape.

In a case of carrying out such a shape recognition process, the detection performance for a raindrop 102 is improved in a case where as mentioned above the image pickup lens 41 is focused to infinity or between infinity and the windshield 101, thus somewhat "being out of focus" occurs and the shape recognition rate (for a circular shape) is improved more than a case of "being focused on the raindrop 102" that has adhered to the outer wall surface of the windshield 101.

The example has been thus described using the fact that a raindrop 102 has a circular shape and carrying out the shape recognition process. However, as a method requiring a lesser processing load, it is also possible to detect adhesion of a raindrop 102 by counting the increased amount of brightness value which increase occurs when a raindrop 102 has adhered to the windshield 101.

When a raindrop 102 has adhered to the windshield 101, the electric signal (analog signal) is input to the signal processing part 45 from the image sensor 43 via the sensor substrate 44. Then, from the electric signal that is thus input to the signal processing part 45, the signal processing part 45 outputs the digital signal (pickup image data) that indicates brightness of each pixel of the image sensor 43 to the subsequent image analysis until 50 together with the image horizontal and vertical synchronization signals.

The image analysis unit 50 carries out raindrop detecting image processing. As a specific example, the brightness values of the specific pixels that are included in the image area defined for raindrop detection are increased in response to the above-mentioned adhesion of the raindrop 102. Then, the increased amount is compared with a predetermined threshold, and, in a case of (increased amount)>(threshold), the image analysis unit 50 outputs a signal that indicates the detection result that a raindrop exits.

Figure 3:
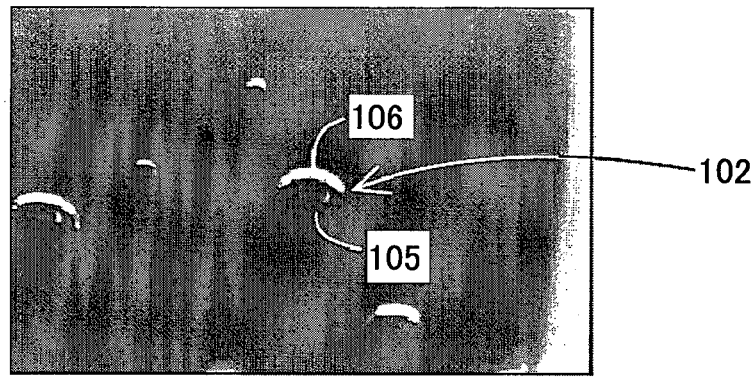
FIG. 3 illustrates pickup image data for raindrop detection in a case where an image pickup lens 41 is focused on a raindrop 102.
Figure 4:
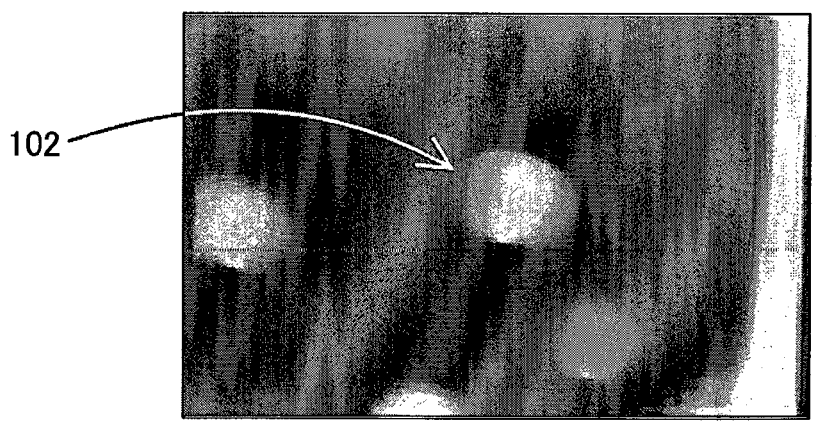
FIG. 4 illustrates pickup image data for raindrop detection in a case where the image pickup lens 41 is focused to infinity.

FIG. 3 illustrates the pickup image data to be used for the raindrop detection in a case where the image pickup lens 41 is focused on the raindrop 102. FIG. 4 illustrates the pickup image data to be used for the raindrop detection in a case where the image pickup lens 41 is focused to infinity. It is noted that FIGS. 3 and 4 show examples of cases where infrared light is emitted to the raindrop 102 by the light source 30.

As shown in FIG. 3, in a case where the image pickup lens 41 is focused on the raindrop 102 that has adhered to the outer wall surface of the windshield 101, also a background image 105 that is reflected in the raindrop 102 is taken. Such a background image 105 may cause erroneous detection of the raindrop 102. Further, there is a case where only a part 106 (having an arched shape or the like) of the raindrop 102 has high brightness. In such a case, the shape of the part 106 having high brightness changes due to the direction of the sun, the position of a street light or the like. In order to carry out the shape recognition process on the image of the thus variously changing shape of the raindrop 102, the processing load may be increased and the recognition accuracy may be degraded. Hereinafter, a part having brightness higher than the surroundings may be referred to as a "bright point".

On the other hand, as shown in FIG. 4, in a case where the image pickup lens 41 is focused to infinity, somewhat "being out of focus" occurs. Thus, the background image 105 reflected in the raindrop 102 is not actually reflected in the pickup image data. Thus, erroneous detection of the raindrop 102 can be reduced. Further, the somewhat "being out of focus" results in reduction of the degree of a change of the shape of the raindrop image which may occur due to the direction of the sun, the position of a street light or the like. Thus, the image of the raindrop 102 always has an approximately circular shape. Thus, it is possible to reduce the load of the shape recognition process for the raindrop 102, and also, it is possible to improve the recognition accuracy for the raindrop 102.

However, such a setting of the focus of the image pickup lens 41 may influence image pickup characteristics for an object other than a raindrop 102. For example, the number of pixels of the image sensor 43 which receive light from a taillight may be on the order of one when identifying the taillight of a vehicle that is moving ahead of the occupant vehicle far away while the image pickup lens 41 is focused to infinity, for example. In this case, it may not be possible to actually recognize the taillight, and thus, it may not be possible to detect the vehicle that is moving ahead of the occupant vehicle.

In order to avoid such a problem, it is preferable to focus the image pickup lens 41 short of infinity. Thus, a taillight of a vehicle moving ahead of the occupant vehicle far away is out of focus, and thus, it is possible to increase the number of pixels of the image sensor 43 that receive the light from the taillight. As a result, it is possible to improve the recognition accuracy for the taillight, and thus, it is possible to improve the detection accuracy for the vehicle that is moving ahead of the occupant vehicle.

[Detection of Bright Point]

Figure 5:
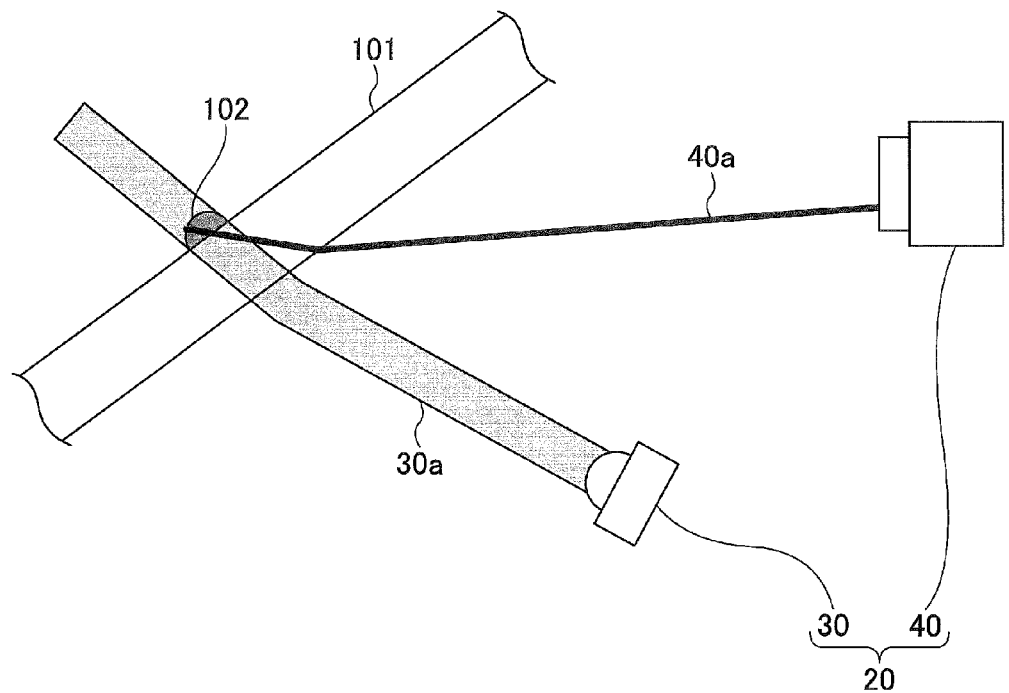
FIG. 5 illustrates detection of a bright point of a raindrop.

Now, description will be made for detection of a bright point mentioned above. FIG. 5 shows a side view illustrating detection of a bright point of a raindrop. A light beam 30a emitted by the light source 30 is refracted at the inner wall surface of the windshield 101, and is incident on the raindrop 102 that has adhered to the outer wall surface of the windshield 101 after being transmitted by the outer wall surface of the windshield 101. Reflected light is generated at a wide angle from the interface between the raindrop 102 and the air. However, only reflected light 40a that has a refracted angle at the inner wall surface of the windshield 101 corresponding to the angle of view of the image pickup device 40 is incident on the image pickup device 40, and an image thereof is taken by the image pickup device 40.

The reflected light 40a is reflected light from a very small area of the whole interface between the raindrop 102 and the air, and the image thereof is taken as a bright point. When the image pickup lens 41 is focused far away from the windshield 101, the bright point is blurred as mentioned above (due to "being out of focus"), and thus, the state of FIG. 4 is obtained.

Figure 6:
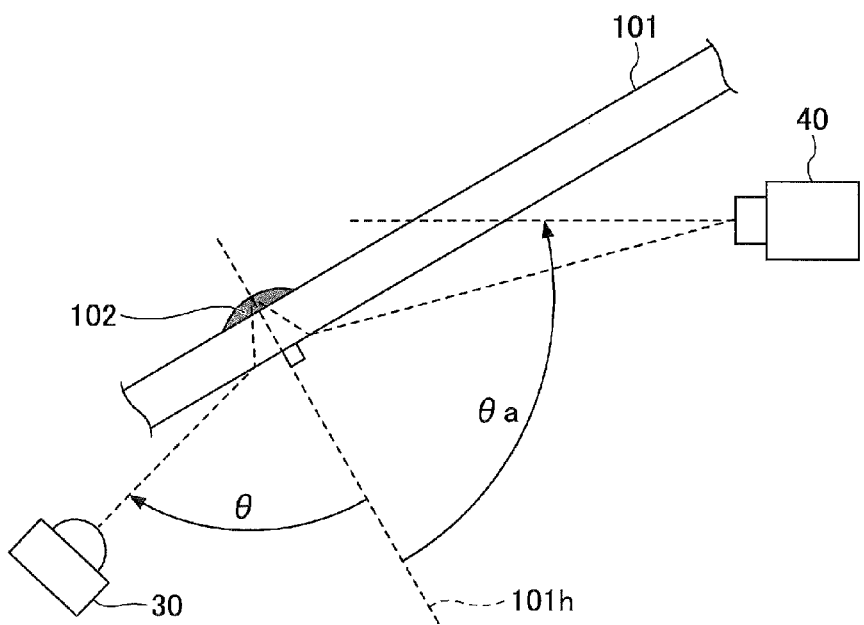
FIG. 6 shows a side view illustrating an arrangement of a light source 30 and the image pickup device 40.

FIG. 6 shows a side view illustrating an arrangement of the light source 30 and the image pickup device 40. In FIG. 6, the image pickup device 40 and the image pickup lens 41 (not shown) are arranged horizontally. The angle of elevation of the image pickup lens 41 (not shown) with respect to the normal 101h of the windshield 101 that intersects the optical axis of the image pickup lens 41 (not shown) is θa.

On the other hand, the angle of elevation of the light source 30 with respect to the normal 101h of the windshield 101 that intersects the optical axis of the image pickup lens 41 (not shown) is θ, and light emitted from the light source 30 is incident on the windshield 101 at the angle of elevation of θ. In other words, the incident angle of vertical direction of the emitted light from the light source 30 on the windshield 101 is θ.

It is noted that the angles of the respective parts in a case where the light source 30 and the image pickup device 40 are viewed in plan view (for example, a case of FIG. 20 or the like) may be referred to as "angles of horizontal direction". The angles of the respective parts in a case where the light source 30 and the image pickup device 40 are viewed in side view (for example, a case of FIG. 6 or the like) may be referred to as "angles of vertical direction".

The angle of elevation θ of the light source 30 (i.e., the incident angle θ of vertical direction of the emitted light from the light source 30 on the windshield 101) is set in the range "θs−30 deg<θ<θs" when the light source 30 is set at the angle θs so that the light reflected in a regular reflection manner by the outer wall surface of the windshield 101 will be incident on the image pickup lens 41.

In other words, the light source 30 is put in such a manner that in a case where the incident angle of the emitted light from the light source 30 on the windshield 101 when the light reflected by the outer wall surface of the windshield 101 in a regular reflection manner is incident on the image pickup lens 41 is θs, the incident angle of the emitted light from the light source 30 on the windshield 101 will fall within the range θs−30 deg through θs. It is noted that in FIG. 6, the clockwise direction is a − direction and the counterclockwise direction is a + direction.

By thus putting the light source 30 in the above-mentioned range, the image pickup device 40 can take an image of the reflected light that includes regular reflection of the emitted light from the light source 30 reflected by the interface between the raindrop 102 and the air.

Figure 7:
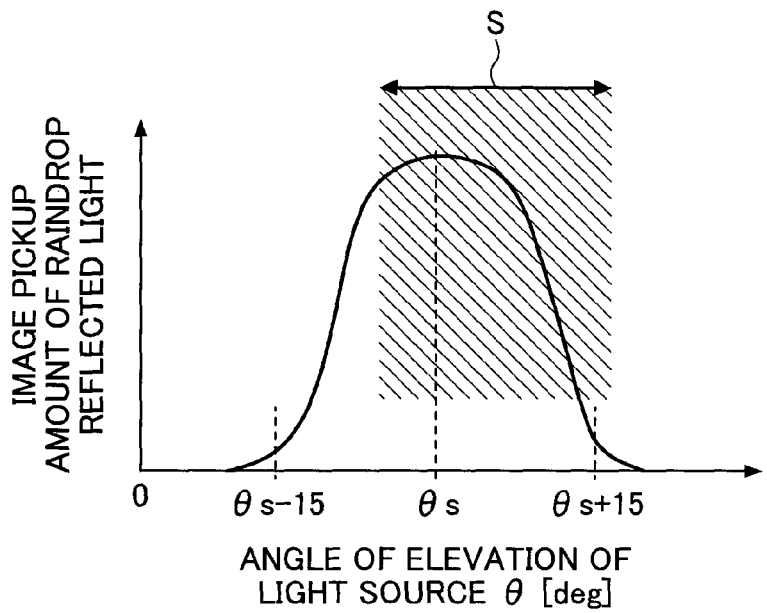
FIG. 7 illustrates a relationship between an angle of elevation θ of the light source 30 and an image pickup amount of reflected light.

FIG. 7 illustrates a relationship between the angle of elevation θ of the light source 30 and the image pickup amount of reflected light. The image pickup amount of reflected light from the interface between the raindrop 102 and the air from the emitted light of the light source 30 has the maximum value around the angle of elevation of the light source 30 being the angle θs. It is possible to obtain the image pickup amount of light in the range "θs−30 deg<θ<θs". However, it is not substantially possible to use the hatched area S of FIG. 7 since there is a problem, as will be described later, of reduction in SN occurring when detecting the reflected light from the interface between the raindrop 102 and the air because regular reflection from the inner wall surface of the windshield 101 is incident on the image pickup lens 41.

The above-mentioned range of being able to obtain the image pickup amount of light varies due to being influenced by the contact angle of the raindrop 102 and is a numerical range that is effective in particular in a case where the contact angle is 20 through 70 deg, in particular, less than or equal to 60 deg. By installing the light source 30 in such a manner that the angle of elevation θ will fall within the above-mentioned range, it is possible to take, as a blurred bright point such as that of FIG. 4, an image of the reflected light that includes regular reflection reflected by the interface between the raindrop 102 that has adhered to the outer wall surface of the windshield 101 and the air from the emitted light from the light source 30. It is noted that the contact angle means an angle between a tangential line of a raindrop 102 and the outer wall surface of the windshield 101.

It is noted that the setting angle (installing angle) of the light source 30 described above is one in a case of an angle of the emitted light of the light source 30 at which the light intensity has the peak from the angle distribution of the emitted light of the light source 30. The light beam of this angle to obtain the peak of light intensity will be referred to as a typical light beam.

What is to consider in the configuration of FIG. 6 is that there is the problem of reduction in SN when detecting the reflected light from the interface between the raindrop 102 and the air because of regular reflection from the inner wall surface of the windshield 101 being incident on the image pickup lens 41.

Figure 8:
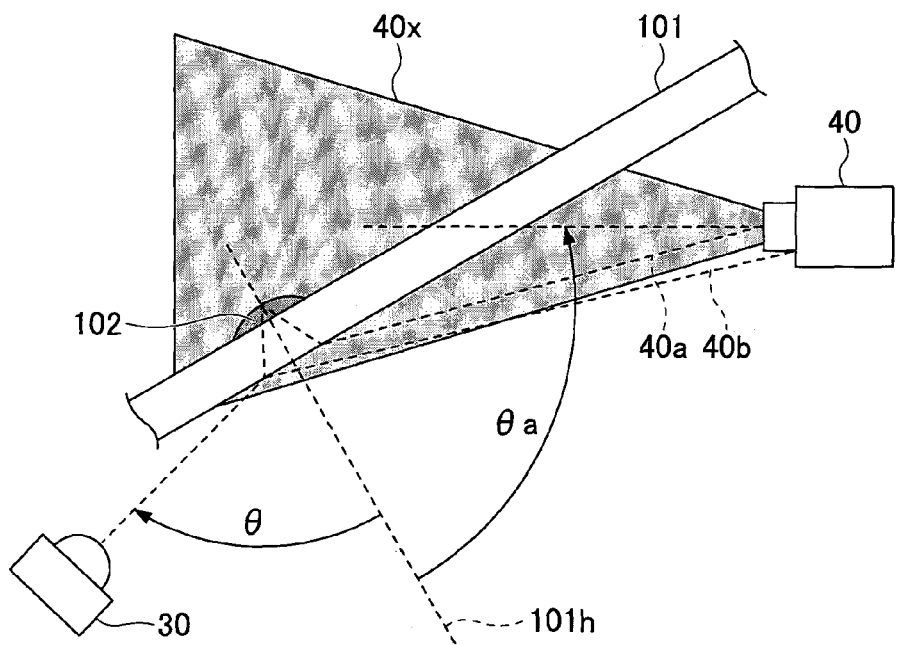
FIG. 8 shows a side view illustrating a problem of a reduction in SN.

This problem can be avoided by putting the image pickup device 40 in such a manner that, as shown in FIG. 8, the reflected light 40b (regular reflection) from the inner wall surface of the windshield 101 will be prevented from being incident on the image pickup lens 41 (not shown) of the image pickup device 40 (this state may be simply referred to as "frame out"). That is, by thus putting the image pickup device 40 in the above-mentioned manner, it is possible to avoid degradation of SN when detecting the reflected light 40a from the interface between the raindrop 102 and the air. It is noted that in FIG. 8, the reference numeral 40x denotes the range of the angle of view for image pickup of the image pickup device 40.

In a case of, as illustrated above, using a light source having a large diffusion angle such as a LED as the light source 30 or installing a condenser lens in the light source 30, there may be a case where a light element exceeding the angle range of FIG. 7 described above is generated. In such a case, the requirements for satisfying the above-mentioned "frame out" are to set the angle of elevation θ of the light that is emitted from the light source 30 and is incident on the windshield 101 to be less than θs. This incident light means a main element that includes not only the above-mentioned typical light beam but also an element greater than or equal to 95% of the element that reaches the windshield 101.

An effective method of satisfying these requirements is to reduce the diffusion angle of the light source 30 or, if such a method is not possible, to block the element that has the angle of elevation exceeding θs of the light that reaches the windshield 101 from the diffusion light that has been emitted by the light source 30. In this regard, description will now be specifically made using FIGS. 9A and 9B.

Figure 9A:
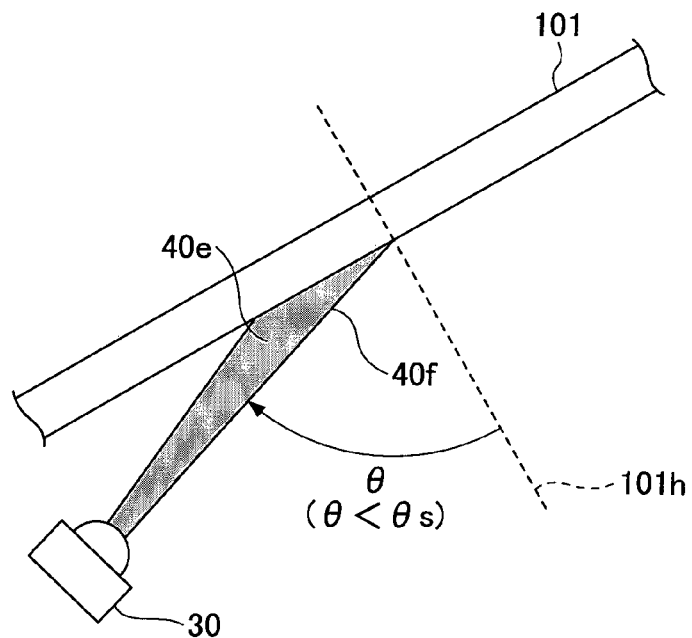
FIGS. 9A-9B show side views illustrating measures to solve the problem of a reduction in SN.
Figure 9B:
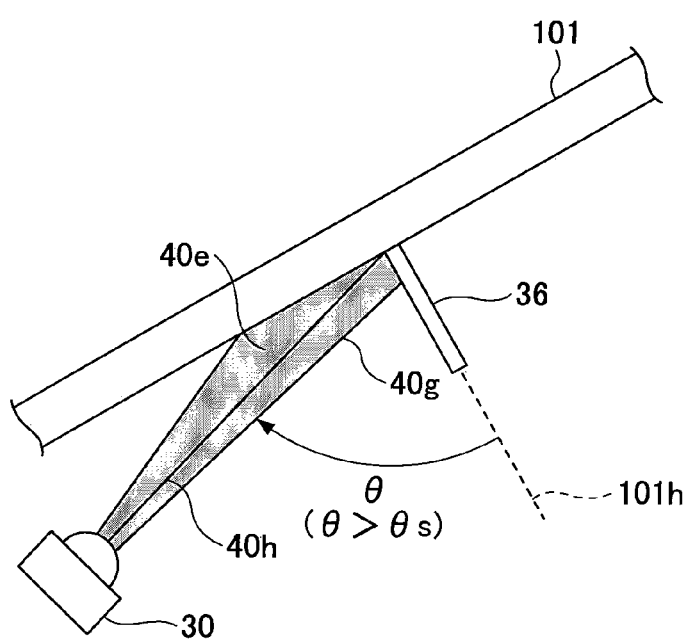

FIGS. 9A and 9B are side views illustrating measures of avoiding the problem of reduction of SN. FIG. 9A shows one example of reducing the diffusion angle of the light source 30. The reference numeral 40e denotes the diffusion light from the light source 30. By setting the incident angle θ on the windshield 101 of the light beam 40f having the largest diffusion angle from the diffusion light 40e to be less than θs, it is possible to reduce the light being incident on the image pickup lens 41 (not shown).

Further, as shown in FIG. 9B, in a case where the diffusion light from the light source 30 includes the light beam 40g having the large diffusion angle, a light blocking member 36 may be installed adjacent to the windshield 101. Thereby, the light beam 40g can be blocked and can be prevented from reaching the image pickup lens 41 (not shown). Thus, the element that is not blocked by the light blocking member 36 only includes the element that satisfying the requirements θ<θs as illustrated as the light beam 40h.

As a specific numerical example, in a case where the angle θs determined by the arrangement of the windshield 101, the light source 30 and the image pickup device 40 is 65 deg, ±10 deg as the diffusion angle of the emitted light of the light source 30 (for example, LED) and 50 deg as the incident angle of the typical light beam on the windshield 101 may be cited.

As another effective method, there is a method of emitting p-polarized light to the windshield 101. By emitting p-polarized light to the windshield 101, it is possible to reduce reflected light from the inner wall surface of the windshield 101. Thus, it is possible to prevent reduction of SN when detecting the reflected light from the interface between the raindrop 102 and the air.

Figure 10:
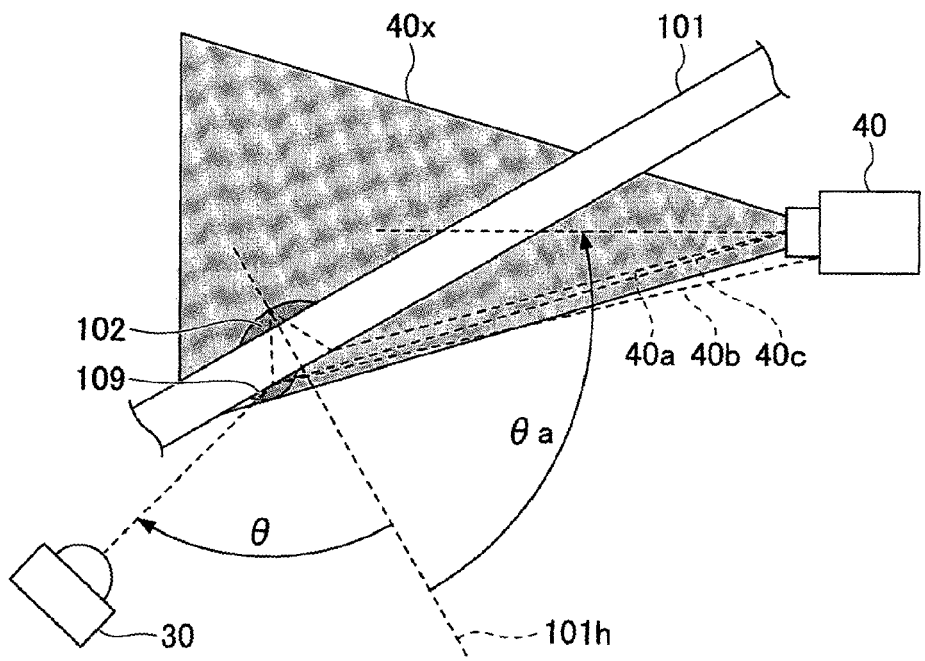
FIG. 10 shows a side view illustrating scattered light.

The reflected light from the inner wall surface of the windshield 101 may be actively used for detecting an object that adheres to the inner wall surface of the windshield 101. For example, the emitted light is scattered by an adhered object 109 and scattered light 40c is generated when light is emitted from the light source 30 to the adhered object 109 such as a fine waterdrop that has adhered to the inner wall surface of the windshield 101, as shown in FIG. 10.

Thus, the image pickup device 40 is put in such a manner that regular reflection from the inner wall surface of the windshield 101 will not be incident on the image pickup lens 41 (not shown) of the image pickup device 40 while the scattered light 40c from the adhered object 109 on the inner wall surface of the windshield 101 will be incident on the image pickup lens 41 (not shown) of the image pickup device 40. In other words, the position on the inner wall surface of the windshield 101 to which the light source 30 emits light is to be included in the effective image pickup area.

Figure 11:
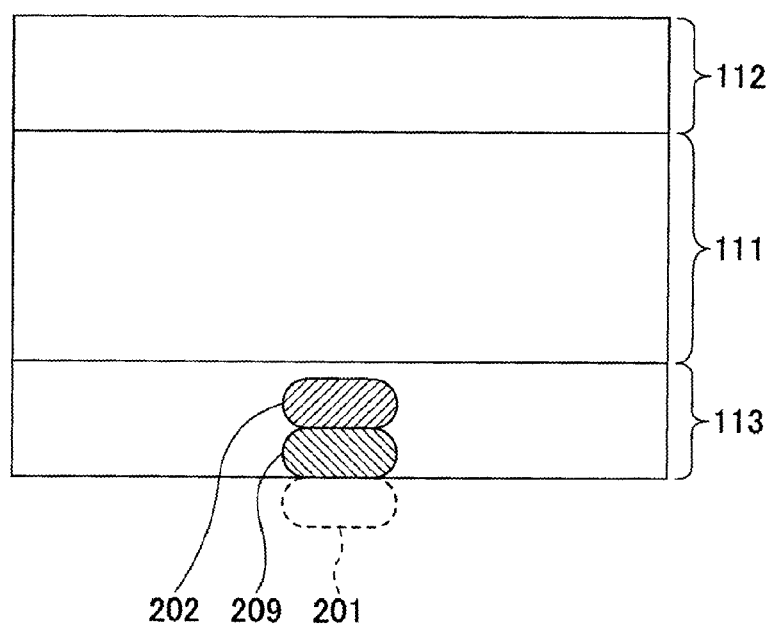
FIG. 11 illustrates optical spots, images of which are taken.

Thus, the scattered light 40c is incident on the image pickup lens 41 (not shown) of the image pickup device 40 and as shown in FIG. 11, an image of the scattered light 40c is taken as an optical spot 209. In many cases, the optical spot 209 is different in position from an optical spot 202 of the reflected light 40a from the interface between the raindrop 102 and the air and an optical spot 201 of the regular reflection from the inner wall surface of the windshield 101 in an image thus taken by the image pickup device 40.

As a result, it is possible to separately detect an adhered object on the inner wall surface of the windshield 101 from detection of an adhered object on the outer wall surface of the windshield 101 (raindrop detection). As a specific example of the adhered object on the inner wall surface of the windshield 101, mist, dew condensation or the like on the inner wall surface of the windshield 101 due to moisture in the vehicle may be cited. It is noted that in FIG. 11, the reference numeral 111 denotes a vehicle detection image area. The reference numerals 112 and 113 denote raindrop detection image areas (also described later using FIG. 41).

However, depending on the angle and/or the thickness of the windshield 101, the optical spot 202 and the optical spot 209 shown in FIG. 11 may overlap with one another. In such a case, it is useful to emit light that includes both of respective polarized elements, i.e., a p-polarized element and an s-polarized element to the windshield 101. The optical spot 202 is formed mainly by the p-polarized light as a main element and the optical spot 209 is formed mainly by the s-polarized light as a main element. Thus, it is possible to detect the optical spot 202 and the optical spot 209 separately by taking respective images of the p-polarized element and the s-polarized element.

In order to realize it, an image pickup device may be provided in which pixels that can detect a p-polarized element and an s-polarized element, respectively, are arranged repetitively in units each one including one or two pixels. Specifically, in front of the image sensor 43, polarization filter layers that transmit only the p-polarized element and polarization filter layers that transmit only the s-polarized element may be provided in such a manner that area separation is made in pixel units. The polarization filter layers that transmit only the p-polarized element will act as raindrop detection image areas. The polarization filter layers that transmit only the s-polarized element will act as inside mist detection image areas.

The respective polarization filter layers may be realized by, for example, wire grid polarizers. Specifically, the polarization filter layers that transmit only the p-polarized element and the polarization filter layers that transmit only the s-polarized element may be formed by, for example, adjusting groove directions of respective templates (corresponding to molds) to be used for patterning to form metal wires of the respective wire grid structures so that the transmission axes (grid axis directions) thereof will cross at right angles.

Figure 12:
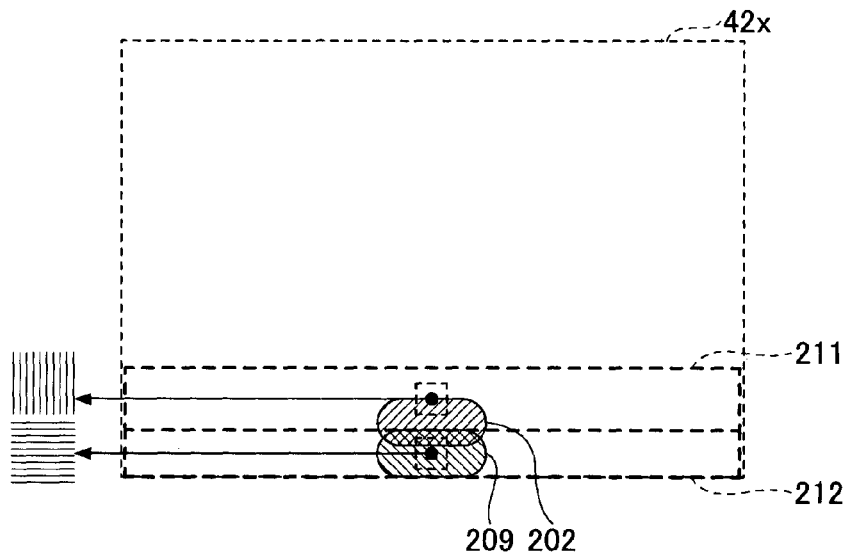
FIG. 12 illustrates a polarization filter layer.

Alternatively, instead of the above-mentioned pixel-unit area-separated polarization filter layers, a configuration such as that shown in FIG. 12 may be used. In the configuration of FIG. 12, in the effective image pickup area 42x of the optical filter 42, a p-polarized light detection area 211 and an s-polarized light detection area 212 are arranged one above the other. The p-polarized light detection area 211 will act as the raindrop detection image area. The s-polarized light detection area 212 will act as the inside mist detection image area.

The p-polarized light detection area 211 and the s-polarized light detection area 212 may be provided as a result of having, for example, in front of the image sensor 43, a polarization filter layer that only transmits a p-polarized element and a polarization filter layer that only transmits an s-polarized element formed to be adjacent to one another one above the other. A specific method of forming the polarization filter layer that only transmits the p-polarized element and the polarization filter layer that only transmits the s-polarized element may be the same as that described above.

Using FIG. 6 and so forth, the arrangements of the light source 30 and the image pickup device 40 which are effective in a case where the contact angle of the raindrop 102 is less than or equal to 60 deg have been described. Below, arrangements of the light source 30 and the image pickup device 40 will be described which are effective in a case where the contact angle of the raindrop 102 is greater than or equal to 60 deg.

Figure 13:
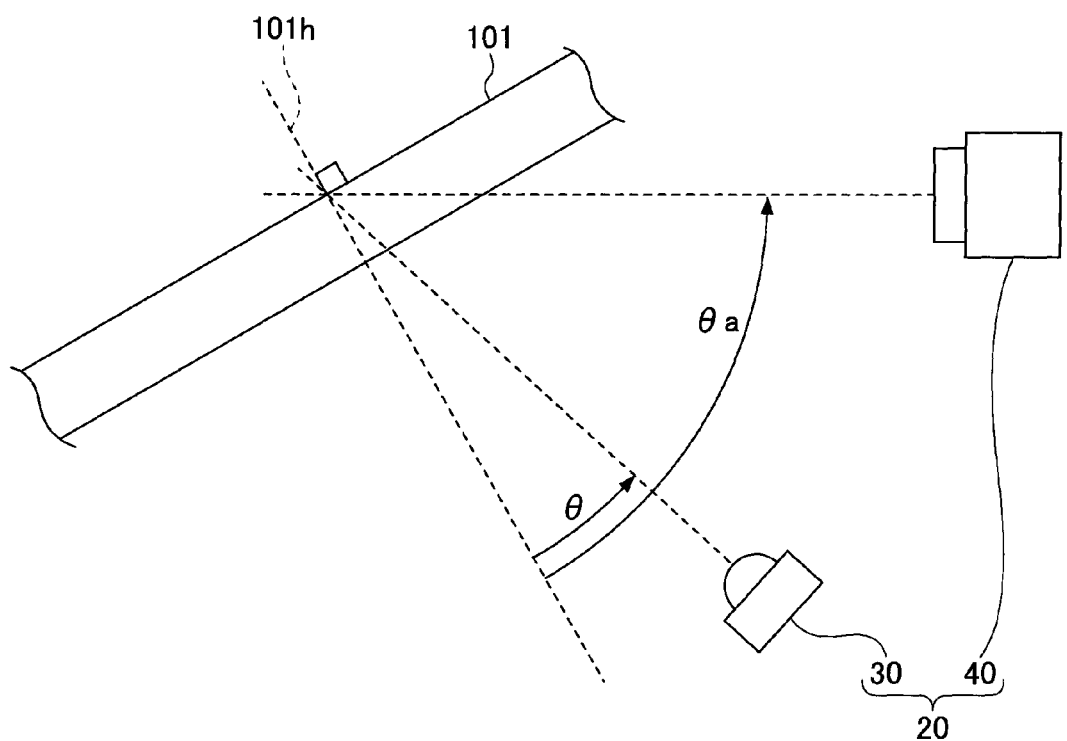
FIG. 13 illustrates another arrangement of the light source 30 and the image pickup device 40.

FIG. 13 illustrates an arrangement of the light source 30 and the image pickup device 40. In FIG. 13, the same as FIG. 6, the light source 30 and the image pickup lens 41 (not shown) of the image pickup device 40 are arranged horizontally and the angle of elevation of the image pickup lens 41

(not shown) with respect to the normal 101*h* of the windshield 101 that intersects the optical axis of the image pickup lens 41 (not shown) is θa.

Further, the same as FIG. 6, the angle of elevation of the light source 30 with respect to the normal 101*h* of the windshield 101 that intersects the optical axis of the image pickup lens 41 (not shown) is θ. Thus, light from the light source 30 is incident on the windshield 101 at the angle of elevation θ. In other words, the incident angle of vertical direction of the light emitted by the light source 30 on the windshield 101 is θ. The angle of elevation θ (the incident angle θ of vertical direction of the emitted light from the light source 30 on the windshield 101) is set in the range "θa−50 deg<θ<θa+20 deg". It is noted that in FIG. 13, the clockwise direction is a − direction and the counterclockwise direction is a + direction.

Figure 14:
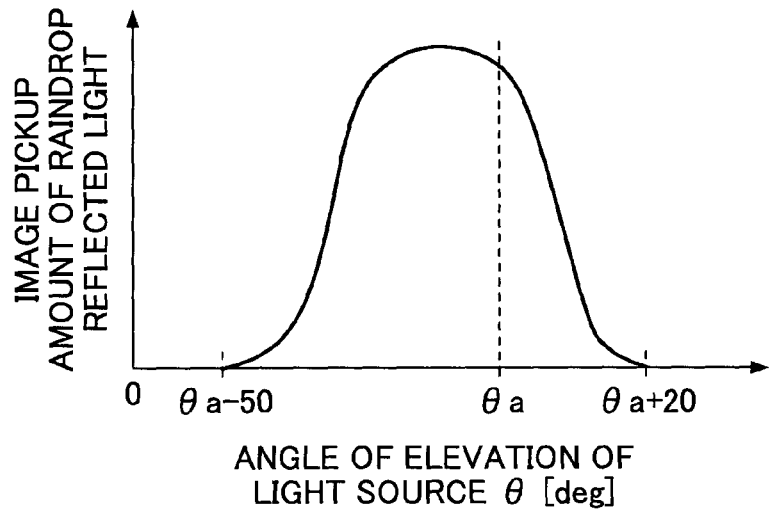
FIG. 14 illustrates another relationship between the angle of elevation θ of the light source 30 and the image pickup amount of reflected light.

FIG. 14 illustrates a relationship between the angle of elevation θ of the light source 30 and the image pickup amount of light of the reflected light. FIG. 14 shows the relationship derived through study by the inventors and so forth. As shown in FIG. 14, the image pickup amount of light of the reflected light from the interface between the raindrop 102 and the air from the emitted light of the light source 30 has the maximum value at the angle of elevation θ of the light source 30 being around the angle of elevation θa of the image pickup device 40 or a value slightly lower than the angle of elevation θa of the image pickup device 40. The image pickup amount of light can be obtained in a range "θa−50 deg<θ<θa+20 deg".

The above-mentioned range of being able to obtain the image pickup amount of light varies as being influenced by the contact angle of the raindrop 102 and is a numerical range that is effective in particular in a case where the contact angle is greater than or equal to 60 deg. By installing the light source 30 in such a manner that the angle of elevation θ will fall within the above-mentioned range, it is possible to take, as a blurred bright point such as that of FIG. 4, an image of the reflected light reflected by the interface between the raindrop 102 that has adhered to the outer wall surface of the windshield 101 and the air from the emitted light of the light source 30.

Figure 15:
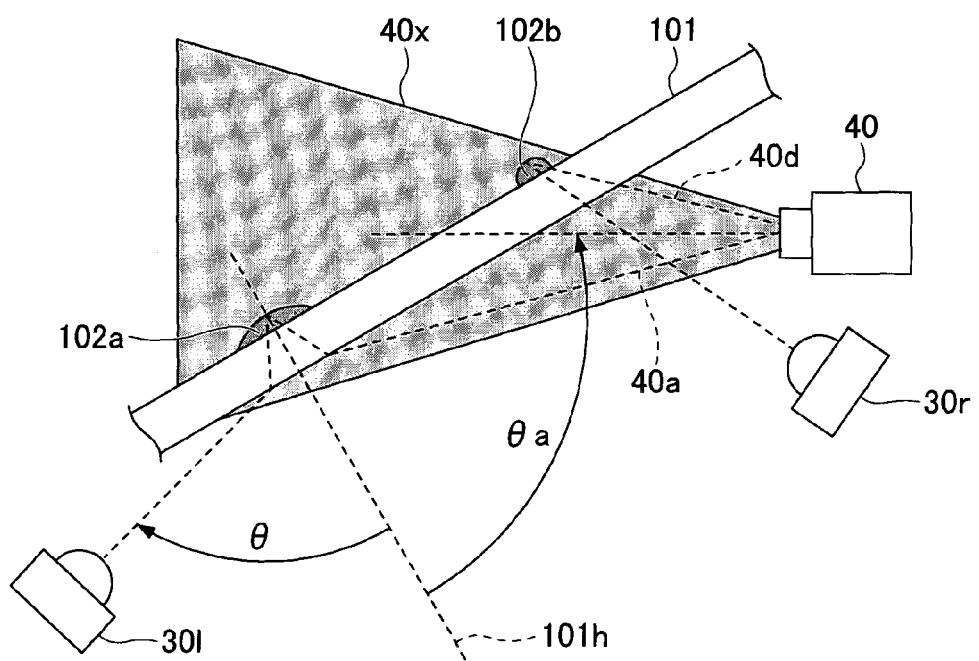
FIG. 15 shows a side view illustrating an example using both the respective arrangements of the light source 30 and the image pickup device 40 of FIGS. 6 and 13.

FIG. 15 is a side view illustrating an example that uses both the arrangements of the light source 30 and the image pickup device 40 shown in FIGS. 6 and 13. In FIG. 15, a light source 30*l* is put at a position corresponding to FIG. 6. A light source 30*r* is put at a position corresponding to FIG. 13.

The light source 30*l* emits light to an area of the windshield 101 corresponding to a lower end part of the range 40*x* of the angle of view for image pickup of the image pickup device 40, the emitted light is reflected by the interface between a raindrop 102*a* and the air, and the reflected light 40*a* including regular reflection of the emitted light of the light source 30*l* is incident on the image pickup device 40. The light source 30*r* emits light to an area of the windshield 101 corresponding to an upper end part of the range 40*x* of the angle of view for image pickup of the image pickup device 40, the emitted light is reflected by the interface between a raindrop 102*b* and the air, and the reflected light 40*d* is incident on the image pickup device 40.

Figure 16:
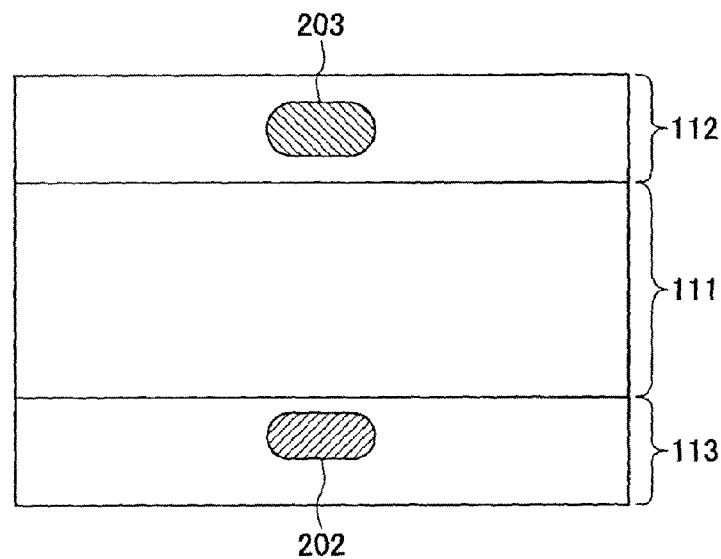
FIG. 16 illustrates optical spots, images of which are taken.

The reflected light 40*a* incident on the image pickup device 40 forms an optical spot 202 in a raindrop detection image area 113 in the lower end part of an image, as shown in FIG. 16. The reflected light 40*d* incident on the image pickup device 40 forms an optical spot 203 in a raindrop detection image area 112 in the upper end part of the image, as shown in FIG. 16.

By using the optical spot 202 in the raindrop detection image area 113, it is possible to detect a raindrop having the smaller contact angle (for example, less than or equal to 60 deg). By using the optical spot 203 in the raindrop detection image area 112, it is possible to detect a raindrop having the larger contact angle (for example, greater than or equal to 60 deg). Thus, by arranging the plural light sources (for example, the light sources 30*l* and 30*r*) having the different positional relationships with respect to the image pickup device 40, it is possible to detect raindrops having the respective contact angle ranges suitable for the respective positions. Thus, it is possible to detect raindrops with high sensitivity without regard to the contact angles of the raindrops.

Figure 17:
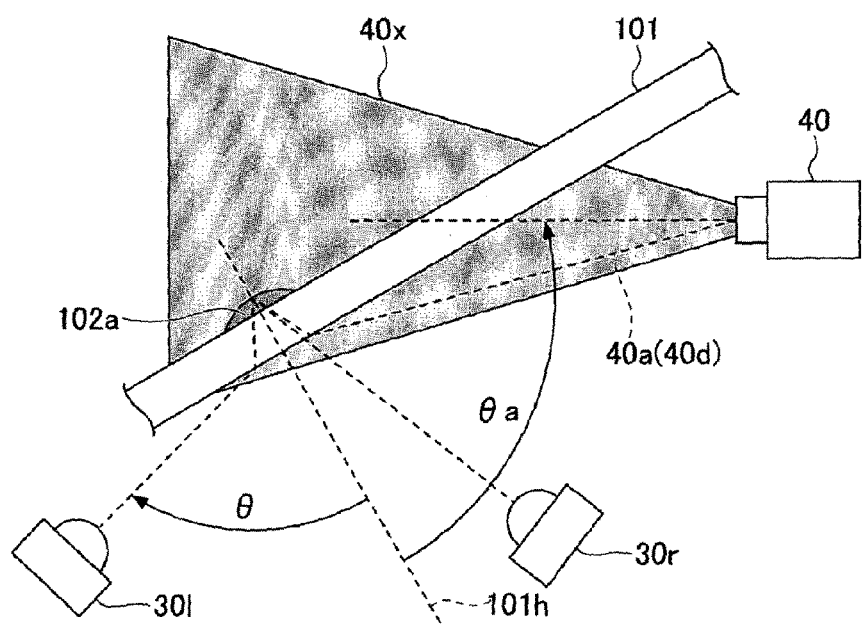
FIG. 17 shows a side view illustrating yet another arrangement of the light source 30 and the image pickup device 40.
Figure 18:
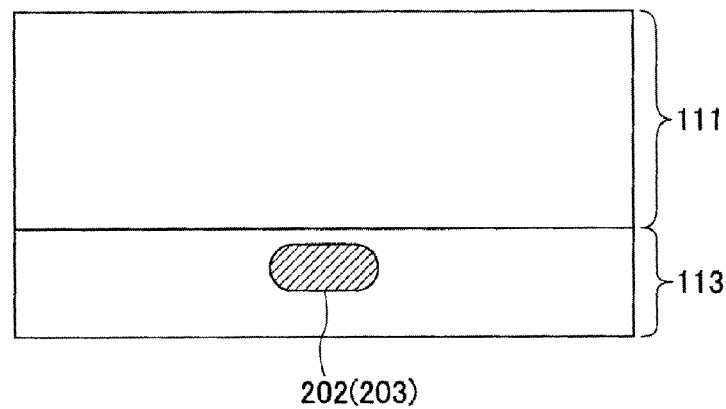
FIG. 18 illustrates an optical spot, an image of which is taken.

It is noted that in FIG. 16, the positions to which the light sources 30*l* and 30*r* emit light, respectively, are the areas of the windshield 101 corresponding to the lower end part and the upper end part of the range 40*x* of the angle of view for image pickup of the image pickup device 40, respectively. However, it is also possible to provide a configuration in which, as shown in FIG. 17, the light sources 30*l* and 30*r* emit light to the same position, respectively. In the case of FIG. 17, optical spots 202 and 203 are formed in a raindrop detection image area 113 at a lower end part of the image, as shown in FIG. 18.

Further, in FIGS. 15 and 17, the examples are shown of using the two light sources 30*l* and 30*r* for emitting light to the windshield 101 from the two different placement angles. However, it is also possible to use branched sets of light originally emitted from the single light source.

Figure 19:
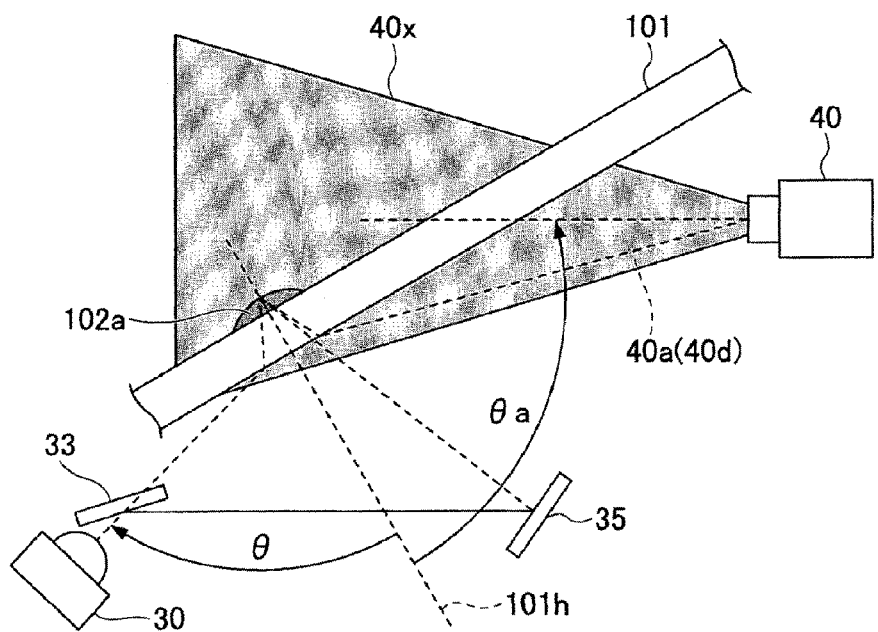
FIG. 19 shows a side view illustrating a configuration of emitting plural beams of light from the single light source 30 to a windshield 101.

FIG. 19 shows a side view illustrating a configuration of emitting light to the windshield 101 with plural sets of light from the single light source 30. In FIG. 19, the emitted light from the light source 30 is divided by a beam splitter 33 into respective sets of light that travel in two directions. One set of light travels straight through the beam splitter 33 and is incident on the windshield 101 in the same optical path as that of the emitted light of the light source 30*l* of FIG. 17.

The other set of light is obtained from being branched by the beam splitter 33, is incident on a turning mirror 35, is reflected by the turning mirror 35 and is incident on the windshield 101 in the same optical path as that of the emitted light of the light source 30*r* of FIG. 17. Thus, it is possible to emit the plural sets of light originally emitted from the single light source 30 to the windshield 101.

Figure 20:
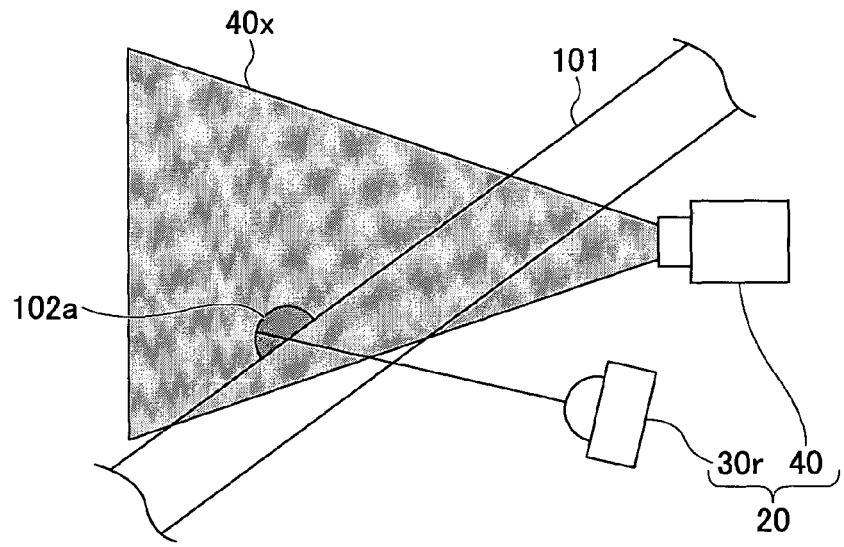
FIG. 20 shows a side view illustrating a placement of the light source 30 in consideration of the angle of view of the image pickup device 40.
Figure 21:
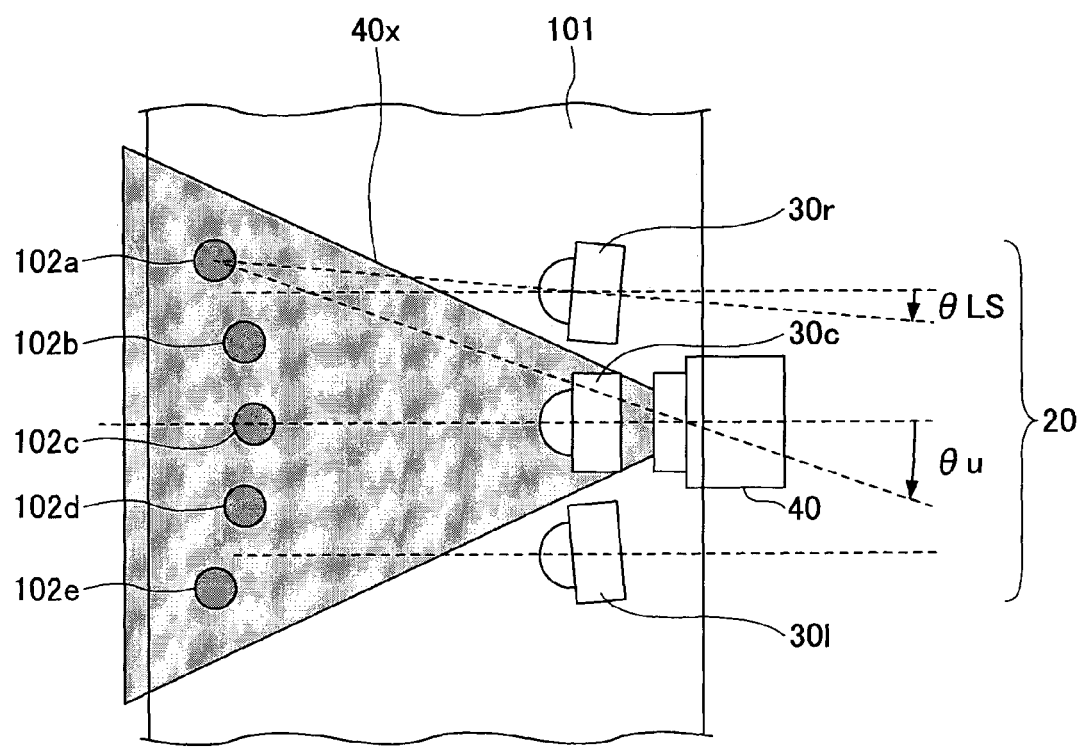
FIG. 21 shows a plan view illustrating the placement of the light source 30 in consideration of the angle of view of the image pickup device 40.

FIG. 20 shows a side view illustrating a placement of the light source 30 in consideration of the angle of view of the image pickup device 40. FIG. 21 shows a plan view illustrating the placement of the light source 30 in consideration of the angle of view of the image pickup device 40. It is noted that FIGS. 20 and 21 shows an example of arranging three light sources 30*r*, 30*c* and 30*l*. It is noted that in FIGS. 20 and 21, the reference numeral 40*x* denotes the range of the angle of view for image pickup of the image pickup device 40.

In FIGS. 20 and 21, the emitted light from the light source 30*r* is emitted to a raindrop 102*a*, and an image thereof is taken by the image pickup device 40. At this time, the emitting angle θLS of the light source 30*r* (the incident angle θLS of horizontal direction of the light emitted by the light source 30*r* on the windshield 101) with respect to the angle of view θu for image pickup of the raindrop 102*a* is set in the range "θu−20 deg<θLS<θu+20 deg".

In other words, the light source 30*r* is put in such a manner that in a case where the angle of view for image pickup of the raindrop 102*a* is θu, the incident angle of horizontal direction of the emitted light from the light source 30*r* on the windshield 101 falls within the range "θu−20 deg through θu+20 deg". Thus, it is possible to carry out taking an image by detecting the reflected light from the interface between the raindrop 102 and the air with high efficiency. It is noted that in FIG. 21, the clockwise direction is a − direction and the counterclockwise direction is a + direction.

It is noted that it is also possible to set the emitting angle θLS of the light source 30r (the incident angle θLS of horizontal direction of the light emitted by the light source 30r on the windshield 101) in the range "θu−20 deg<θLS<θu+20 deg" and also set the angle of elevation θ of the light source 30r (the incident angle θ of vertical direction of the emitted light from the light source 30r on the windshield 101) in the range "θa−50 deg<θ<θa+20 deg".

Figure 22:
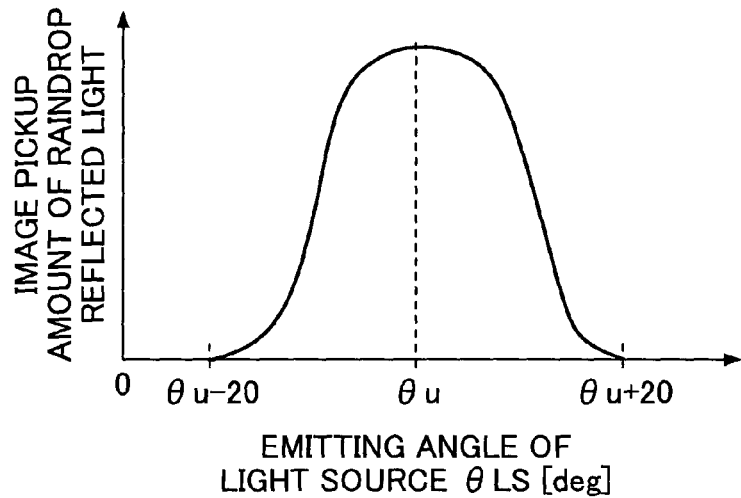
FIG. 22 illustrates a relationship between an emitting angle θLS of the light source 30 and an image pickup amount of reflected light.

FIG. 22 illustrates the relationships between the emitting angle θLS of the light source 30 and the image pickup amount of light of the reflected light. FIG. 22 shows the relationships derived from study of the inventors and so forth. As shown in FIG. 22, from the emitted light of the light source 30, the image pickup amount of light of the reflected light from the interface between the raindrop 102 and the air has the maximum value in a case where the emitting angle θLS is coincident with the angle of view for image pickup θu or is near the angle of view for image pickup θu. The image pickup amount of light can be obtained in the range "θu−20 deg<θLS<θu+20 deg".

The above-mentioned range of being able to obtain the image pickup amount of light varies as being influenced by the contact angle of the raindrop 102 and is a numerical range that is effective in particular in a case where the contact angle is greater than or equal to 60 deg. By installing the light source 30 in such a manner that the incident angle θLS from the light source 30 will fall within the above-mentioned range, it is possible to take, as a blurred bright point such as that of FIG. 4, an image of the reflected light reflected by the interface between the raindrop 102 that has adhered to the outer wall surface of the windshield 101 and the air from the emitted light of the light source 30.

Figure 23:
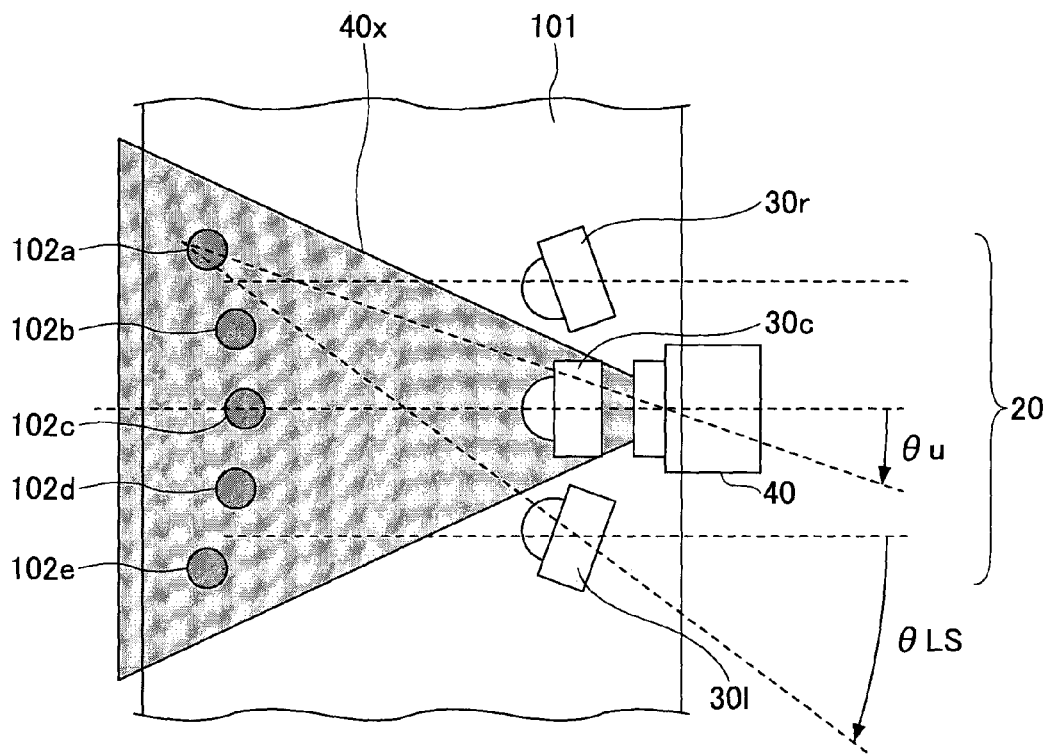
FIG. 23 shows another plan view illustrating a placement of the light source 30 in consideration of the angle of view of the image pickup device 40.

It is noted that for the plural light sources 30r, 30c and 30l of FIG. 21, it is also possible to arrange them in such a manner that the light beams thereof intersect each other as shown in FIG. 23 as long as the above-mentioned range is satisfied.

Figure 24:
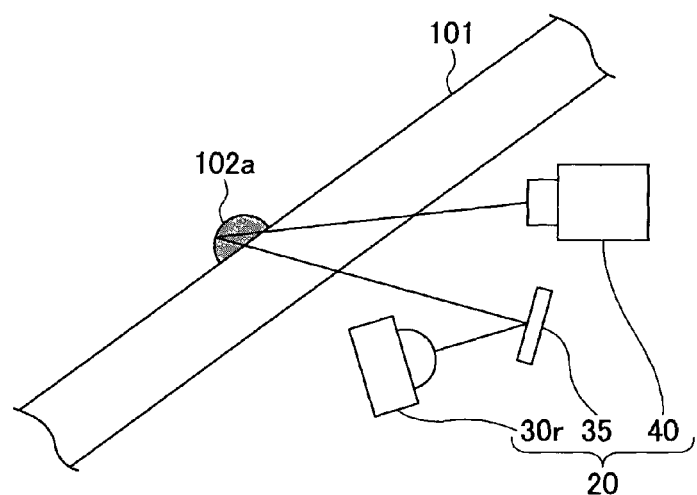
FIG. 24 shows a side view illustrating an example of providing a turning mirror 35.

Further, as to the emitting direction of the light source, it is not necessary to point toward the inner wall surface of the windshield 101 as indicated above. For example, as shown in FIG. 24, it is possible that the light source 30r itself is put in a manner of not pointing toward the inner wall surface of the windshield 101 and a turning mirror 35 for changing an optical path so that the emitted light will be then emitted toward the windshield 101 is provided on the optical path of the emitted light from the light source 30r. By providing the turning mirror 35, it is possible to contribute to improvement of freedom of placement of the light source 30r and miniaturization of the image pickup unit 20.

[Configuration of Optical Filter]

Figure 25:
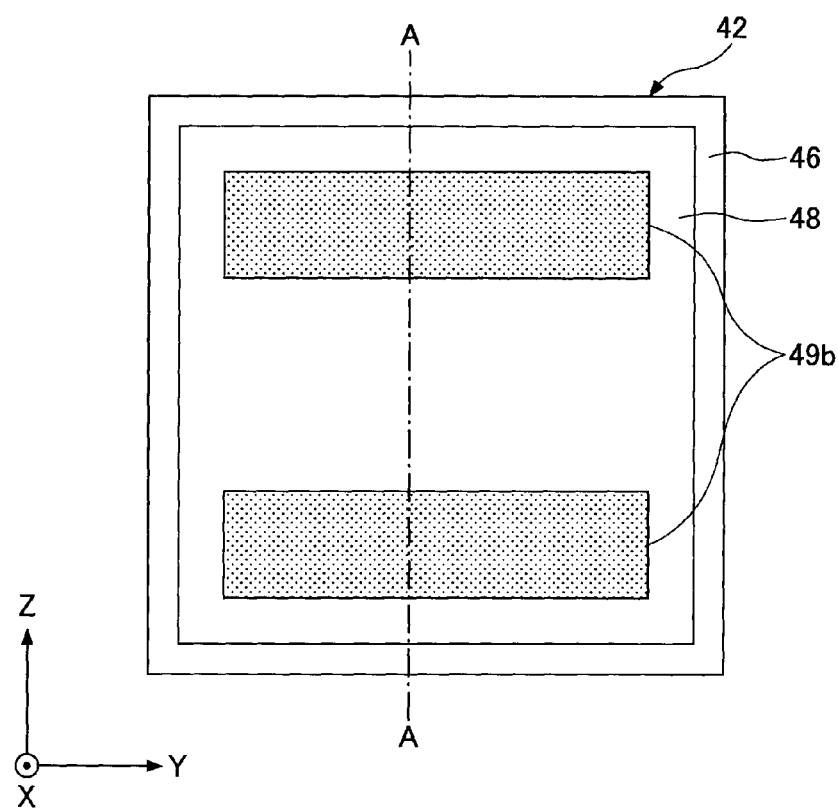
FIG. 25 shows a view of an optical filter 42 viewed from the side of a sensor substrate 44.
Figure 26:
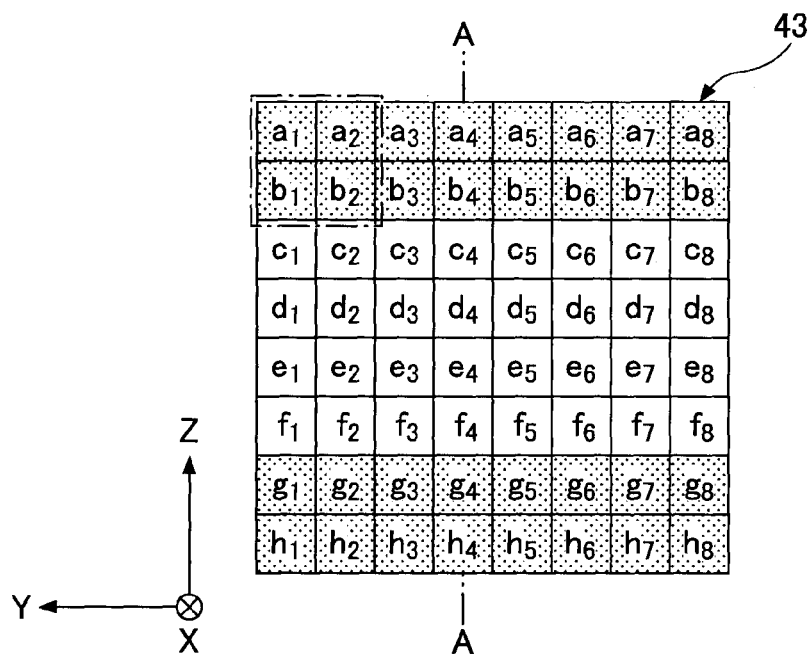
FIG. 26 shows a view of a surface of an image sensor 43 opposite to the optical filter 42 viewed in a see-through manner from the side of the sensor substrate 44.
Figure 27:
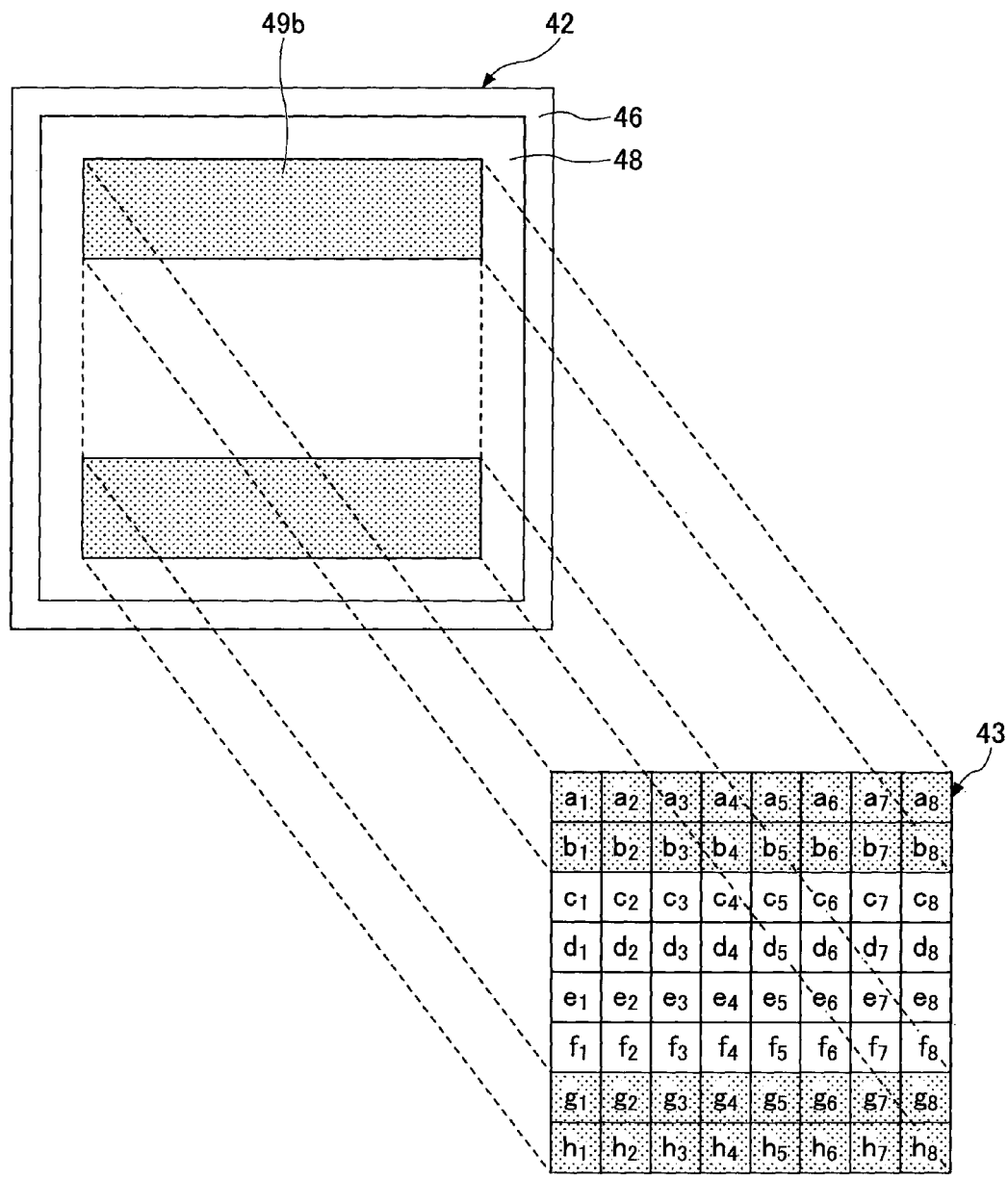
FIG. 27 illustrates a correspondence of positional relationship between the optical filter 42 and the image sensor 43 according to the first embodiment.
Figure 28:
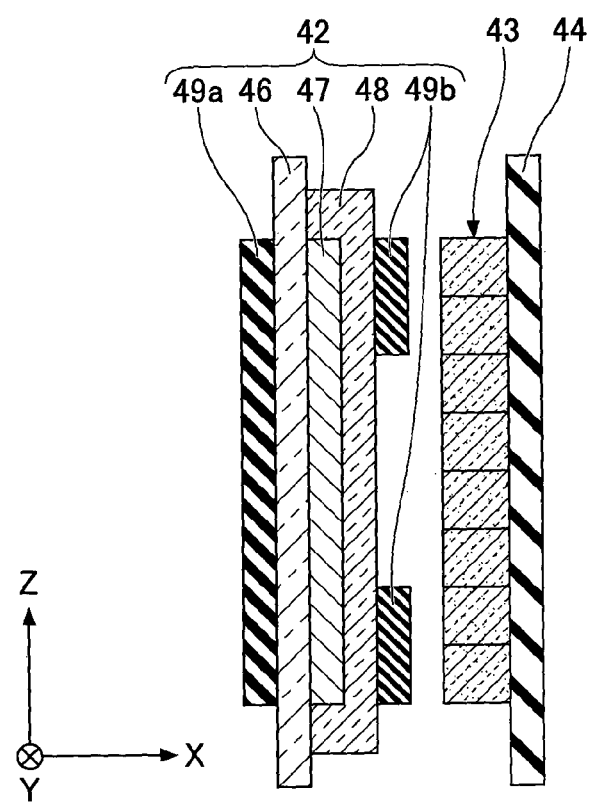
FIG. 28 shows a sectional view taken along an A-A line of FIGS. 25 and 26.

FIG. 25 shows a view of the optical filter 42 viewed from the side of the sensor substrate 44. FIG. 26 shows a view of the surface of the image sensor 43 opposite to the optical filter 42 viewed from the side of the sensor substrate 44 in a see-through manner. FIG. 27 illustrates a correspondence of a positional relationship between the optical filter 42 and the image sensor 43 according to the first embodiment. FIG. 28 shows a sectional view taken along the A-A line of FIG. 25 and FIG. 26.

It is noted that in FIGS. 25 through 27, for the sake of convenience, spectral filter layers 49b and the areas of the image sensor 43 corresponding to the spectral filter layers 49b are filled with dots. Further, in the optical filter 42 shown in FIG. 27, broken lines drawn along the periphery of the spectral filter layers 49b indicate the effective image pickup area.

As shown in FIGS. 25 through 28, in the optical filter 42, a filter substrate 46 is a transparent substrate that transmits incident light that is incident on the optical filter 42 via the image pickup lens 41. A spectral filter layer 49a is formed on the entirety of an effective image area (the area corresponding to all the pixels included in the image sensor 43) on the surface of the filter substrate 46 on the side of the image pickup lens 41.

Further, on the surface of the filter substrate 46 on the side of the image sensor 43, a polarization filter layer 47 is formed. It may not be necessary for the polarization filter layer 47 to be formed. However, by forming the polarization filter layer 47, it is possible to reduce unnecessary light, and thus, it is possible to improve detection accuracy of raindrop detection and vehicle detection.

Further a packing member 48 is formed to cover the polarization filter layer 47. Further, the spectral filter layers 49b are laminated and formed at an upper end part and a lower end part of the effective image area on the surface of the packing member 48 on the side of the image sensor 43. It is noted that the spectral filter layers 49b are typical examples of a spectral filter layer.

From the light incident on the optical filter 42, the light that has passed through the spectral filter layer 49a, the polarization filter layer 47 and the spectral filter layers 49b is incident on the pixels $43a_1$ through $43b_8$ and $43g_1$ through $43h_8$ (see FIG. 27). From the light incident on the optical filter 42, the light that has passed through the spectral filter layer 49a and the polarization filter layer 47 (the light that has passed through the area in which the spectral filter layers 49b are not formed) is incident on the pixels $43c_1$ through $43f_8$ (see FIG. 27).

As the material of the filter substrate 46, a material that can transmit light of an operating band (according to the first embodiment, the visible light range and the infrared range) may be used, for example, glass, sapphire, quartz or the like. According to the first embodiment, glass, in particular, quartz glass (refractive index: 1.46) or TEMPAX glass (refractive index: 1.51), any of which is cheap and durable, is suitable for being used.

Figure 29:
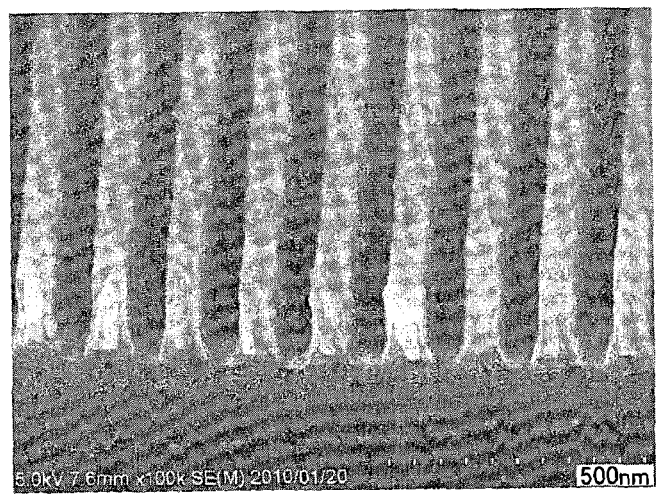
FIG. 29 illustrates a polarizer formed to have a wire grid structure.

The polarization filter layer 47 is formed to only transmit the p-polarized element of the light incident on the optical filter 42. The polarization filter layer 47 has a polarizer formed to have a wire grid structure such as that shown in FIG. 29 and the surface on the side of the spectral filter layers 49b is an uneven surface. The wire grid structure is a structure in which metal wires (electrically conductive lines) made of a metal such as aluminium, which extend in a specific direction, are arranged at a specific pitch. In the configuration of FIG. 29, the optical filter 42 blocks light when the light having the polarization direction of the groove direction is incident. When light having the polarization direction perpendicular to the groove direction is incident, the optical filter 42 transmits the light.

By determining the wire pitch of the wire grid-structure to be, in comparison to the wavelength range of incident light (for example, wavelengths of 400 nm through 800 nm of visible light), a sufficiently smaller pitch (for example, ½ or less thereof), the following advantages are obtained. That is, light of an electric field vector element that oscillates parallel to the longitudinal direction of the metal wires is mostly reflected. Light of an electric field vector element that oscillates perpendicular to the longitudinal direction of the metal wires is mostly transmitted. Thus, it can be used as a polarizer which generates single-polarization polarized light.

Generally speaking, in a polarizer having a wire grid structure, when the sectional area of the metal wires is increased, the extinction ratio is increased. Further, in the metal wires of predetermined width or greater with respect to the period width, the transmittance is reduced. Further, when the sectional shape perpendicular to the longitudinal direction of the metal wires is a taper shape, the wavelength dispersion property of the transmittance and the degree of polarization is small for a wide band and the high extinction ratio characteristic is obtained.

By forming-the-polarization filter layer 47 to have the wire grid structure, the following advantages can be obtained. That is, the wire grid structure can be formed using a well known semiconductor manufacturing process. Specifically, after an aluminium film has been evaporated on the filter substrate 46, patterning may be carried out, and a wire-grid subwavelength uneven structure may be formed by a method such as metal etching. By such a manufacturing process, it is possible to adjust the longitudinal direction of the metal wires, i.e., the polarization direction (polarization axis) on the order of the image pickup pixel size of the image sensor 43 (on the order of several μm).

Further, the wire grid structure is made of a metal material such as aluminium. Thus, it is superior in heat resistance and can be suitably used under high temperature environments such as the inside of a vehicle cabin which is likely to have high temperature.

When the spectral filter layers 49b are directly formed on the uneven surface of the polarization filter layer 47, the spectral filter layers 49b are formed along the uneven surface of the polarization filter layer 47; layer thickness unevenness may occur in the spectral filter layers 49b and it may not be possible to obtain the normal spectral performance. In order to avoid such a situation, the packing member 48 is used to fill the upper surface side in the laminating direction of the polarization filter layer 47 to make it flat. After that, the spectral filter layers 49b are formed on the packing member 48.

The packing member 48 is used to fill the depressed parts between the metal wires of the polarization filter layer 47. As the packing member 48, an inorganic material having the refractive index lower or equal to the refractive index of the filter substrate 46 may be suitably used. It is noted that the packing member 48 according to the first embodiment is formed also to cover the top surfaces in the laminating direction of the metal wires of the polarization filter layer 47.

As for the material of the packing member 48, it is necessary to make the uneven surface of the polarization filter layer 47 flat and not to interfere with the function of the polarization filter layer 47. Thus, it is preferable to use a material that does not have a polarization function. Further, as the material of the packing member 48, it is preferable to use a low refractive index material having the refractive index that is as close to that of the air (the refractive index: 1) as possible.

As the specific material of the packing member 48, for example, a porous ceramic material in which fine holes are dispersed in ceramics is preferable. In more detail, porous silica ($SiO_2$), porous magnesium fluoride (MgF), porous alumina ($Al_2O_3$) or the like may be cited.

Further, the degree of low refractive index thereof is determined by the number and/or size of the holes dispersed in ceramics (porous degree). In a case where the primary constituent of the filter substrate 46 is quartz, glass or the like, porous silica (n=1.22 through 1.26) may be suitably used.

As a method of forming the packing member 48, it is not necessary to be limited to these methods. For example, a Spin On Glass (SOG) method may be suitably used. Specifically, a solution in which silanol ($Si(OH)_4$) is dissolved in alcohol is used for spin coating to be carried out on the polarization filter layer 47 that has been formed on the filter substrate 46. After that, the solvent component is volatilized through heat treatment, and dehydration and polymerization reaction of the silanol itself is made to occur. Thus, the packing member 48 is formed.

The polarization filter layer 47 has the wire grid structure of the subwavelength size, mechanical strength thereof is not high, and the metal wires may be damaged by slight external force. The optical filter 42 according to the first embodiment is desired to be put close to the image sensor 43. Thus, during the manufacturing stage, the optical filter 42 and the image sensor 43 may come into contact with one another.

According to the first embodiment, the top surface in the laminating direction of the polarization filter layer 47 (the surface on the side of the image sensor 43) is covered by the packing member 48. Thus, it is possible to prevent the wire grid structure from being damaged if coming into contact with the image sensor 43. Further, by filling the depressed parts between the metal wires in the wire grid structure of the polarization filter layer 47 with the packing member 48, it is possible to prevent foreign objects from entering the depressed parts.

It is noted that the spectral filter layers 49b that are laminated on the packing member 48 may also be covered by a protective layer like the packing member 48. However, according to the first embodiment, no protective layer like the packing member 48 is provided for the spectral filter layers 49b. This is because, according to an experiment of the inventors and so forth, no such damage able to influence a pickup image occurred although the spectral filter layers 49b came into contact with the image sensor 43. Thus the protective layer is omitted as a result of placing priority on reducing the cost.

Further, although the height of the metal wires (projected parts) of the polarization filter layer 47 is low and less than or equal to the operating wavelength, the spectral filter layers 49b have the height equal to through on the order of several times the operating wavelength. As the thickness of the packing member 48 is increased, it becomes more difficult to ensure flatness of the top surface thereof, and thus the characteristics of the optical filter 42 may be influenced. Thus, there are limitations to increasing the thickness of the packing member 48. Thus, according to the first embodiment, the spectral filter layers 49b are not covered by a packing member.

Figure 30:
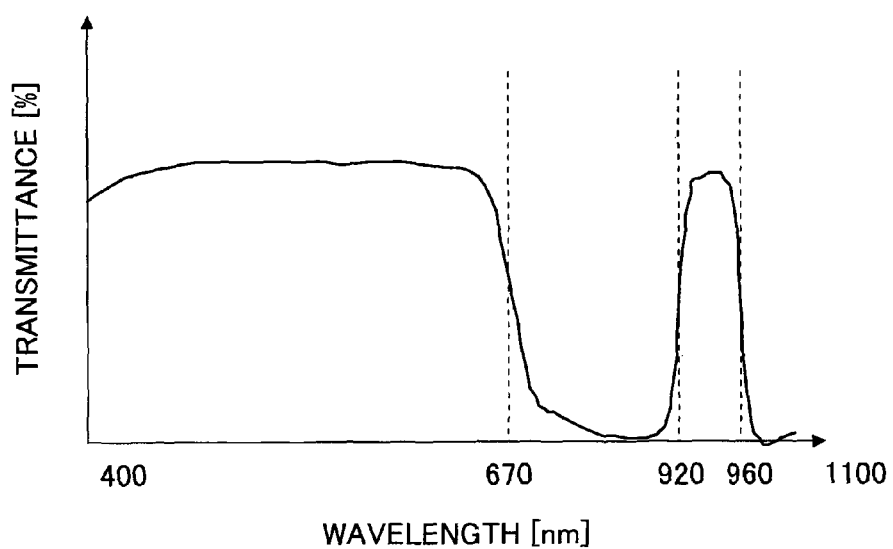
Figure 31:
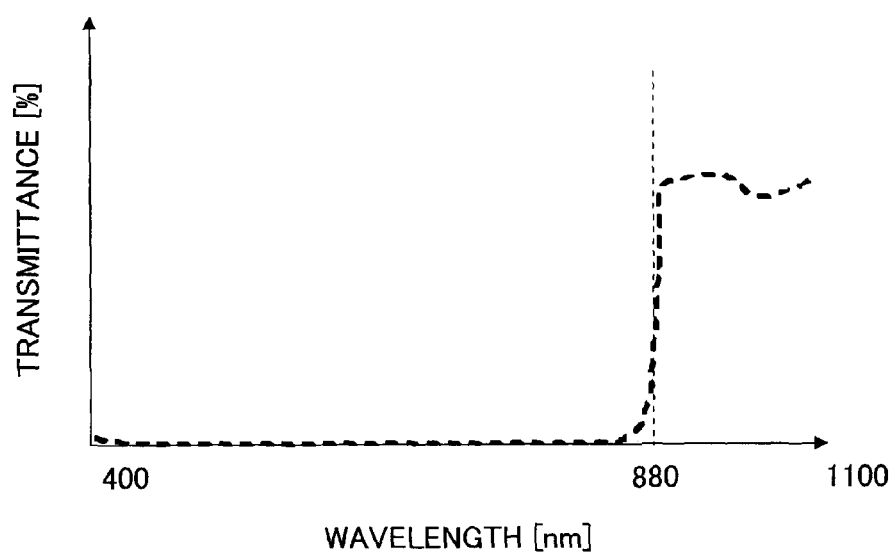
FIG. 31 illustrates transmittance characteristics of spectral filter layers 49b.

The transmittance characteristics of the spectral filter layers 49a and 49b will now be described. FIG. 30 illustrates the transmittance characteristics of the spectral filter layer 49a. FIG. 31 illustrates the transmittance characteristics of the spectral filter layers 49b.

As shown in FIG. 30, the spectral filter layer 49a has the transmittance characteristics of transmitting incident light of a so-called visible light area of a wavelength range $\lambda 1=400$ nm through $\lambda 2=670$ nm and incident light of a so-called infrared light area of a wavelength range $\lambda 3=920$ nm through $\lambda 4=960$ nm; and cutting incident light of a wavelength range $\lambda 2=670$ nm through $\lambda 3=920$ nm. It is noted that according to the first embodiment, the center wavelength of the light source 30 for raindrop detection is 940 nm and the full width at half maximum is 10 nm.

The transmittance for the wavelength range $\lambda 1=400$ nm through $\lambda 2=670$ nm and the wavelength range $\lambda 3=920$ nm through $\lambda 4=960$ nm may be preferably greater than or equal to 30%, and more preferably greater than or equal to 90%. The transmittance for the wavelength range $\lambda 2=670$ nm through $\lambda 3=920$ nm may be preferably less than or equal to 5%, and more preferably 0%.

Incident light of the visible light area is used to detect vehicle surrounding information and incident light of the infrared light area is used to detect raindrop information. The reason why incident light of the wavelength range $\lambda 2=670$ nm through $\lambda 3=920$ nm is not transmitted is that if the wavelength range were taken in, an obtained image would be red as a whole, and it might be difficult to extract a part indicating a red color of a taillight or the like.

By thus forming the filter having the characteristics of cutting most of the infrared light area ($\lambda 2=670$ nm through $\lambda 3=920$ nm) as shown in FIG. 30, it is possible to remove disturbance light, and thus it is possible to improve, for example, the detection accuracy of a taillight.

From the viewpoint of removing disturbance light, it is also preferable not to transmit the wavelength range of the light source 30 $\lambda 3=920$ nm through $\lambda 4=960$ nm. However, because, for example, the band of $\lambda 3=920$ nm through $\lambda 4=960$ nm is narrower than the visible light band, the reception amount of light is sufficiently small, and thus, influence on detection of a taillight or the like is negligible.

As shown in FIG. 31, the spectral filter layers 49b have the transmittance characteristics of transmitting incident light of a so-called infrared light area of a wavelength range $\lambda 5=880$ nm through $\lambda 6=1100$ nm; and cutting incident light of the other wavelength range (up to 880 nm). The transmittance for the wavelength range $\lambda 5=880$ nm through $\lambda 6=1100$ nm may be preferably greater than or equal to 30%, and more preferably greater than or equal to 90%. The transmittance for the other wavelength range (up to 880 nm) may be preferably less than or equal to 5%, and more preferably 0%.

According to the transmittance characteristics of FIGS. 30 and 31, incident light on the so-called visible light area $\lambda 1=400$ nm through $\lambda 2=670$ nm and the so-called infrared light area $\lambda 3=920$ nm through $\lambda 4=960$ nm are transmitted by the area at which only the spectral filter layer 49a is formed (for example, an area corresponding to the center part ½ of the image sensor 43) by the characteristics of the spectral filter layer 49a.

Figure 32:
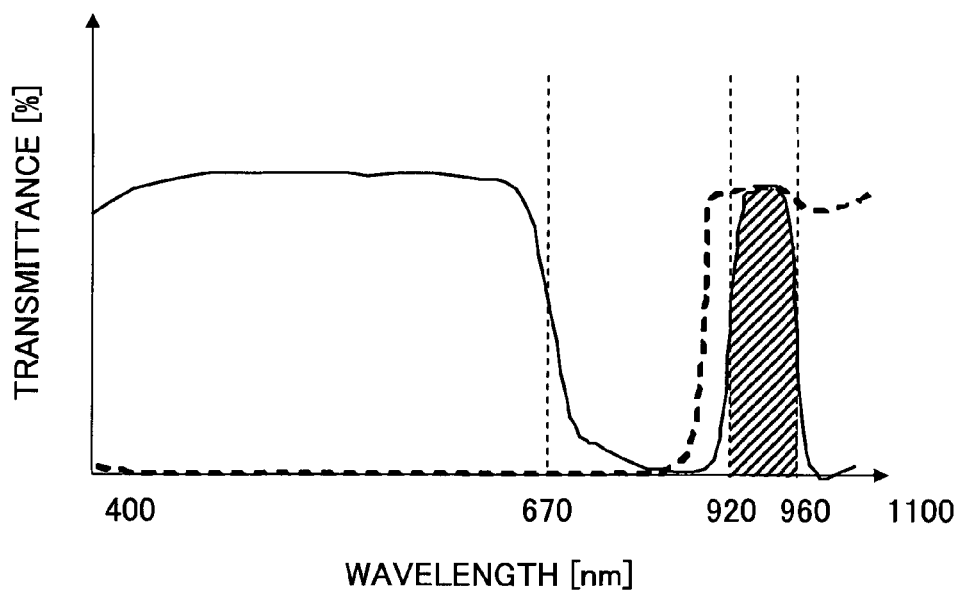
FIG. 32 illustrates transmittance characteristics obtained from combining the spectral filter layers 49a and 49b.

Further, incident light on the area hatched in FIG. 32, i.e., only the wavelength range $\lambda 3=920$ nm through $\lambda 4=960$ nm is transmitted by the area at which both the spectral filter layers 49a and 49b are formed (for example, the areas corresponding to the upper ¼ and lower ¼ of the image sensor 43) by the characteristics of combining the spectral filter layer 49a and spectral filter layers 49b.

It is noted that in order to improve the detection accuracy at the infrared light area, it is preferable that the center value of the wavelength range $\lambda 3=920$ nm through $\lambda 4=960$ nm and the oscillation wavelength of the light source 30 are approximately equal to one another. In other words, it is preferable that the spectral filter layers 49b have the characteristics of selectively transmitting light of a band of wavelengths including the oscillation wavelength range of the light source 30 from incident light.

As described above, according to the first embodiment, the center wavelength of the light source 30 for raindrop detection is 940 nm and the full width at half maximum is 10 nm. Thus, reflected light of light emitted from the light source 30 can pass through the range hatched in FIG. 32 (the wavelength range $\lambda 3=920$ nm through $\lambda 4=960$ nm).

By thus determining that the center value of the wavelength range $\lambda 3=920$ nm through $\lambda 4=960$ nm and the oscillation wavelength of the light source 30 are to be approximately equal to one another, it is possible to distinguish reflected light of infrared wavelength light emitted from the light source 30 from disturbance light having a large amount of light. That is, if the spectral filter layers 49a and 49b are not provided, when an image of reflected light of the infrared wavelength light emitted from the light source 30 reflected by the windshield 101 is taken by the image pickup device 40, the image sensor 43 of the image pickup device 40 would receive disturbance light having a large amount of light such as sunlight, for example, in addition to the reflected light of the infrared wavelength light emitted from the light source 30.

Thus, in order to distinguish the infrared wavelength light from the light source 30 from such disturbance light of a large amount of light, it may be necessary that the light emitting amount of the light source 30 is sufficiently larger than such disturbance light. However, in many cases, it may be difficult to use a light source 30 having such a large light emitting amount.

Thus, the spectral filter layers 49a and 49b are thus provided having the transmittance characteristics shown in FIGS. 30 and 31 on the optical path being incident on the image pickup device 40. Thus, at the area at which both the spectral filter layers 49a and 49b are formed (for example, the areas corresponding to the upper ¼ and lower ¼ of the image sensor 43), only a slight amount of also a disturbance light element such as direct sunlight passing through the wavelength range $\lambda 3=920$ nm through $\lambda 4=960$ nm is incident on the image sensor 43. As a result, it is possible to thus remarkably reduce disturbance light and thus it is possible to improve the accuracy of raindrop detection.

The area at which only the spectral filter layer 49a is formed (for example, the area corresponding to the center part ½ of the image sensor 43) may be used as the vehicle detection image area to be used for detecting a headlight of an oncoming vehicle, a taillight of a vehicle moving ahead of the occupant vehicle, a white line and so forth. The area at which both the spectral filter layers 49a and 49b are formed (for example, the areas corresponding to upper ¼ and lower ¼ of the image sensor 43) may be used as the raindrop detection image areas for detecting a raindrop (the adhered object detection image area).

Figure 33:
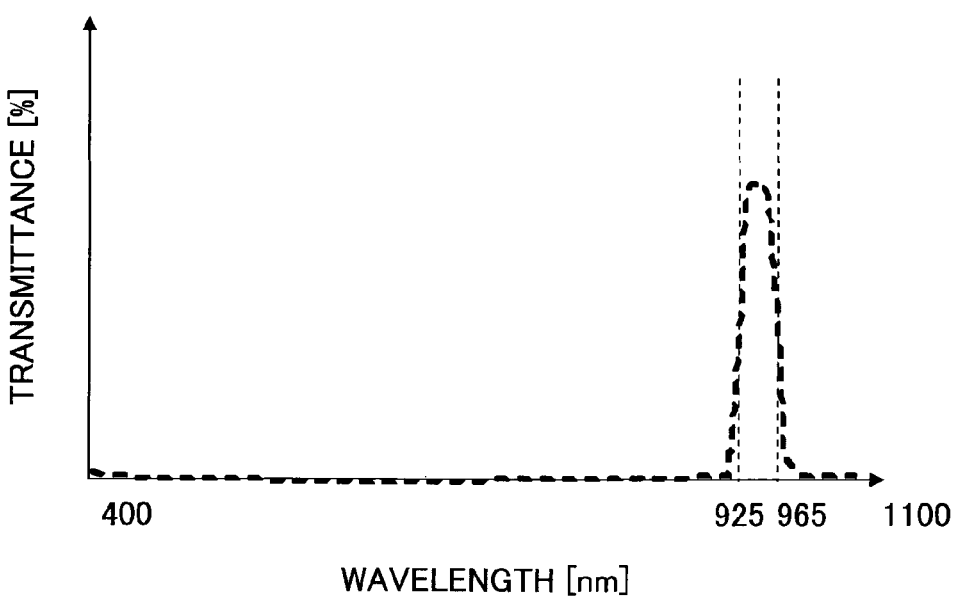
FIG. 33 illustrates other transmittance characteristics of the spectral filters layer 49b.

However, it is also possible that the spectral filter layers 49b have the transmittance characteristics shown in FIG. 33 instead of those of FIG. 31 (the characteristics of cutting light of a shorter wavelength side of the light emitting waveform of the light source 30). That is, the characteristics including a bandpass filter having the peak of transmittance approximately coincident with the light emitting wavelength of the light source 30 as shown in FIG. 33 may be used. In FIG. 33, an infrared light area of the wavelength range $\lambda 5=925$ nm through $\lambda 6=965$ nm is set as the band to transmit light. Then, as a result of being combined with the spectral filter layer 49a (the transmittance characteristics of FIG. 30), only light of approximately the wavelength range $\lambda 5=925$ nm through $\lambda 4=960$ nm is transmitted.

In the characteristics of combining FIGS. 30 and 33 (only transmitting light of the wavelength range $\lambda 5=925$ nm through $\lambda 4=960$ nm), the band to transmit light is narrower than that of combining FIGS. 30 and 31 (only transmitting light of the wavelength range $\lambda 3=920$ nm through $\lambda 4=960$ nm). Thus, it is possible to further reduce disturbance light such as direct sunlight.

As a matter of course, in any case, reflected light of light emitted from the light source 30 can be transmitted. The transmittance characteristics of FIGS. 30, 31, 32 and 33 can be designed in consideration of the light beam angle for being incident on the optical filter 42 from the image pickup lens 41.

Thus, in order to reduce a disturbance light element such as direct sunlight as much as possible, it is preferable that the wavelength of the emitted light of the light source 30 is included in the narrowest wavelength range from among the wavelength range λ3 (920 nm) through λ4 (960 nm), the wavelength range λ3 (920 nm) through λ6 (965 nm), the wavelength range λ5 (925 nm) through λ4 (960 nm) and the wavelength range λ5 (925 nm) through λ6 (965 nm).

It is noted that according to the first embodiment, the advantageous effects obtained from combining the spectral filter layers 49a and 49b are shown. However, it is also useful to use the spectral filter layer 49a or the spectral filter layers 49b as the single member(s) when tolerating somewhat a reduction of the advantageous effects.

It is noted that according to the first embodiment, the polarization filter 47 is used, only a p-polarized element is transmitted from incident light on the optical filter 42 and an s-polarized element is cut. Thus, when it is to be determined whether there is a raindrop, it is possible to prevent disturbance factors caused by unnecessary light having a strong s-polarized element such as light generated from reflection from the road, light from the dashboard or the like in the cabin of the occupant vehicle (background reflections) or the like since the s-polarized element is thus removed. Thus, it is possible to improve the raindrop identification rate.

Further, when identifying, for example, a white line, a headlight of an oncoming vehicle, a taillight of a vehicle moving ahead of the occupant vehicle or the like, it is possible to prevent disturbance factors caused by unnecessary light having a strong s-polarized element such as light such as a headlight, a streetlight or the like reflected from the road, light from the dashboard or the like in the cabin of the occupant vehicle (background, reflections) or the like since the s-polarized element is thus removed. Thus, it is possible to improve the identification rate for a white line, a headlight of an oncoming vehicle and/or a taillight of a vehicle moving ahead of the occupant vehicle.

In particular, it is generally known that a lot of reflected light from rain water surface covering the surface of a road includes an s-polarized element. Thus, by using an image from which an s-polarized element has been thus removed for identifying a white line, it is possible to appropriately identify a white line below the rain water covering the surface of a road and improve the identification rate.

The spectral filter layers 49b can be made of a multilayer film configuration in which thin films of high refractive index and thin films of low refractive index are alternately laminated repetitively to form many layers. By such a multilayer film configuration, setting freedom for spectral transmittance is made large by using interference of light. Further, by thus laminating thin films to form many layers, it is also possible to realize reflectance close to 100% for a specific wavelength (for example, the band of wavelengths other than the red color).

According to the first embodiment, the operating wavelength range of pickup image data is approximately the visible light wavelength range through the infrared light wavelength range. Thus, the image sensor 43 having the sensitivity for this operating wavelength range may be selected and also a filter(s) may be made in which the transmitting wavelength ranges of the multilayer film parts of the spectral filter layers 49a and 49b are set as shown in FIGS. 30 and 31.

Such a filter(s) may be obtained from making a multilayer film such as "substrate/(0.5 H L 0.5 H) p/medium A" in the stated order from the bottom in the laminating direction of the optical filter 42.

It is noted that "L" and "H" mean a material of low refractive index (for example, $SiO_2$) and a material of high refractive index (for example, $TiO_2$), respectively, each having a film thickness corresponding to ¼ wavelength according to the optical path length notation system. That is, this film thickness is a film thickness such that the equation of "nd/λ=0.25" holds where "n" denotes the refractive index, "d" denotes the film thickness and "λ" denotes the cut-off frequency. The above-mentioned "0.5 H L 0.5 H" means a material of high refractive index is laminated for a film thickness of 0.125 wavelength; a material of low refractive index is laminated for a film thickness of 0.25 wavelength; and a material of high refractive index is laminated for a film thickness of 0.125 wavelength.

Further, "p" means the number of times of repeating (laminating) films provided in parentheses. As "p" becomes larger, it is possible to obtain characteristics of a sharper cut edge. Further, in order to reduce influence of ripple ("pulsation" in wavelength distribution of transmittance) and so forth, the film thickness of the above-mentioned ¼ wavelength may be actually a film thickness that is made to be not strictly coincident therewith.

Further, as for the layer close to the substrate, the layer may be omitted when the difference in refractive index from the substrate is very small (for example, less than 10%). Further, the "medium A" is intended to be a resin or an adhesive for contacting air or joining to the image sensor 43. Further, the "substrate" is the filter substrate 46 in the case of the spectral filter layer 49a and the packing member 48 in the case of the spectral filter layers 49b.

Figure 34:
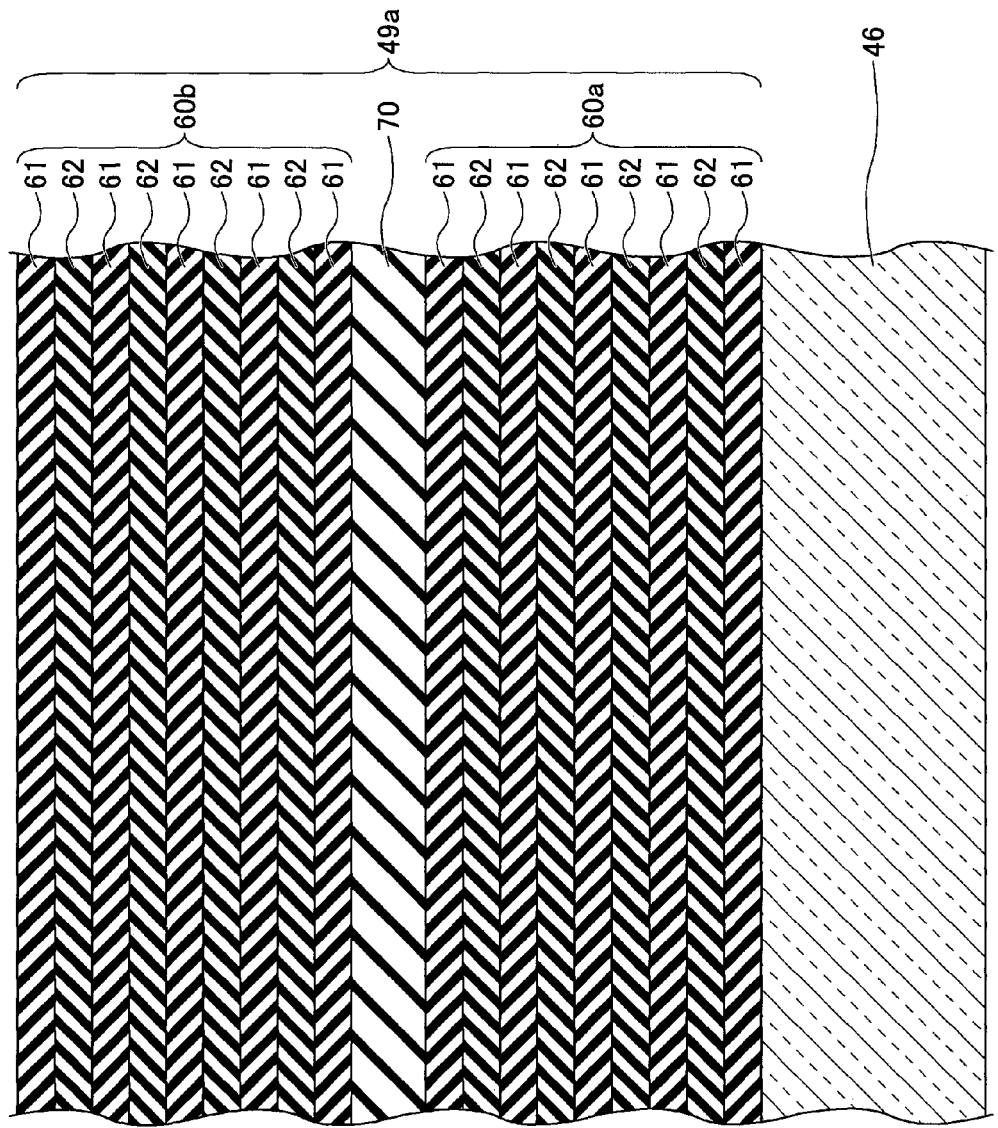
FIG. 34 illustrates a multilayer film configuration of the spectral filter layer 49a that realizes the characteristics shown in FIG. 30.

The multilayer film configuration of the spectral filter layer 49a realizing the characteristics shown in FIG. 30 will now be described. FIG. 34 illustrates the multilayer film configuration of the spectral filter layer 49a realizing the characteristics shown in FIG. 30. As shown in FIG. 34, the spectral filter layer 49a has a structure in which on the filter substrate 46, an alternate laminating part 60a, a center layer 70 and an alternate laminating part 60b are laminated in the stated order.

Each one of the alternate laminating parts 60a and 60b has a structure in which plural sets (in the case of FIG. 34, 4 sets each, as shown) each set including a low refractive index dielectric layer 61 and a high refractive index dielectric layer 62, are laminated; and finally, the low refractive index dielectric layer 61 is laminated. As the material of the low refractive index dielectric layer 61, for example, it is possible to use an inorganic material such as silicon dioxide ($SiO_2$). As the material of the high refractive index dielectric layer 62, for example, it is possible to use an inorganic material such as titanium dioxide ($TiO_2$) or tantalum pentoxide ($Ta_2O_5$).

However, it is also possible to use a structure as that of each one of the alternate laminating parts 60a and 60b in which plural sets, each including the high refractive index dielectric layer 62 and the low refractive index dielectric layer 61, are laminated; and finally, the high refractive index dielectric layer 62 is laminated (i.e., first the high refractive index dielectric layer 62 is laminated on the filter substrate 46).

The thickness of each layer of the low refractive index dielectric layers 61 and the high refractive index dielectric layers 62 may be, for example, on the order of 150 nm or on the order of 100 nm. However, the respective thicknesses of the low refractive index dielectric layers 61 and the high refractive index dielectric layers 62 may be not identical. Further, the thicknesses of the respective layers included in the alternate laminating part 60a and 60b may not necessarily correspond to each other.

The center layer 70 is a layer made of a high refractive index dielectric material such as, for example, titanium dioxide ($TiO_2$) or tantalum pentoxide ($Ta_2O_5$). The thickness of the center layer 70 is made greater than the thickness of any layer of the low refractive index dielectric layers 61 and the high refractive index dielectric layers 62. For example, the thickness of the center layer 70 may be on the order of 260 nm.

The alternate laminating structure through the entirety of the alternate laminating parts 60a and 60b functions as a shortpass filter that transmits incident light of the so-called visible light area of the wavelength range $\lambda 1 = 400$ nm through $\lambda 2 = 670$ nm. Further, a resonator configuration in which the alternate laminating parts 60a and 60b are used as reflective layers and the center layer 70 is used as a resonator layer functions as a bandpass filter that transmits incident light of the so-called infrared light area of the wavelength range $\lambda 3 = 920$ nm through $\lambda 4 = 960$ nm.

It is noted that it is possible to change the band to transmit light of the bandpass filter by changing the thickness of the center layer 70. As will be shown by a numerical example later, it is possible to set the band to transmit light of the bandpass filter to the wavelength range $\lambda 3 = 920$ nm through $\lambda 4 = 960$ nm by setting the thickness of the center layer 70 to be on the order of 2 through 3 times the thickness of the high refractive index dielectric layer 62.

As a numerical example of the multilayer film configuration, the following one may be cited. That is, the alternate laminating part 60a: 0.55 L 1.1 H, 1.1 L, 1.05 H, 1.05 L (LH)2, the center layer 70: 2.6 H, and the alternate laminating part 60b: (LH)2, 1.05 L 1.05 H 1.1 L 1.1 H 0.55 L (where $\lambda = 850$ nm).

Figure 35:
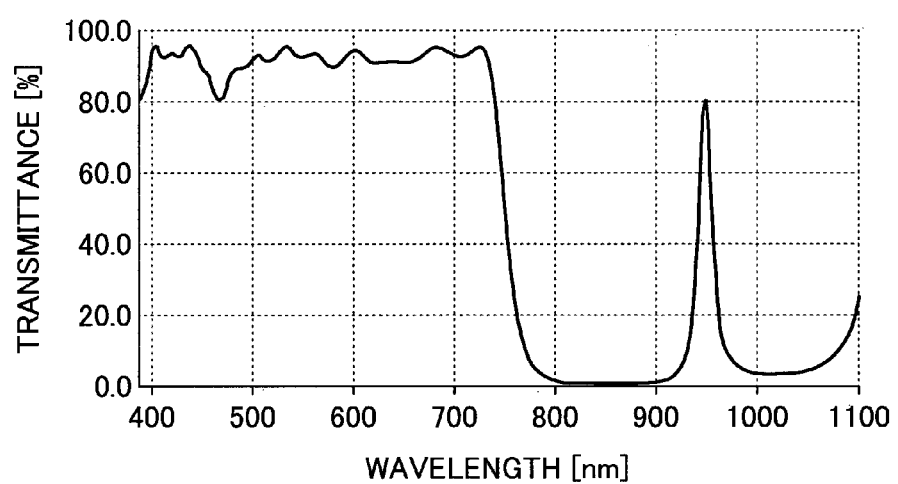
FIG. 35 illustrates transmittance characteristics of the multilayer film configuration shown in FIG. 34.

In the above-mentioned numerical example, the optical path length of the center layer is 2.6 H, and falls within 2 through 3 times the optical path length of the high refractive index dielectric layer 62 included in the alternate laminating parts 60a and 60b. This value is within a numerical range required to use the above-mentioned shortpass filter and the bandpass filter for dual functions. FIG. 35 illustrates filter characteristics corresponding to the above-mentioned numerical example. As shown in FIG. 35, it has been confirmed that the filter characteristics (transmittance characteristics) shown in FIG. 30 can be realized by the multilayer film configuration shown in FIG. 34.

Figure 36:
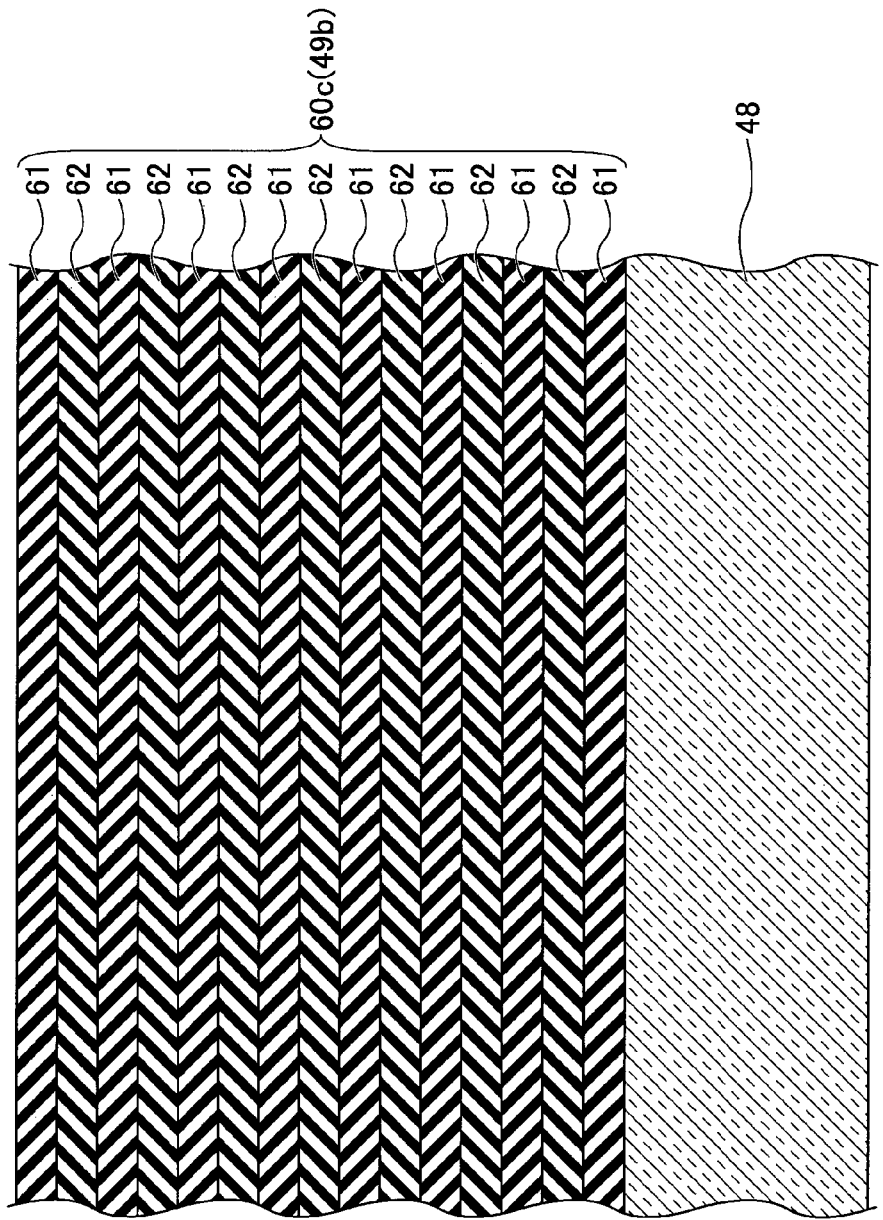
FIG. 36 illustrates a multilayer film configuration of the spectral filter layer 49b that realizes the characteristics shown in FIG. 31.

Next, a multilayer film configuration of the spectral filter layer 49b realizing the characteristics shown in FIG. 31 will be described. FIG. 36 illustrates a multilayer film configuration of the spectral filter layer 49b realizing the characteristics shown in FIG. 31. As shown in FIG. 36, the spectral filter layer 49b has a structure in which on the packing member 48 acting as a substrate, an alternate laminating part 60c is formed. That is, the alternate laminating part 60c equals the spectral filter layer 49b.

Similar to the alternate laminating parts 60a and 60b, the alternate laminating part 60c has a structure in which plural sets (in the case of FIG. 36, seven sets), each including a low refractive index dielectric layer 61 and a high refractive index dielectric layer 62, are lamented; and finally, a low refractive index dielectric layer 61 is laminated.

However, it is also possible to use a structure as that of the alternate laminating part 60c in which plural sets, each including a high refractive index dielectric layer 62 and a low refractive index dielectric layer 61, are laminated; and finally, a high refractive index dielectric layer 62 is laminated (that is, on the packing member 48, first the high refractive index dielectric layer 62 is laminated). The materials and thicknesses of the low refractive index dielectric layers 61 and high refractive index dielectric layers 62 may be the same as or similar to those of the case of the alternate laminating parts 60a and 60b.

The alternate laminating configuration through the entirety of the alternate lamenting part 60c functions as a longpass filter that transmits incident light of the so-called infrared light area of the wavelength range $\lambda 5 = 880$ nm through $\lambda 6 = 1100$ nm.

As a numerical example of the multilayer film configuration realizing the characteristics shown in FIG. 31, the following one may be cited. That is, the alternate laminating part 60c: 0.29 H 0.59 L 0.605 H (0.605 L 0.605 H)8 0.34 L 0.75 H 0.8 L 0.8 H (0.8 L 0.8 H)8 0.43 L 1.1 H 1.1 L 1.05 H (1.05 L 1.05 H)8 1.05 L 0.52 H (where $\lambda = 720$ nm).

Figure 37:
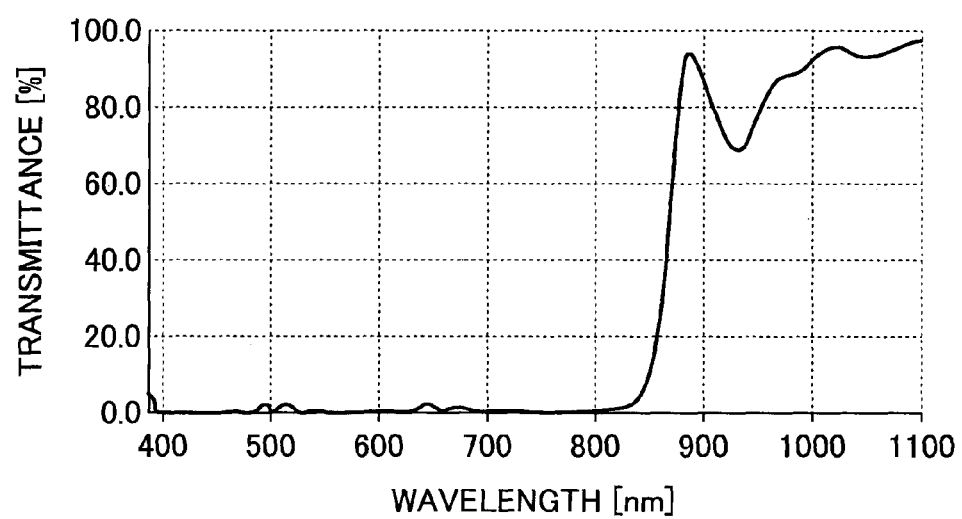
FIG. 37 illustrates transmittance characteristics of the multilayer film configuration shown in FIG. 36.

FIG. 37 illustrates filter characteristics corresponding to the above-mentioned numerical example. As shown in FIG. 37, it has been confirmed that the filter characteristics (transmittance characteristics) shown in FIG. 31 can be realized by the multilayer film configuration shown in FIG. 36.

Figure 38:
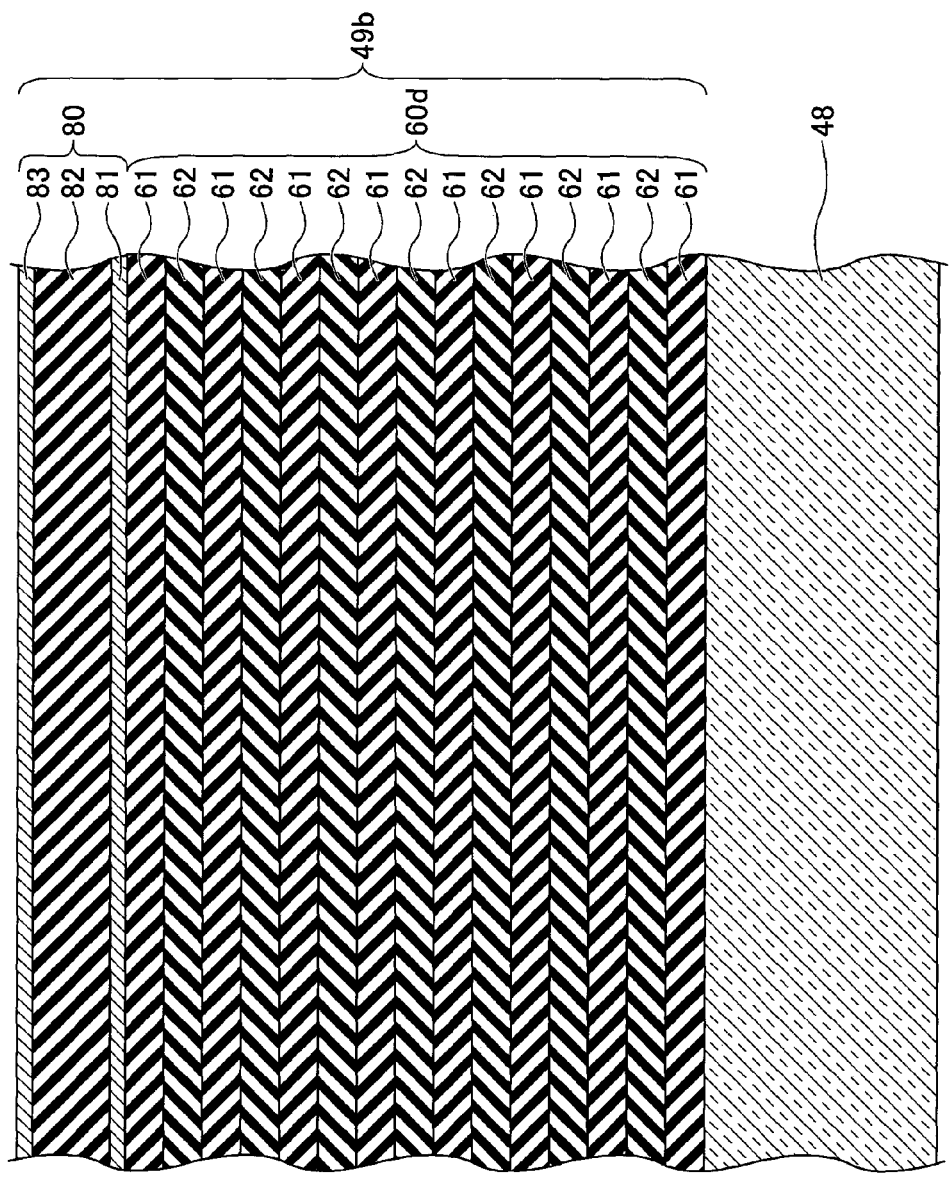
FIG. 38 illustrates a multilayer film configuration of the spectral filter layer 49b that realizes the characteristics shown in FIG. 33.

Next, a multilayer film configuration of the spectral filter layer 49b realizing the characteristics shown in FIG. 33 will be described. FIG. 38 illustrates a multilayer film configuration of the spectral filter layer 49b realizing the characteristics shown in FIG. 33. As shown in FIG. 38, the spectral filter layer 49b has a structure in which on the packing member 48 acting as a substrate, an alternate laminating part 60d and a metal dielectric laminating part 80 are laminated in the stated order.

Similar to the alternate laminating parts 60a through 60c, the alternate laminating part 60d has a structure in which plural sets (in the case of FIG. 38, seven sets), each set including a low refractive index dielectric layer 61 and a high refractive index dielectric layer 62, are lamented; and finally, a low refractive index dielectric layer 61 is laminated.

However, it is also possible that the alternate laminating part 60d has a structure in which plural sets, each including a high refractive index dielectric layer 62 and a low refractive index dielectric layer 61, are laminated; and finally, a high refractive index dielectric layer 62 is laminated (that is, on the packing member 48, first the high refractive index dielectric layer 62 is laminated). The materials and thicknesses of the low refractive index dielectric layers 61 and high refractive index dielectric layers 62 may be the same as or similar to those of the case of the alternate laminating parts 60a through 60c.

The metal dielectric laminating part 80 has a structure in which a metal layer 81, a low refractive index dielectric layer 82 and a metal layer 83 are laminated in the stated order. As the material of each one of the metal layers 81 and 83, for example, silver (Ag), chrome (Cr), gold (Au), titanium (Ti) or the like may be used. The thickness of each one of the metal layers 81 and 83 may be, for example, on the order of 30 nm.

As the material of the low refractive index dielectric layer 82, for example, it is possible to use an inorganic material such as silicon dioxide ($SiO_2$). The thickness of the low refractive index dielectric layer 82 may be, for example, on the order of 280 nm. It is possible to change the band to transmit light of the bandpass filter by changing the thickness of the metal dielectric laminating part 80 (in particular, the thickness of the low refractive index dielectric layer 82).

By thus laminating the alternate laminating part 60d and the metal dielectric laminating part 80, it functions as the bandpass filter that transmits incident light of the so-called infrared light area of the wavelength range $\lambda 5 = 925$ nm through $\lambda 6 = 965$ nm.

As a numerical example of the multilayer film configuration realizing the characteristics shown in FIG. 33, the following one may be cited. That is, the alternate laminating part 60d: (0.27 H 0.57 L 0.27 H)8 and the metal dielectric laminating part 80: Mt 2 L Mt (where $\lambda = 820$ nm, and "Mt" means Ag having the film thickness of 30 nm).

Figure 39:
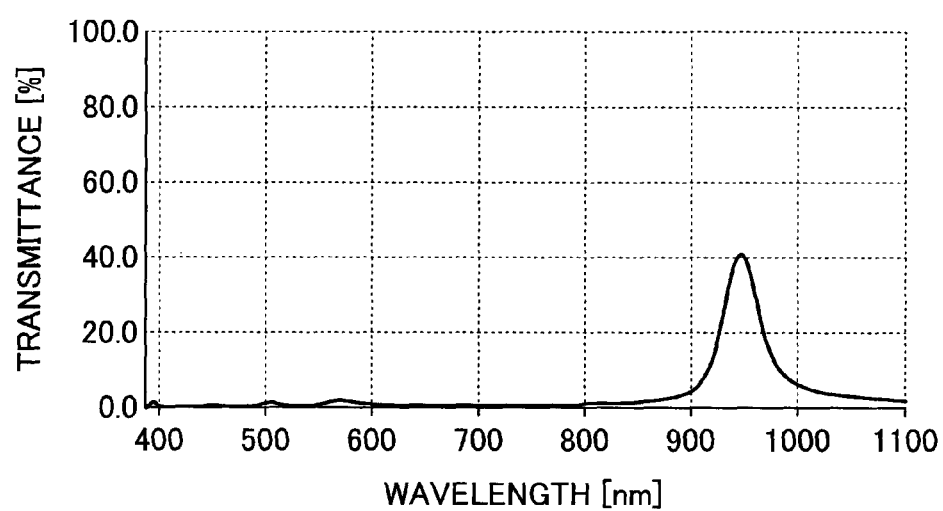
FIG. 39 illustrates transmittance characteristics of the multilayer film configuration shown in FIG. 38.

FIG. 39 illustrates filter characteristics corresponding to the above-mentioned numerical, example. As shown in FIG. 39, it has been confirmed that the filter characteristics (transmittance characteristics) shown in FIG. 33 can be realized by the multilayer film configuration shown in FIG. 38.

Figure 40:
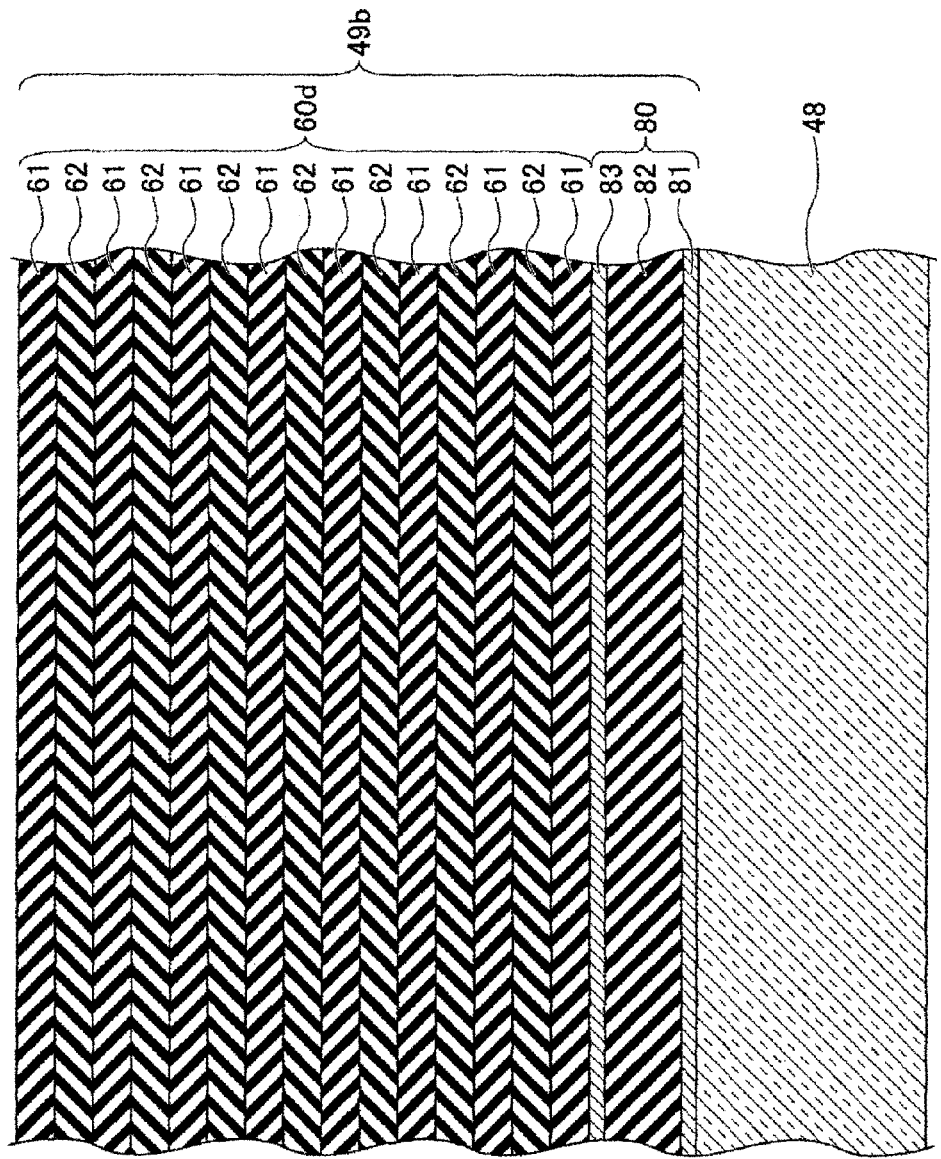
FIG. 40 illustrates another multilayer film configuration of the spectral filter layer 49b that realizes the characteristics shown in FIG. 33.

It is noted that instead of FIG. 38, it is also possible to realize the filter characteristics (transmittance characteristics) shown in FIG. 33 by using a multilayer film configuration such as that of FIG. 40. That is, the spectral filter layer 49b may have a structure in which on the packing member 48, the alternate laminating part 60d and metal dielectric laminating part 80 are laminated in the stated order, as shown in FIG. 38. Further, the spectral filter layers 49b may instead have a structure in which on the packing member 48, the metal dielectric laminating part 80 and alternate laminating part 60d are laminated in the stated order, as shown in FIG. 40.

It is noted that it is possible to realize the spectral filter layers 49b having a high weatherproof property by using an inorganic material such as titanium dioxide ($TiO_2$) as the high refractive index dielectric material and using an inorganic material such as silicon dioxide ($SiO_2$) as the low refractive index dielectric material.

One example of a method of manufacturing the spectral filter layers 49b according to the first embodiment will now be described. First, on the packing member 48 formed on the filter substrate 46 and the polarization filter layer 47, the above-described multilayer film is formed. As a method of manufacturing such a multilayer film, a well-known method such as evaporation may be used. Next, the multilayer film is removed at the place corresponding to the not spectral area (for example, the area corresponding to the center part ½ of the image sensor 43).

As a specific method of thus partially removing the multilayer film, a common liftoff method may be used. According to the liftoff method, a pattern reverse to a target pattern is previously formed on the packing member 48 with a metal or a photoresist. Then, after the multilayer film is formed thereon, the multilayer film is removed at the place corresponding to the not spectral area together with the metal or photoresist.

Further, in the case where, as shown in FIG. 25, the spectral filter layer 49b has a size (for example, a size of a width greater than or equal to 100 μm) sufficiently larger than the size of each one of the pixels of the image sensor 43, the following method may be used. That is, a mask may be provided to cover the area other than the areas to form the spectral filter layers 49b at a time of evaporation of the multilayer film, and the evaporation may be carried out only for the areas on which to form the spectral filter layers 49b via the mask.

According to the first embodiment, the multilayer film configuration is used for the spectral filter layers 49b. Thus, an advantageous effect of large setting freedom for the spectral characteristics is obtained. Generally speaking, a color filter used in a color sensor or the like is formed by a resist agent. When such a resist agent is used, it may be difficult to control the spectral characteristics in comparison to the case of using a multilayer film configuration. According to the first embodiment, the multilayer film configuration is used for the spectral filter layers 49b. Thus, it is possible that the wavelength of the light source 30 is approximately coincident with the band of wavelengths of the raindrop detection areas.

It is noted that also the spectral filter layer 49a can be manufactured by a method the same as or similar to that of the spectral filter layers 49b. However, the process of removing a part of a film using a liftoff method or the like is not necessary.

Figure 41:
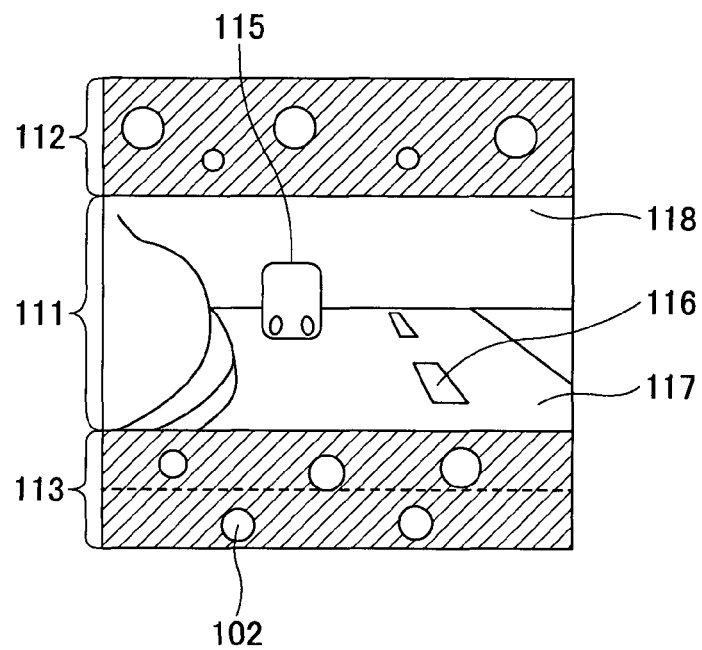
FIG. 41 schematically shows an example of a pickup image.

The reason why the raindrop detection image areas are provided at the upper part and the lower part will now be described. FIG. 41 illustrates a pickup image.

In many cases, an image of a headlight (not shown) of an oncoming vehicle, a taillight of a vehicle 115 moving ahead of the occupant vehicle and a white line 116 mainly exist at a center part of the pickup image. Further, normally, at a lower part of the pickup image, an image of a road surface 117 immediately in front of the occupant vehicle exists, and at an upper part of the pickup image, an image of the sky 118 exists. That is, information required for identifying the headlight (not shown) of the oncoming vehicle, the taillight of the vehicle 115 moving ahead of the occupant vehicle and the white line 116 concentrate in the center part of the pickup image, and thus, information of the upper part and the lower part of the pickup image is not very important for identifying them.

Thus, in a case of carrying out both detection of the oncoming vehicle, the vehicle 115 moving ahead of the occupant vehicle and/or the white line 116 and detection of a raindrop 102 from a single set of pickup image data, it is advantageous to use the center part of the pickup image as the vehicle detection image area 111 and the upper part and lower part of the pickup image as the raindrop detection image areas 112 and 113, as shown in FIG. 41.

Thus, corresponding to the vehicle detection image area 111 of FIG. 41, the spectral filter layer 49a such as that shown in FIG. 28 is provided. Further, corresponding to the raindrop detection image areas 112 and 113 of FIG. 41, the spectral filter layers 49a and 49b such as those shown in FIG. 28 are provided.

It is noted that when the image pickup direction of the image pickup device 40 is inclined toward a lower direction, the hood of the occupant vehicle may be included in a lower part of the image pickup area (the broken line in the raindrop detection image area 113 of FIG. 41). In such a case, sunlight, the taillight of the vehicle 115 moving ahead of the occupant vehicle or the like reflected by the hood of the occupant vehicle may become disturbance light which may be then included in the pickup image data.

Also in such a case, according to the first embodiment, the spectral filter layers 49a and 49b are provided at the place corresponding to the lower part of the pickup image. Thus, the disturbance light such as sunlight, the taillight of the vehicle 115 moving ahead of the occupant vehicle or the like reflected by the hood of the occupant vehicle is removed. Thus, the detection accuracy for the raindrop 102 can be improved.

It is noted that when detecting a vehicle moving ahead of the occupant vehicle, the vehicle moving ahead of the occupant vehicle is detected as a result of the taillight in the pickup image being identified. However, the taillight has the amount of light smaller in comparison to that of a headlight of an oncoming vehicle. Also, there is a lot of disturbance light such as from a street light. Thus, it may be difficult to detect a taillight with high accuracy only from the simple brightness data.

Thus, it is necessary to use spectral information for identifying a taillight and identify the taillight based on the received amount of red color light. However, the respective pixels included in the image sensor 43 also have sensitivity for light of infrared wavelength range. Thus, when the image sensor 43 receives light including an infrared wavelength range, the thus obtained pickup image may become a reddish one as a whole. As a result, it may be difficult to identify an image part of red color corresponding to a taillight.

According to the first embodiment, as described above, the spectral filter layer 49a has the transmission characteristics to cut incident light of the wavelength range 670 nm through 920 nm. Thus, most of the infrared wavelength range is removed from the pickup image data to be used for identifying a taillight. Thus, it is possible to improve the identification accuracy for a taillight.

It is noted that in FIG. 28, a gap is provided between the optical filter 42 and the image sensor 43. However, it is preferable that the optical filter 42 is joined to the image sensor 43. This is because it becomes easier to cause the boundaries of the respective areas of the polarization filter layer 47 and the spectral filter layers 49b of the optical filter 42 and the boundaries of the respective pixels on the image sensor 43 to be coincident. That is, as a result of the optical filter 42 and the image sensor 43 being tightly joined together, the boundaries between the raindrop detection areas and the area for detecting vehicle surrounding information become clearer, and it is possible to improve the determination accuracy as to whether a raindrop exists.

In the case of thus tightly joining the optical filter 42 to the image sensor 43, the optical filter 42 and the image sensor 43 may be joined together using UV adhesive. Alternatively, it is also possible to carry out thermo-compression bonding or UV adhesion on four side areas that are out of the effective image pickup area in a state of being supported by a spacer(s).

It is noted that it is possible to avoid warpage of the optical filter 42 by forming the spectral filter layers 49a and 49b on both sides of the filter substrate 46. That is, when forming a multilayer film(s) (spectral filter layer(s)) only on one side of the filter substrate 46, the filter substrate 46 may become stressed and warpage may occur. However, in a case of forming multilayer films (spectral filter layers) on both sides of the filter substrate 46 as shown in FIG. 28, the effects of the stress are canceled, and thus, warpage is avoided.

Further, in a case where the spectral filter layer(s) 49b were provided only one of the upper part and the lower part, it might be difficult to adhere the optical filter 42 to the image sensor 43 in parallel, and they might be inclined with respect to the Z-axis (see FIG. 28). If they were adhered together in the thus inclined state, the optical path lengths would vary between the upper part and the lower part of the pickup image, and thus recognition accuracy might be degraded to cause error in reading coordinates of a white line in a case of detecting vehicle surrounding information such as a white line, for example. As shown in FIG. 28, such a problem can be solved by providing the spectral filter layers 49b at both the upper part and the lower part.

However, also in a case of forming the spectral filter layers 49a and 49b only on one side of the filter substrate 46 or in a case where the spectral filter layer(s) is (are) provided at only one of the upper part and the lower part, a certain advantageous effect(s) can be obtained.

It is noted that according to the first embodiment, a view in the image pickup area and an image on the image sensor 43 are upside down therebetween because of characteristics of the image pickup lens 41.

The raindrop detection and vehicle detection will now be described in further detail. FIG. 42 illustrates light beams concerning the raindrop detection and vehicle detection.

The incident angle on the windshield 101 of the light source 30 is set so that an image of the reflected light from somewhere on the boundary plane between the raindrop 102 and the air will be taken. There are two of layouts in each of which reflected light from the interface plane between the raindrop 102 and the air becomes strongest. One of these layouts is a layout of installing the light source 30 at a position approximately opposite to the optical axis of the image pickup lens 41 with respect to the normal of the windshield 101, which normal intersects the optical axis of the image pickup lens 41. The other is a layout of installing the light source 30 in such a manner that the optical axis of the light source 30 is approximately the same as the optical axis of the image pickup lens 41.

Further, a case where reflected light from the boundary plane between the raindrop 102 and the air becomes weakest is a case where the normal of the windshield 101, which normal intersects the optical axis of the image pickup lens 41, is approximately coincident with the optical axis of the light source 30. Here, as an example, the light source 30 is assumed to be put (placed) in such a manner that the regular reflection on the outer wall surface of the windshield 101 is approximately coincident with the optical axis of the image pickup lens 41.

The light beam A of FIG. 42 is a light beam emitted by the light source 30 and passing through the windshield 101. In a case where no raindrop 102 has adhered to the outer wall surface of the windshield 101, light emitted from the light source 30 toward the windshield 101 passes through the windshield 101 and leaks out to the outside of the occupant vehicle as it is, as the light beam A. Thus, as the light source 30, it is preferable that in consideration of the emitted light being emitted to an eye of a human being, a light source is selected having the wavelength and amount of light of the eye-safe range. Further, as shown in FIG. 42, it is more preferable that a configuration is made such that light emitted by the light source 30 toward the windshield 101 goes in an upward vertical direction or the like so that the likelihood of the emitted light being emitted to an eye of a human being can be reduced.

The light beam B is a light beam emitted by the light source 30, reflected by the inner wall surface of the windshield 101 in the regular reflection manner and is incident on the image pickup device 40. A part of the light emitted by the light source 30 toward the windshield 101 is reflected by the inner wall surface of the windshield 101 in the regular reflection manner. It has been known that generally speaking, as the polarized element of this regular reflection (light beam B), an s-polarized element that oscillates in the direction perpendicular to the incident surface (in the direction perpendicular to the paper sheet of FIG. 42) is dominant.

The regular reflection (light beam B) reflected in the regular reflection manner by the inner wall surface of the windshield 101 after being emitted by the light source 30 does not vary by the fact as to whether a raindrop 102 that has adhered to the outer wall surface of the windshield 101 exists. Thus, this light is not only unnecessary light for raindrop detection but also may act as disturbance light that reduces the detection accuracy of raindrop detection. Thus, according to the first embodiment, the light beam B (s-polarized element) is cut by the polarization filter layer 47, and thus it is possible to avoid degradation of the raindrop detection accuracy.

The light beam C is a light beam emitted by the light source 30, passing through the inner wall surface of the windshield 101; and after that, reflected by the interface between the raindrop 102 that has adhered to the outer wall surface of the windshield 101 and the air and incident on the image pickup device 40. A part of the light emitted from the light source 30 toward the windshield 101 passes through the inner wall surface of the windshield 101. However, the passing through light includes a p-polarized element larger than an s-polarized element.

In a case where a raindrop 102 has adhered to the outer wall surface of the windshield 101, light having passed through the inner wall surface of the windshield 101 does not leak out to the outside as the light beam A but is reflected by the interface between the raindrop 102 and the air, again passes through the windshield 101 toward the image pickup device 40 and is incident on the image pickup device 40.

At this time, since the spectral filter layer 49a is configured to transmit the oscillation waveform (infrared light) of the light source 30, the light beam C passes through the spectral filter layer 49a. Further, since the metal wires of the wire grid structure in the polarization filter layer 47 have such a longitudinal direction that the polarization filter layer 47 transmits a p-polarized element, the light beam C having a p-polarized element as a main element also passes through the polarization filter layer 47. Further, the spectral filter layer 49b is configured to transmit the oscillation wavelength (infrared light) of the light source 30. Thus, the light beam 30 also passes through the spectral filter layer 49b. Thus, the light beam C reaches the raindrop detection image areas of the image sensor 43, and it is possible to detect the raindrop 102 by the received amount of light.

The light beam D is a light beam passing through the windshield 101 from the outside and traveling toward the raindrop detection image area of the image sensor 43 of the image pickup device 40. The light may act as disturbance light when detecting a raindrop. However, according to the first embodiment, most of incident light except a part of infrared light is cut by the spectral filter layers 49a and 49b. Thus, most of the light beam D does not reach the raindrop detection image area of the image sensor 43. Thus, it is possible to avoid degradation of the raindrop detection accuracy due to the light beam D.

The light beam E is a light beam passing through the windshield 101 from the outside and traveling toward the raindrop detection image area of the image sensor 43 of the image pickup device 40. By the transmittance characteristics of the spectral filter layer 49a, only visible light and a part of infrared light of a p-polarized element of the light beam E pass through the spectral filter layer 49a and reach the vehicle detection image area of the image sensor 43 and thus an image thereof is taken.

This pickup image is used to detect a headlight of an oncoming vehicle, a taillight of a vehicle moving ahead of the occupant vehicle, a white line and so forth. It is noted that the s-polarized element of the light beam E are removed by the polarization filter layer 47. Thus, it is possible to reduce disturbance factors due to unnecessary light including strong s-polarized light such as light of a headlight, a street light and so forth reflected by the road, light from the dashboard or the like in the cabin of the occupant vehicle (background reflections) and so forth.

Next, exposure amount adjustment when the image processing apparatus 10 obtains a pickup image will be described. As one example, as being enclosed by the alternative long and short dash line in FIG. 26, a case will be considered where, vertically adjacent two and horizontally adjacent two for a total of four areas (areas including pixels $43a_1$, $43a_2$, $43b_1$ and $43b_2$) are regarded as one unit of pickup image data. On the pixels $43a_1$, $43a_2$, $43b_1$ and $43b_2$, light having passed through the spectral filter layer 49a, the polarization filter layer 47 and the spectral filter layer 49b is incident. Thus, the pixels $43a_1$, $43a_2$, $43b_1$ and $43b_2$ receive the p-polarized element of the infrared light from the incident light on the optical filter 42, and thus an image by the p-polarized element of the infrared light is formed. Then, using the image thus formed by the p-polarized element of the infrared light, it is possible to determine whether a raindrop exists, for example.

It is noted that the light source 30 may emit light continuously (which may also be called continuous wave (CW) light emission) or may emit light in a form of pulses in specific timings. It is possible to further reduce the influence of disturbance light by synchronizing the timing of light emission and the timing of image pickup. Further, in a case of installing plural light sources, the plural light sources may emit light simultaneously or may emit light in sequence. In a case of emitting light in sequence, it is possible to further reduce the influence of disturbance light by synchronizing the timing of light emission and the timing of image pickup.

Next, one unit of pickup image data is formed by an area including the pixels $43c_1$, $43c_2$, $43d_1$ and $43d_2$. On the pixels $43c_1$, $43c_2$, $43d_1$ and $43d_2$, light having passed through the spectral filter layer 49a and the polarization filter layer 47 is incident. Thus, the pixels $43c_1$, $43c_2$, $43d_1$ and $43d_2$ receive the p-polarized element of mainly the visible light from the incident light on the optical filter 42, and an image by the p-polarized element of mainly the visible light is generated. By using the thus generated image by the p-polarized element of mainly the visible light, it is possible to detect vehicle surrounding information, for example.

It is noted that when an image of the vehicle detection image area is taken, the light source 30 may be turned off, or the light source 30 may be always turned on.

Next, one unit of pickup image data is formed by an area including the pixels $43g_1$, $43g_2$, $43h_1$ and $43h_2$. The same as the area including $43a_1$, $43a_2$, $43b_1$ and $43b_2$, the area including the pixels $43g_1$, $43g_2$, $43h_1$ and $43h_2$ generates an image by the p-polarized element of the infrared light and by using the generated image, it is possible to determine whether a raindrop exists, for example. It is noted that the same as the case of the area including $43a_1$, $43a_2$, $43b_1$ and $43b_2$, the light source 30 emits light.

Similarly, images are generated in sequence, each using other vertically adjacent two and horizontally adjacent two for a total of four pixels as one unit. Thus, the image of the entirety of the image sensor 43 is generated. However, it is not necessary to generate images of the raindrop detection areas and images of the vehicle detection image area alternately. Images of the same area(s) may be generated successively.

Thus, the example has been described in which four pixels are regarded as one unit. However, it is not necessary to be limited thereto. For example, when images of the raindrop detection image areas that are put at the upper part and the lower part of the image sensor 43 are taken, it is possible to regard a pixel area corresponding to the spot size on the image sensor 43 of the reflected light from the light source 30 as one unit. When an image of the vehicle detection image area that is put at the center of the image sensor 43 is taken, it is possible to regard one pixel as one unit in a case of using a monochrome sensor as the image sensor.

The obtained amounts of light are remarkably different between the raindrop detection image areas (the adhered object detection image areas) at which the spectral filter layer 49a, the polarization filter layer 47 and the spectral filter layers 49b are formed and the vehicle detection image area at which the spectral filter layer 49a and the polarization filter layer 47 are formed but the spectral filter layer 49b is not formed. This is because mainly only the reflected light of the infrared light emitted by the light source 30 is incident on the raindrop detection image areas, whereas mainly visible light is incident on the vehicle detection image area.

Thus, it is preferable to change the exposure amount between in a case of taking an image of the raindrop detection image area and in a case of taking an image of the vehicle detection image area. Thus, it is possible to take images with optimum exposure amounts for the respective raindrop detection image area and vehicle detection image area. For example, in a case of taking a remote image, automatic exposure adjustment may be carried out based on image information of the vehicle detection image area while detecting a part of the vehicle detection image area. In a case of taking an image of a raindrop, automatic exposure adjustment may be carried out based on image information of the raindrop detection image area while detecting a part of the raindrop detection image area.

In order to change the exposure amount, the exposure period of time may be changed between when taking an image of the raindrop detection image area and when taking an image of the vehicle detection image area. For example, it is possible to change the exposure period of time as a result of the image analysis unit 50 controlling the period of time for converting the incident light into the electric signal by the image sensor 43. Further, as in a third variant of the first embodiment described later, it is also possible to change the exposure amount by providing an aperture limiting part corresponding to each pixel of the image sensor 43 at the area at which the spectral filter layers 49b are not formed.

At the vehicle detection image area, change in the amount of light of the surroundings is large. In fact, the luminance of the vehicle surroundings for which the image pickup device takes an image changes from several tens of thousands of luxes during the daytime through less than or equal to one lux during the nighttime. Thus, it is necessary to adjust the exposure period of time depending on particular image pickup scenes. For this purpose, well-known automatic exposure control techniques may be used. It is noted that according to the first embodiment, it is preferable to carry out exposure control based on image information of a road surface area since an object exists around the road surface.

On the other hand, as for the raindrop detection image areas, since the setting has been made such that only the reflected light from an adhered object of the emitted light of the light source 30 is to be taken in, a change of the amount of light from the surrounding environment is small. Thus, it is also possible to take an image with a fixed exposure period of time (i.e., take an image with a fixed exposure amount) for the raindrop detection image areas.

Figure 43B:
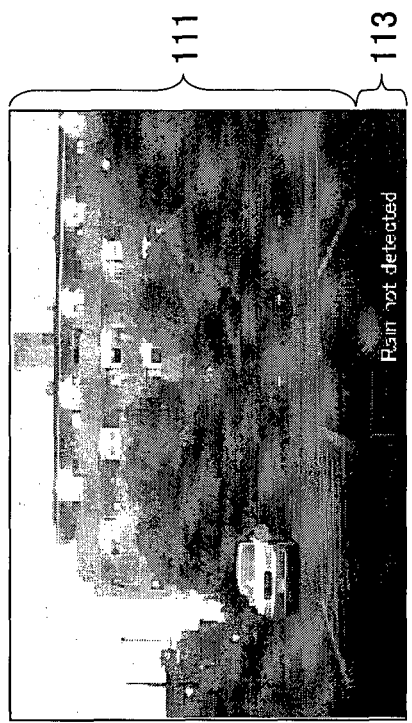
FIGS. 43A and 43B illustrate pickup images.
Figure 43A:
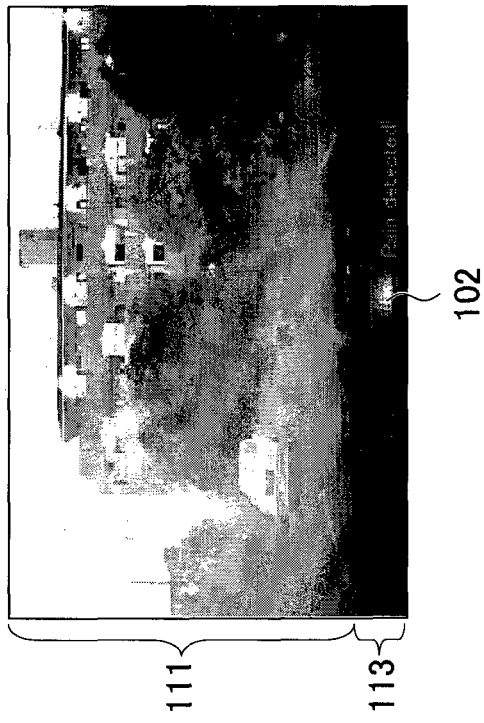

FIGS. 43A and 43B illustrate pickup images. FIG. 43A shows an example of a pickup image when raindrop has adhered to the outer wall surface of the windshield 101. FIG. 43B shows an example of a pickup image when no raindrop has adhered to the outer wall surface of the windshield 101. It is noted that according to the first embodiment, the raindrop detection image areas are provided at the pickup image upper part and the pickup image lower part. FIGS. 43A and 43B show images in which the raindrop detection image area at the pickup image upper part is omitted.

In the pickup images of FIGS. 43A and 43B, the lower parts 113 are the raindrop detection image areas 113 and the other areas are the vehicle detection image areas 111, respectively. In the raindrop detection image areas 113, light from the light source 30 is reflected (as indicated by the reference numeral 102) as shown in FIG. 43A when a raindrop 102 has adhered. No light from the light source 30 is reflected as shown in FIG. 43B when no raindrop 102 has adhered.

Further, an indication "Rain detected" in FIG. 43A (not clearly recognizable in the figure) shows the state of having recognized the raindrop 102. An indication "Rain not detected" in FIG. 43B shows the state of not having recognized the raindrop 102. Such a raindrop recognition process at the raindrop detection image area 113 can be easily achieved by adjusting a threshold for a reception amount of light of the reflected light from an adhered object of emitted light from the light source 30. It is noted that the threshold may not necessarily be a fixed value, and may be appropriately changed depending on the surrounding situation of the occupant vehicle in which the image pickup device 40 is installed or the like. For example, the optimum value may be calculated based on exposure adjustment information of the vehicle detection image area 111 or the like and the threshold may be changed thereby.

First Variant of First Embodiment

The first variant of the first embodiment is an example in which the area dividing method of the spectral filter layer on the side of the image sensor 43 is changed. For the first variant of the first embodiment, description for the same elements as those described above will be omitted.

Figure 44:
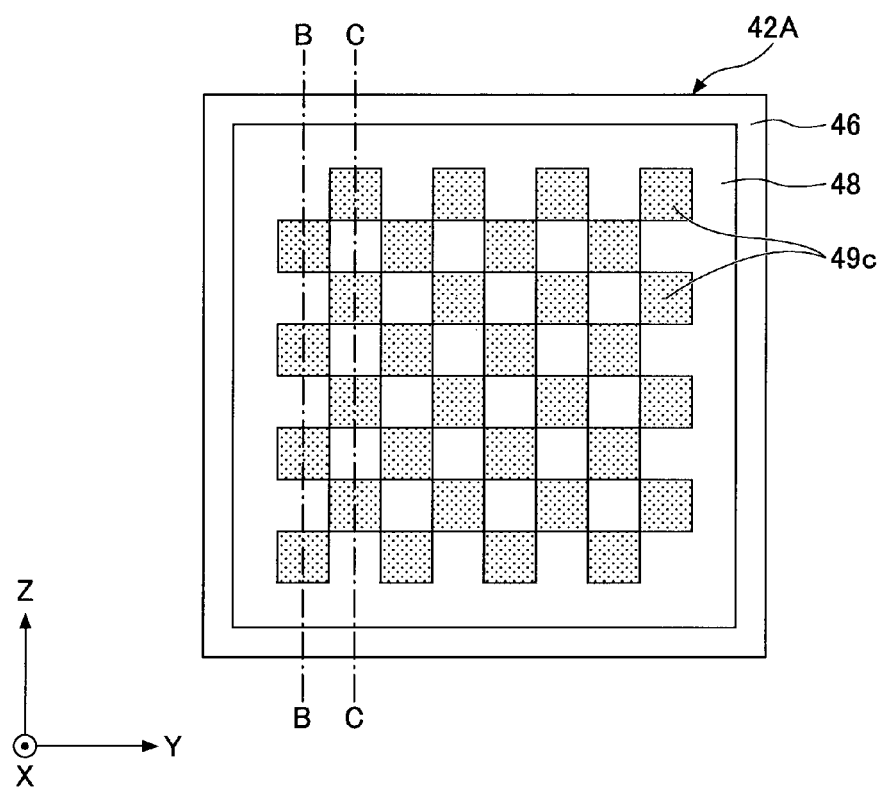
FIG. 44 shows a view of an optical filter 42A according to a first variant of a first embodiment viewed from the side of the sensor substrate 44.
Figure 45:
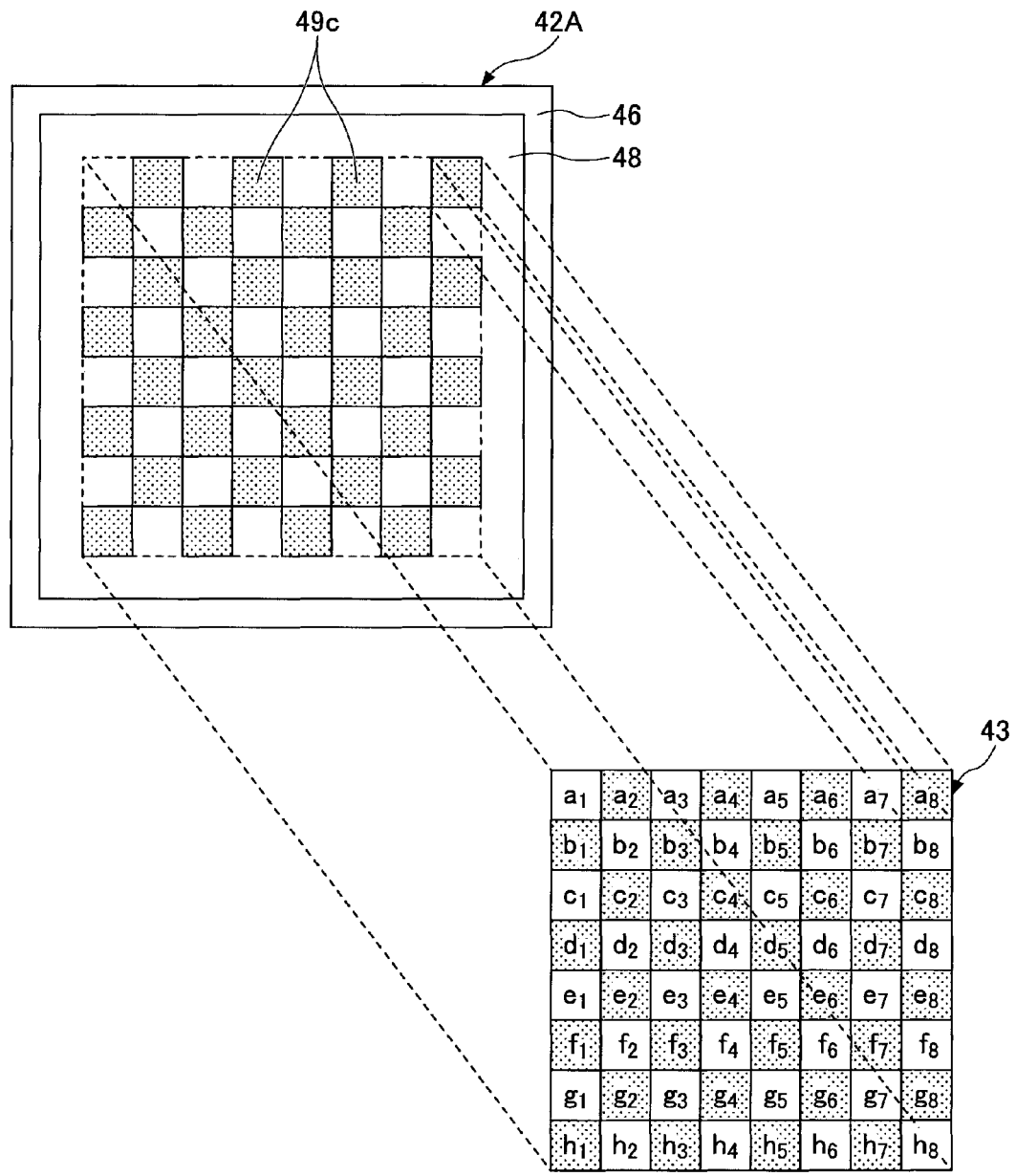
FIG. 45 illustrates a correspondence of positional relationship between the optical filter 42A and the image sensor 43 according to the first variant of the first embodiment.
Figure 46:
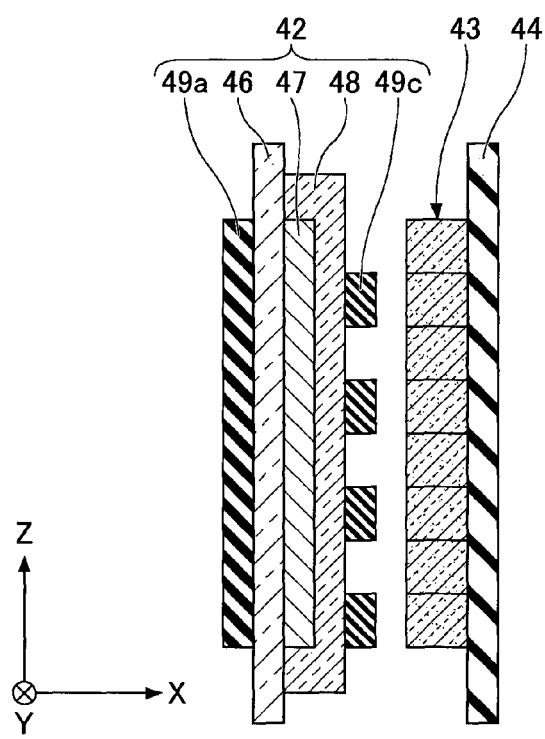
FIG. 46 shows a sectional view taken along a B-B line of FIG. 44.
Figure 47:
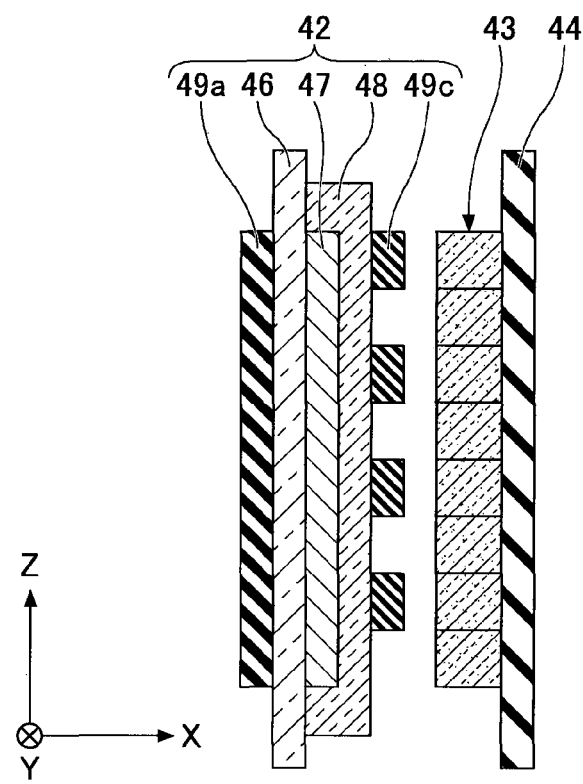
FIG. 47 shows a sectional view taken along a C-C line of FIG. 44.

FIG. 44 shows a view of the optical filter 42A according to the first variant of the first embodiment viewed from the side of the sensor substrate 44. FIG. 45 illustrates the correspondence of positional relationship between the optical filter 42A according to the first variant of the first embodiment and the image sensor 43. FIG. 46 shows a sectional view taken along the B-B line of FIG. 44. FIG. 47 shows a sectional view taken along the C-C line of FIG. 44.

A view of the surface of the image sensor 43 which faces the optical filter 42A viewed from the side of the sensor substrate 44 in a see-through manner is the same as FIG. 26 and thus is omitted. It is noted that in FIGS. 44 and 45, for the sake of convenience, areas corresponding to spectral filter layers 49c and the corresponding areas on the image sensor 43 are filled by dots. Further, in the optical filter 42A shown in FIG. 45, the broken lines drawn along the peripheral part of the spectral filter layers 49c indicate an effective image pickup area.

As shown in FIGS. 44, 45, 46 and 47, the optical filter 42A according to the first variant of the first embodiment is different from the first embodiment in that the spectral filter layers 49c are formed in a check pattern corresponding to the respective pixels of the image sensor 43.

For example, as being enclosed by the alternate long and short dash line in FIG. 26, total 4 pixels $43a_1$, $43a_2$, $43b_1$ and $43b_2$ of vertically adjacent two pixels by horizontally adjacent two pixels may be used to form one unit of pickup image data. For the one unit enclosed by the alternate long and short dash line, the light source 30 emits light, and the timing of emitting light and the timing of image pickup are synchronized. Thus, the p-polarized element of the infrared from the incident light on the optical filter 42A is received by the pixels $43a_2$ and $43b_1$, and it is possible to obtain an image by the p-polarized element of the infrared light.

Further, with the timing of the light source 30 having been turned off, the p-polarized element of mainly visible light from the incident light on the optical filter 42A is received by the pixels $43a_1$ and $43b_2$, and it is possible to obtain an image by the p-polarized element of mainly visible light. Further, the one unit enclosed by the alternate long and short dash line is shifted in sequence, the same operations are repeated and thus it is possible to obtain the image corresponding to all the pixels of the image sensor 43.

By using the image of the p-polarized element of infrared light and the image of the p-polarized element of mainly visible light thus obtained, it is possible to take images of an adhered object such as a raindrop that has adhered to the windshield of the vehicle and vehicle surrounding information such as a headlight of another vehicle, as described above.

It is noted that in these sets of pickup image data, the number of image pixels is smaller than the number of pickup pixels (i.e., information of adjacent pixel areas is lacked). In order to obtain an image with a higher resolution, a generally known image interpolation techniques may be used. For example, for obtaining an image of a p-polarized element of infrared light with a higher resolution, the following method may be used.

That is, the information of p-polarized element of infrared light is used as it is for the pixels $43a_2$ and $43b_1$. For the pixel $43b_2$, for example, the average of the pixels $43a_2$, $43b_1$, $43b_3$ and $43c_2$ that surround the pixel $43b_2$ may be used as the information of p-polarized element of infrared light. The same or similar way may be applied also for a case of obtaining an image of the p-polarized element of mainly visible light with a higher resolution.

Second Variant of First Embodiment

A second variant of the first embodiment is an example in which the area dividing method of the spectral filter layer on the side of the image sensor 43 is changed. For the second variant of the first embodiment, description for the same elements as those already described above will be omitted.

Figure 48:
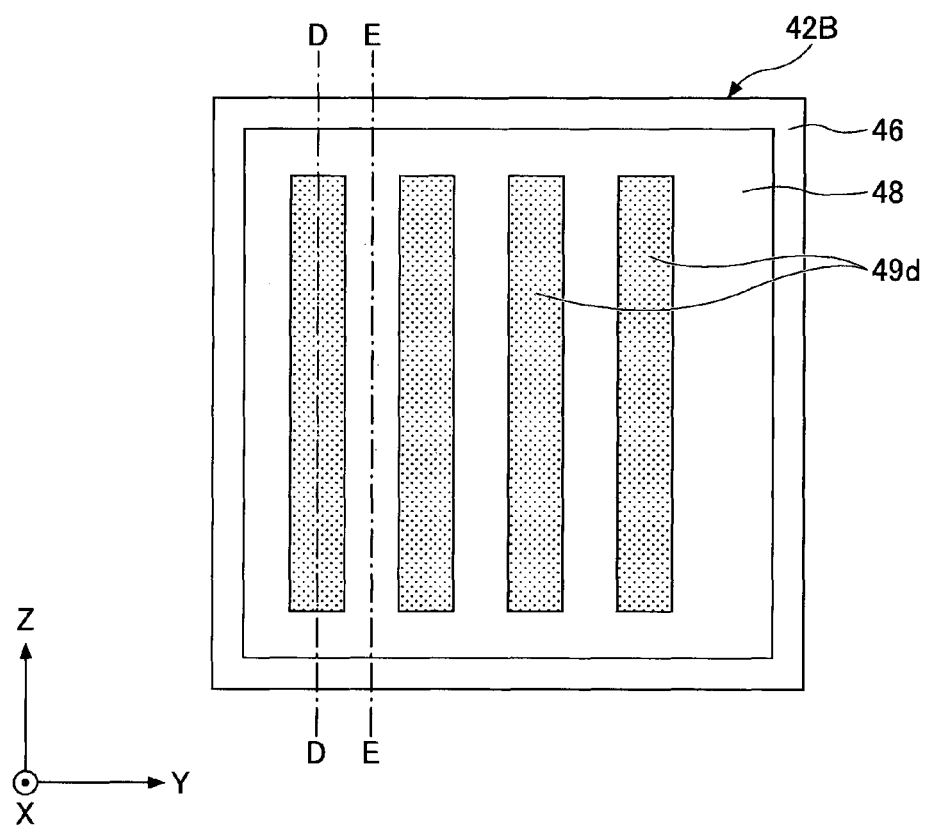
FIG. 48 shows a view of an optical filter 42B according to a second variant of the first embodiment viewed from the side of the sensor substrate 44.
Figure 49:
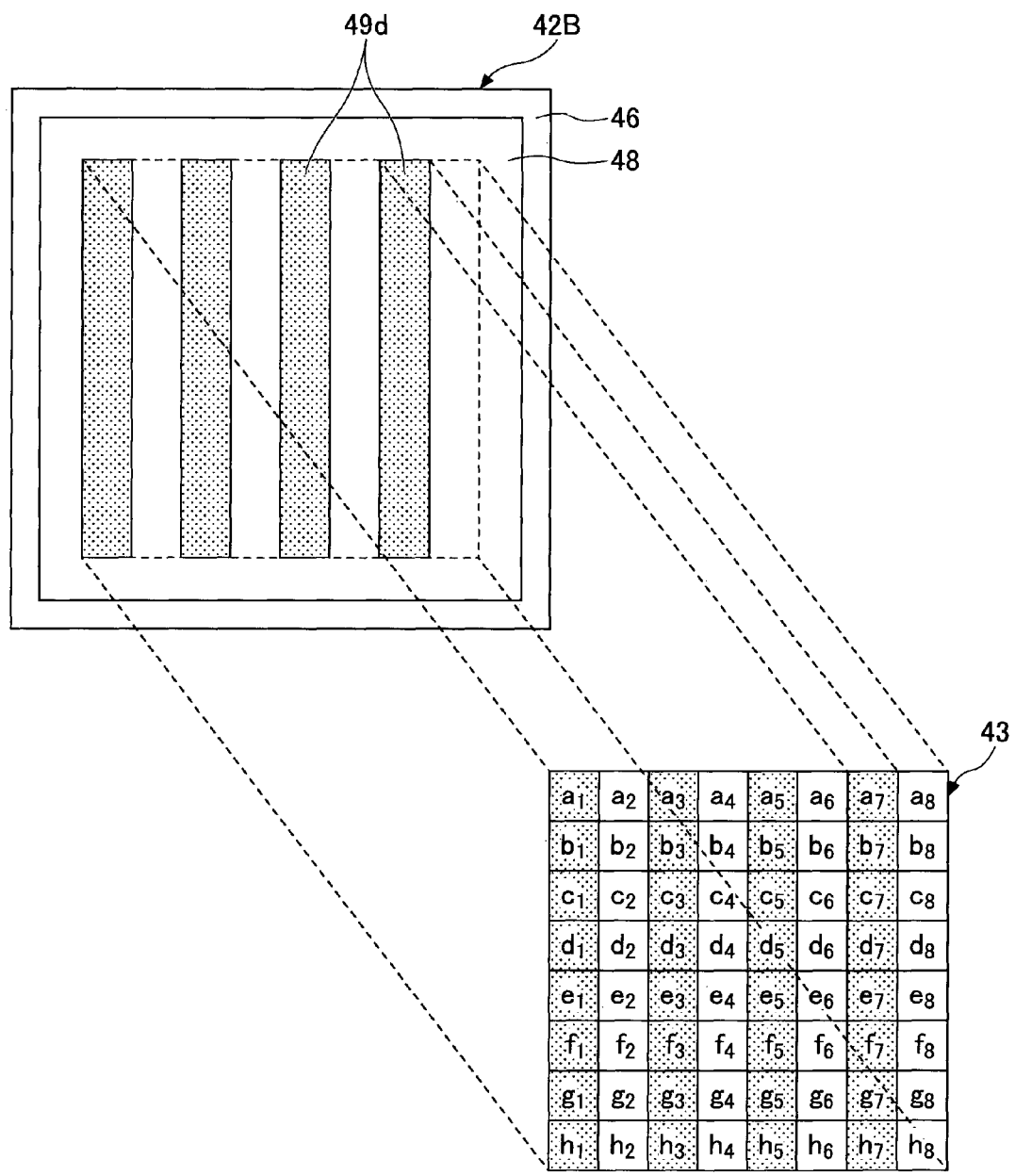
FIG. 49 illustrates a correspondence of positional relationship between the optical filter 42B and the image sensor 43 according to the second variant of the first embodiment.
Figure 50:
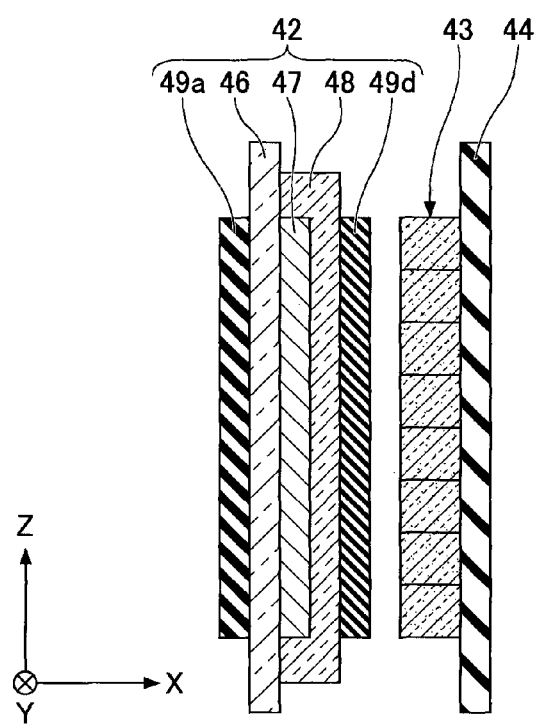
FIG. 50 shows a sectional view taken along a D-D line of FIG. 48.
Figure 51:
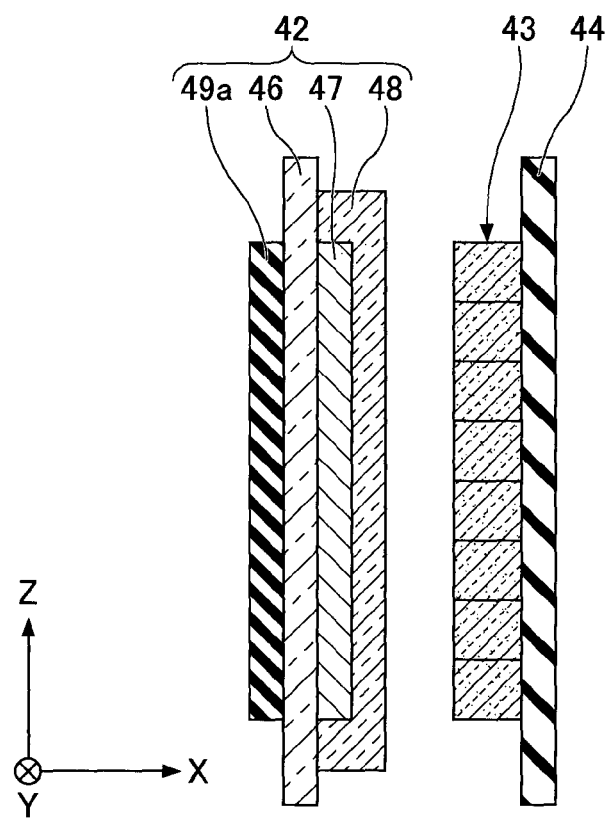
FIG. 51 shows a sectional view taken along an E-E line of FIG. 48.

FIG. 48 shows a view of the optical filter 42B according to the second variant of the first embodiment viewed from the side of the sensor substrate 44. FIG. 49 illustrates the correspondence of positional relationship between the optical filter 42B according to the second variant of the first embodiment and the image sensor 43. FIG. 50 shows a sectional view taken along the D-D line of FIG. 48. FIG. 51 shows a sectional view taken along the E-E line of FIG. 48.

A view of the surface of the image sensor 43 which faces the optical filter 42B viewed from the side of the sensor substrate 44 in a see-through manner is the same as FIG. 26 and thus is omitted. It is noted that in FIGS. 48 and 49, for the sake of convenience, areas corresponding to spectral filter layers 49d and the corresponding areas on the image sensor 43 are filled by dots. Further, in the optical filter 42B shown in FIG. 49, the broken lines drawn along the peripheral part of the spectral filter layers 49d indicate an effective image pickup area.

As shown in FIGS. 48, 49, 50 and 51, the optical filter 42B according to the second variant of the first embodiment is different from the first embodiment in that the spectral filter layers 49d are formed in a stripe pattern corresponding to the respective pixels of the image sensor 43.

For example, as being enclosed by the alternate long and short dash line in FIG. 26, total 4 pixels $43a_1$, $43a_2$, $43b_1$ and $43b_2$ of vertically adjacent two pixels by horizontally adjacent two pixels may be used to form one unit of pickup image data. For the one unit enclosed by the alternate long and short dash line, the light source 30 emits light, and the timing of emitting light and the timing of image pickup are synchronized. Thus, the p-polarized element of infrared from the incident light on the optical filter 42B is received by the pixels $43a_1$ and $43b_1$, and it is possible to obtain an image by the p-polarized element of the infrared light.

Further, with the timing of the light source 30 having been turned off, the p-polarized element of mainly visible light from the incident light on the optical filter 42B is received by the pixels $43a_2$ and $43b_2$, and it is possible to obtain an image by the p-polarized element of mainly visible light. Further, the one unit enclosed by the alternate long and short-dash line is shifted in sequence, the same operations are repeated and thus it is possible to obtain the image corresponding to all the pixels of the image sensor 43.

By using the image of the p-polarized element of infrared light and the image of the p-polarized element of mainly visible light thus obtained, it is possible to take images of an adhered object such as a raindrop that has adhered to the windshield of the vehicle and vehicle surrounding information such as a headlight of another vehicle, as described above. It is noted that the same as the first variant of the first embodiment, image interpolation techniques may be used.

Specific advantageous effects of the second variant of the first embodiment will now be described. That is, according to the second variant of the first embodiment, it is possible to ease the positional accuracy between the respective pixels of the image sensor 43 and the parts at which the spectral filter layers 49d are formed in the optical filter 42B by forming the spectral filter layers 49d in the stripe pattern in comparison to the check pattern of the first variant of the first embodiment.

That is, in the case of the check pattern such as that of the first variant of the first embodiment, it is necessary to carry out positional adjustment for the Y-direction and Z-direction so as to cause the respective pixels of the image sensor 43 and the parts at which the spectral filter layers 49c are formed in the optical filter 42B to be coincident. In comparison thereto, with the stripe pattern such as that of the second variant of the first embodiment, it is necessary to carry out positional adjustment only for the Y-direction so as to cause the respective pixels of the image sensor 43 and the parts at which the spectral filter layers 49d are formed in the optical filter 42B to be coincident. Thus, it is possible to shorten the assembling period of time and simplify the assembling equipment in a process of adhering the optical filter 42B and the image sensor 43 together.

It is noted that it is preferable to set the stripe direction of the stripe pattern (in FIG. 48, the Z-direction) to make it coincident with the light emitting direction of the light source 30 for emitting light to a raindrop 102. More specifically, it is preferable that the stripe direction of the stripe pattern (in FIG. 48, the Z-direction) is parallel to the plane that is formed by the optical axis of the emitted light of the light source 30 toward the windshield 101 and the optical axis of the image pickup device 40.

This is because when taking an image of a raindrop 102 that has adhered to the windshield 101, an image which is compressed in the vertical direction (Z-direction) is obtained. That is, as a result of the stripe direction being the vertical direction (Z-direction) as shown in FIG. 48, the resolution with which infrared light information of the vertical direction (Z-direction) is taken is improved, and thus, it is possible to efficiently detect a raindrop with high accuracy even from the image compressed in the vertical direction (Z-direction).

Third Variant of First Embodiment

A third variant of the first embodiment is an example of providing aperture limiting parts at areas at which the spectral filter layers are not formed. It is noted that description of the same elements as those already described will be omitted.

Figure 52:
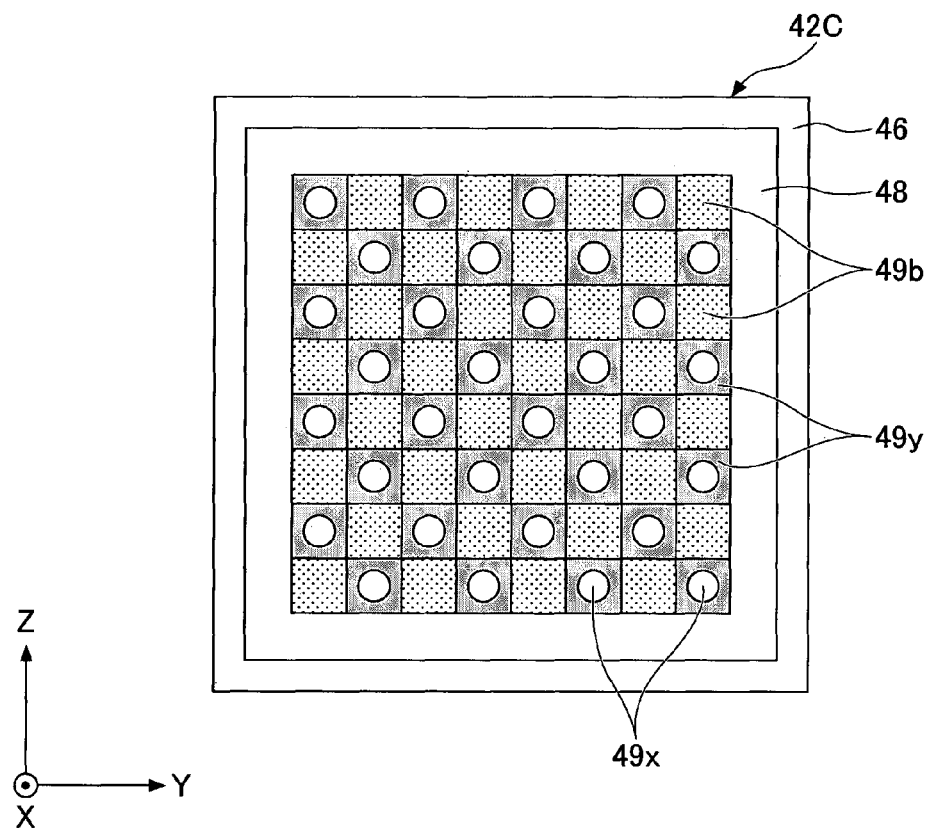
FIG. 52 shows a view of an optical filter 42C according to a third variant of the first embodiment viewed from the side of the sensor substrate 44.

FIG. 52 shows a view of an optical filter 42C according to the third variant of the first embodiment viewed from the side of the sensor substrate 44. The positional relationship between the optical filter 42C and the image sensor 43 and the sectional view thereof are the same as or similar to those of the first variant of the first embodiment, and figures thereof are omitted. It is noted that in FIG. 52, for the sake of convenience, the spectral filter layers 49b are filled with dots and the aperture limiting parts are painted in grey color.

As shown in FIG. 52, the optical filter 42C according to the third variant of the first embodiment is different from the first variant of the first embodiment in that apertures 49x and the aperture limiting parts 49y are provided corresponding to the respective pixels at areas at which the spectral filter layers 49b are not formed.

For example, as being enclosed by the alternate long and short dash line in FIG. 26, total 4 pixels $43a_1$, $43a_2$, $43b_1$ and $43b_2$ of vertically adjacent two pixels by horizontally adjacent two pixels may be used to form one unit of pickup image data. For the one unit enclosed by the alternate long and short dash line, the light source 30 emits light, and the timing of emitting light and the timing of image pickup are synchronized. Thus, the p-polarized element of the infrared from the incident light on the optical filter 42C is received by the pixels $43a_2$ and $43b_1$, and it is possible to obtain an image by the p-polarized element of infrared light.

Further, with the timing of the light source 30 having been turned off, the p-polarized element of mainly visible light for which the apertures have been limited from the incident light on the optical filter 42C is received by the pixels $43a_1$ and $43b_2$, and it is possible, to obtain an image by the p-polarized element of mainly visible light for which the apertures have been limited. However, at the pixels $43a_1$ and $43b_2$, the p-polarized element of mainly visible light for which the apertures have been limited is received. Thus, the image of the p-polarized element of mainly visible light is generated by the received amount of light smaller than the first variant of the first embodiment.

Further, the one unit enclosed by the alternate long and short dash line is shifted in sequence, the same operations are repeated and thus it is possible to obtain the image corresponding to all the pixels of the image sensor 43.

By using the image of the p-polarized element of infrared light and the image of the p-polarized element of mainly visible light for which the apertures have been limited thus obtained, it is possible to take images of an adhered object such as a raindrop that has adhered to the windshield of the vehicle and vehicle surrounding information such as a headlight of another vehicle, as described above. It is noted that the same as the first variant of the first embodiment, image interpolation techniques may be used.

Figure 53:
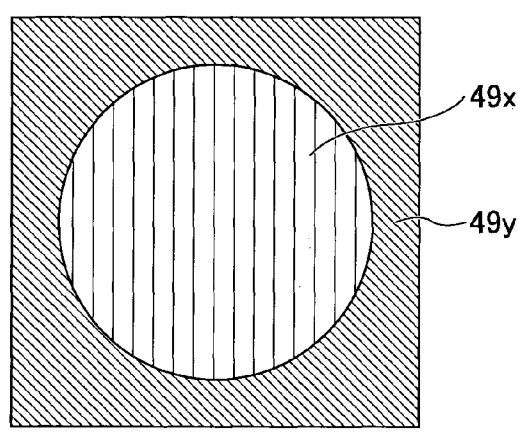
FIGS. 53, 54, 55, 56, 57 and 58 illustrate aperture limiting parts.

FIG. 53 shows one example of the aperture limiting part. In FIG. 53, the aperture 49x is made of a circular wire grid structure, and the aperture limiting part 49y made of a solid film of aluminium is formed around the aperture 49x. Thereby, it is possible to limit the received amounts of light for the areas at which the spectral filter layers 49b are not formed.

In the configuration of FIG. 53, the incident light is blocked by the aperture limiting part 49y made of the solid film of aluminium. Thus, it is possible to limit the received amount of light that is transmitted by the areas at which the spectral filter layers 49b are not formed, according to the size (aperture ratio) of the apertures 49x made of the wire grid structures.

Figure 54:
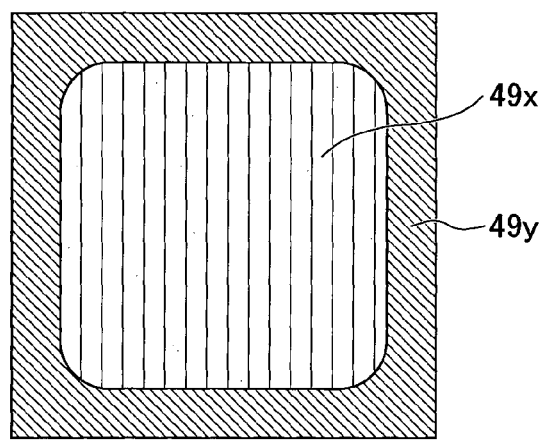

It is noted that the shape of the aperture limiting part 49y made of the wire grid structure axis is not limited to the circular shape as shows in FIG. 53. For example, the shape of the aperture limiting part 49y may be an approximately rectangular shape as shown in FIG. 54. In the case where the corner parts are included as shown in FIG. 54, it is suitable that the corner parts have radii as shown in FIG. 54 so that the shapes and sizes can be easily obtained through an etching process or the like.

The apertures 49x and the aperture limiting parts 49y can be made simultaneously together with the polarization filter layer 47, for example. Specifically, after an aluminium film is uniformly formed on the filter substrate 46, the aluminium film is removed through an etching process or the like at the areas of forming the spectral filter layers 49b and the areas of forming the apertures 49x. Then, the wire grid structures are formed at the areas from which the aluminium film has been thus removed.

In a case where the aperture limiting is thus carried out by providing the light blocking areas of aluminium around the wire grid structures, respectively, it is possible to achieve the aperture limiting by a process of leaving the aluminium film around each wire grid structure when the wire grid structure is formed. The wire grid structures will become the apertures 49x and also will become the polarization filter layer 47. Thus, it is possible to simplify the manufacturing process in comparison to a case where a process of carrying out the aperture limiting is carried out separately from the polarization filter layer 47.

Figure 55:
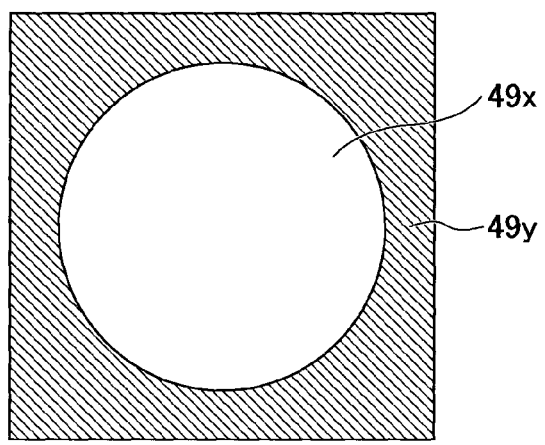

It is noted that it is also possible to provide the aperture limiting parts 49y as shown in FIG. 55 on a layer different from the polarization filter layer 47. In this case, no wire grid structures are formed in the apertures 49x.

Figure 56:
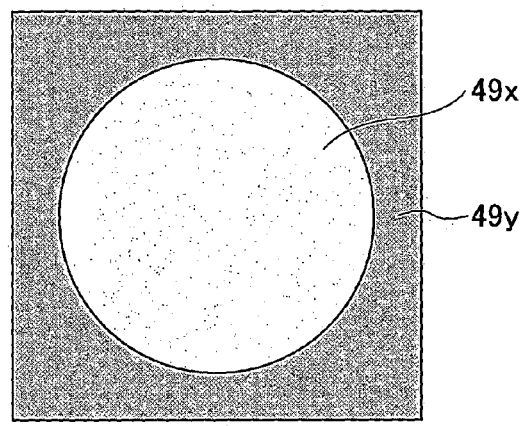
Figure 57:
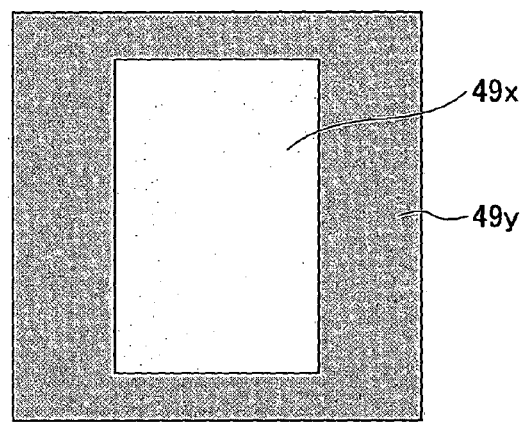

Further, the aperture limiting parts 49y are not limited to the reflective films such as the above-mentioned aluminium films. For example, films that absorb light may also be used to form the aperture limiting parts 49y. For example, as shown in FIG. 56, the aperture limiting parts 49y may also be made of solid films of black photoresist. Also in this case, the apertures 49x is not limited to the circular shape (see FIG. 56). For example, the aperture 49x may have an approximately rectangular shape as shown in FIG. 57.

Figure 58:
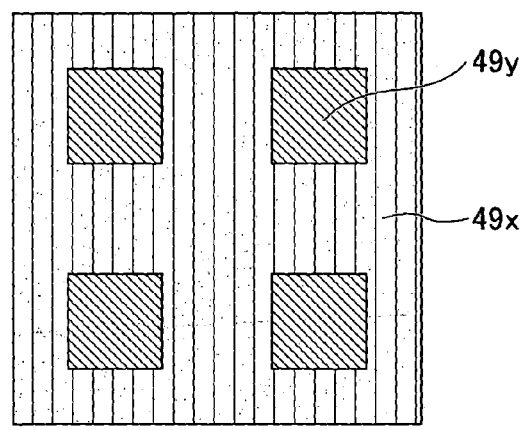

Further, plural of the apertures 49x may be provided in an area corresponding to each pixel of the image sensor 43 of areas at which no spectral filter layers 49b are formed. It is also possible to form plural of the aperture limiting parts 49y for an area corresponding to each pixel of the image sensor 43 of areas at which no spectral filter layers 49b are formed. Further, the aperture limiting parts 49y may not necessarily be provided around the apertures 49x, respectively. It is also possible to provide the aperture limiting parts 49y inside the apertures 49x, respectively. For example, as shown in FIG. 58, the aperture limiting parts 49y made of solid films of aluminium may be discretely arranged inside the aperture 49x made of the wire grid structure.

Advantageous effects of the third variant of the first embodiment are as follows: That is, for example, by making the aperture limiting parts 49y in such a manner that the received amount of light of the p-polarized element of mainly visible light will be equal to the received amount of light of the p-polarized element of infrared light, it is possible to obtain information of the infrared light for determining whether a raindrop exists and the visible light for detecting vehicle surrounding information by a single time of exposure without carrying out complicated exposure control.

According to one aspect of the present invention, it is possible to provide an image pickup unit or the like which can take an image of an adhered object that has adhered to a transparent member such as a windshield and an object far from the transparent member in respective suitable conditions.

APPLICATION EXAMPLE

As an application example, an example will now be described of configuring an on-vehicle equipment control system using an image processing apparatus according to the first embodiment.

Figure 59:
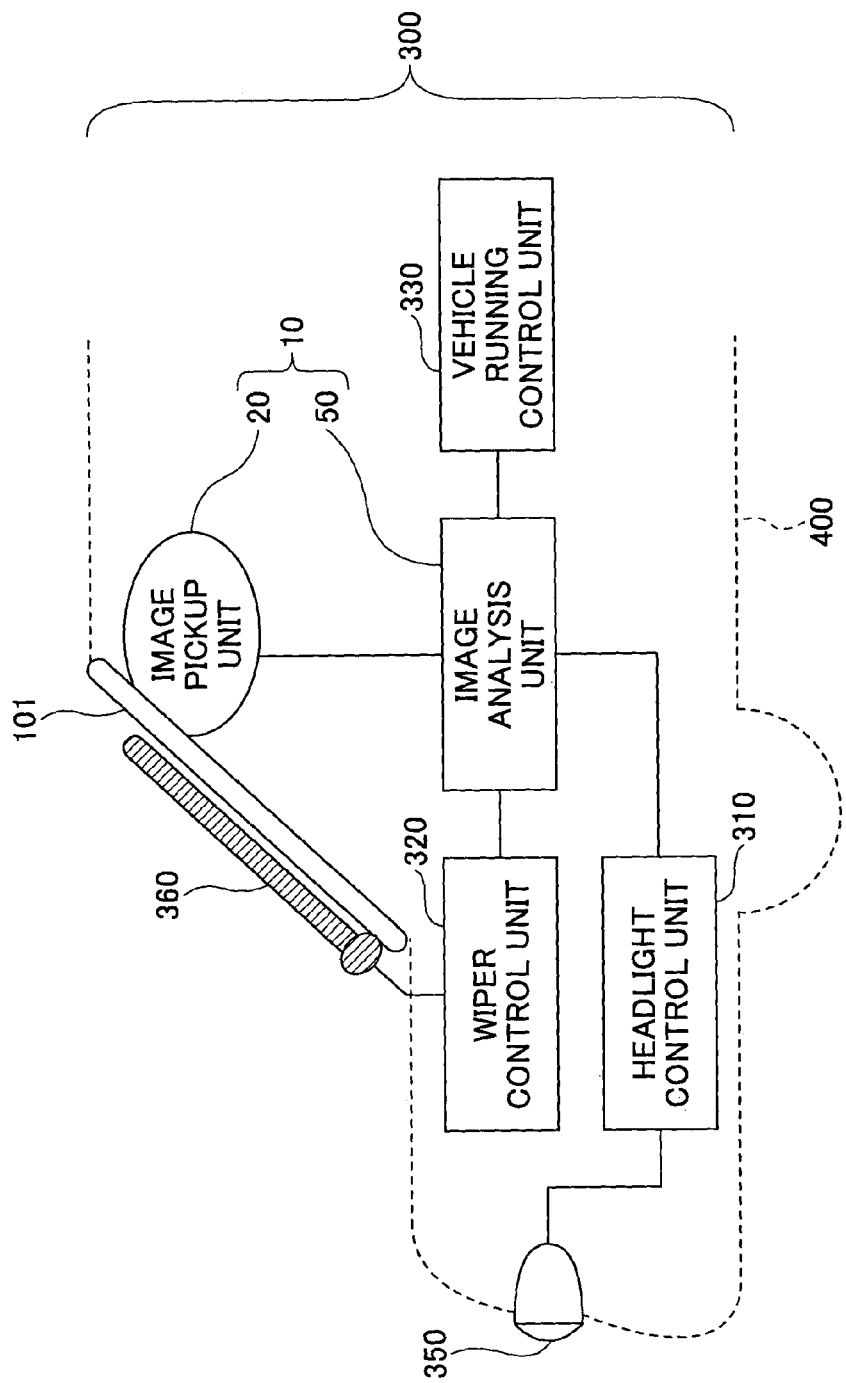
FIG. 59 schematically shows a general configuration of an in-vehicle equipment control system including an image processing apparatus according to the first embodiment.

FIG. 59 schematically illustrates a general configuration of an on-vehicle equipment system including an image processing apparatus according to the first embodiment. As shown in FIG. 59, the on-vehicle equipment control system 300 includes the image processing apparatus 10 according to the first embodiment, a headlight control unit 310, a wiper control unit 320, a vehicle running control unit 330, a headlight 350 and a wiper 360. It is noted that in FIG. 59, the reference numeral 400 denotes an occupant vehicle such as an automobile.

The on-vehicle equipment control system 300 has functions of light distribution control of the headlight 350, driving control of the wiper 360 and control of other on-vehicle equipment by using pickup image data of an image of the occupant vehicle running direction forward area (image pickup area) taken by the image pickup device 40 of the image processing apparatus 10 mounted in the occupant vehicle 400.

The pickup image data of an image taken by the image pickup device 40 is input to the image analysis unit 50. As described above, the image analysis unit 50 analyzes the pickup image data transmitted by the image pickup device 40 and thus, calculates the position, direction, distance and/or the like of another vehicle that exists in front of the occupant vehicle 400, for example.

Further, as described above, the image analysis unit 50 identifies a taillight of another vehicle and detects a vehicle moving in the same direction as and ahead of the occupant vehicle 400; and identifies a headlight of another vehicle and detects an oncoming vehicle moving in the opposite direction to the occupant vehicle 400. Further, as described above, the image analysis unit 50 detects an adhered object such as a raindrop 102, a foreign object or the like that has adhered to the windshield 101, and detects a detection target such as a white line (carriageway marking) or the like which exists on the road surface in the image pickup area.

The analysis results of the image analysis unit 50 are given to the headlight control unit 310. The headlight control unit 310 generates a control signal for controlling the headlight 350 that is on-vehicle equipment from distance data calculated by the image analysis unit 50, for example.

Specifically, control of switching between a high beam and a low beam of the headlight 350 and/or partial light blocking control of the headlight 350 are carried out so as to avoid dazzling the driver of another vehicle by preventing strong light of the headlight 350 of the occupant vehicle 400 from being incident on the eyes of the driver of the vehicle moving ahead of the occupant vehicle or the oncoming vehicle, and also, ensure the viewing ability of the driver of the occupant vehicle.

The analysis results of the image analysis unit 50 are also given to the wiper control unit 320. The wiper control unit 320 controls the wiper 360, and removes an adhered object such as a raindrop 102, a foreign object and/or the like that has adhered to the windshield 101 of the occupant vehicle 400. In response to a foreign object detection result given by the image analysis unit 50, the wiper control unit 320 generates a control signal. When the control signal generated by the wiper control unit 320 is given to the wiper 360, the wiper is driven so as to ensure the viewing ability of the driver of the occupant vehicle 400.

The analysis results of the image analysis unit 50 are also given to the vehicle running control unit 330. The vehicle running control unit 330 warns the driver of the occupant vehicle 400 in a case where the occupant vehicle 400 has deviated from the traffic lane area defined by white lines based on white line detection results given by the image analysis unit 50, for example. Further, the vehicle running control unit 330 carries out driving support control such as controlling the steering wheel and/or the brake of the occupant vehicle, for example.

Thus, it is possible to configure the on-vehicle equipment control system 300 using the image processing apparatus 10 according to the first embodiment. However, the image processing apparatus 10 according to the first embodiment may be applied not only to such an on-vehicle equipment control system but also, for example, to another system in which an object detection apparatus that carries out object detection based on a pickup image is mounted, or the like.

Thus, the image pickup unit and the vehicle in which the image pickup unit is mounted have been described by the embodiment and the variants thereof. However, the present invention is not limited to the embodiment and the variants thereof, and variations and modifications (including replacements) exist within the scope and spirit of the invention as described and defined in the following claims.

For example, according to the first embodiment and the variants thereof, it is assumed that the image sensor 43 is an imaging element for monochrome images. However, the image sensor 43 may be an imaging element for color images. In a case where the image sensor 43 is an imaging element for color images, light transmission characteristics of the respective areas of the polarization filter layer 47 and the spectral filter layers 49a and 49b may be adjusted depending on the characteristics of color filters attached to the respective pixels of the imaging element for color images.

Further, for the first embodiment and the variants thereof, the examples have been described in which the spectral filter layer 49a is formed on the surface of the filter substrate 46 on the side of the image pickup lens 41 and the spectral filter layers 49b are formed on the surface of the packing member 48 on the side of the image sensor 43. However, it is also possible to form the spectral filter layers 49b on the surface of the filter substrate 46 on the side of the image pickup lens 41 and form the spectral filter layer 49a on the surface of the packing member 48 on the side of the image sensor 43.

However, although advantageous effects the same as or similar to the former case can be obtained in this case, there may be a possibility that the boundaries between the spectral filter layer 49a and the spectral filter layers 49b are blurred in comparison to the former case and the boundaries between the raindrop detection image areas and the vehicle detection image area are not clear. Thus, the former configuration is preferable for making the boundaries between the raindrop detection image areas and the vehicle detection image area clearer.

For the first embodiment and the variants thereof, the examples have been described in which the automobile has been cited as one example of the vehicle. However, embodiments may also be applied to other vehicles such as an airplane, an electric train and so forth.

The present application is based on Japanese Priority Application No. 2011-240848 filed on Nov. 2, 2011 and Japanese Priority Application No. 2012-1942.46 filed on Sep. 4, 2012, the entire contents of which are incorporated herein by reference.

The invention claimed is:

1. An image pickup unit comprising:
a light source that emits light toward a transparent member from a side of one surface of the transparent member;
an image pickup lens having a focal length that is set far from a position of the transparent member;
an image sensor that includes plural pixels arranged two-dimensionally; and
an image pickup device that is put on the side of the transparent member the same as that of the light source, wherein the image pickup device takes an image of reflected light that includes regular reflection of the emitted light reflected by an interface between an adhered object that adheres to the other surface of the transparent member and air by using the image sensor, and the light source is put in a position such that in a case where an incident angle of the emitted light on the transparent member when the light reflected in a regular reflection manner by the other surface of the transparent member is incident on the image pickup lens is $\theta s$, an incident angle of a typical light beam of the emitted light on the transparent member falls within a range $\theta s-30$ deg through $\theta s$ and an incident angle of a main element of the emitted light on the transparent member is less than $\theta s$.

2. The image pickup unit as claimed in claim 1, further comprising an optical filter that is put subsequent to the image pickup lens, wherein light having passed through the optical filter is received by the image sensor, the optical filter includes a substrate that transmits incident light that is incident via the image pickup lens, and a spectral filter layer that is formed at a part of an effective image pickup area on the substrate and selectively transmits light of a wavelength band including an oscillation wavelength range of the light source from the incident light, and the image pickup device takes the image of reflected light that includes regular reflection of the emitted light reflected by the interface between the adhered object that adheres to the other surface of the transparent member and air by using pixels corresponding to an area at which the spectral filter layer is formed.

3. The image pickup unit as claimed in claim 1, the image pickup unit emitting light from the side of the one surface of the transparent member toward a second adhered object that adheres to the one surface of the transparent member, and taking an image of scattered light of the emitted light reflected by the second adhered object.

4. The image pickup unit as claimed in claim 3, the image pickup unit taking an image of the reflected light via a polarization filter layer that transmits only a p-polarized element, and taking an image of the scattered light via a polarization filter layer that transmits only an s-polarized element.

5. The image pickup unit as claimed in claim 1, wherein the light source is put in such a manner that in a case where an angle of view for image pickup for the adhered object is $\theta u$, an incident angle of horizontal direction of the emitted light on the transparent member falls within a range $\theta u-20$ deg through $\theta u+20$ deg.

6. The image pickup unit as claimed in claim 1, further comprising another light source, wherein the other light source is put in such a manner that in a case where an angle of elevation of the image pickup lens with respect to a normal of the transparent member which intersects an optical axis of the image pickup lens is $\theta a$, an incident angle of vertical direction of the emitted light on the transparent member falls within a range $\theta a-50$ deg through $\theta a+20$ deg.

7. The image pickup unit as claimed in claim 1, wherein the image pickup device is put in such a manner that regular reflection from the one surface of the transparent member from the emitted light is prevented from being incident on the image pickup lens.

8. The image pickup unit as claimed in claim 2, wherein an incident position on the one surface of the transparent member of the emitted light is included in the effective image pickup area.

9. The image pickup unit as claimed in claim 1, further comprising:

a signal processing part that processes a signal of the image sensor at a time of emitting light from the light source and outputs an image signal; and an image analysis unit that carries out image processing based on an output of the signal processing part and outputs a signal as to whether a raindrop has been detected.

10. A vehicle having the image pickup unit claimed in claim 1 mounted in the vehicle, wherein the vehicle detects an adhered object that adheres to the other surface of the transparent member by the image pickup unit.

11. The vehicle as claimed in claim 10, further comprising:

a wiper control unit that controls a wiper, wherein the wiper control unit controls the wiper based on a detection result of the adhered object and removes the adhered object.

* * * * *